US012668842B2

(12) United States Patent
Schoenbrunner et al.

(10) Patent No.: US 12,668,842 B2
(45) Date of Patent: Jun. 30, 2026

(54) SEQUENCE CONVERSION REACTION

(71) Applicant: Rosalind DX Pte. Ltd., Singapore (SG)

(72) Inventors: Nancy Schoenbrunner, Charlestown, MA (US); Manuel Duval, Charlestown, MA (US); Erhard Ralf Schoenbrunner, Charlestown, MA (US)

(73) Assignee: Rosalind DX Pte. Ltd., Singapore (SG)

( * ) Notice: Subject to any disclaimer, the term of this patent is extended or adjusted under 35 U.S.C. 154(b) by 691 days.

(21) Appl. No.: 18/001,575

(22) PCT Filed: Jun. 10, 2021

(86) PCT No.: PCT/US2021/036766
§ 371 (c)(1),
(2) Date: Dec. 12, 2022

(87) PCT Pub. No.: WO2021/252733
PCT Pub. Date: Dec. 16, 2021

(65) Prior Publication Data
US 2023/0220474 A1     Jul. 13, 2023

Related U.S. Application Data

(60) Provisional application No. 63/166,955, filed on Mar. 26, 2021, provisional application No. 63/037,575, filed on Jun. 10, 2020.

(51) Int. Cl.
| | |
|---|---|
| *C12Q 1/6883* | (2018.01) |
| *C12Q 1/6837* | (2018.01) |
| *C12Q 1/6855* | (2018.01) |

(52) U.S. Cl.
CPC ......... *C12Q 1/6883* (2013.01); *C12Q 1/6837* (2013.01); *C12Q 1/6855* (2013.01); *C12Q 2600/156* (2013.01)

(58) Field of Classification Search
CPC ............ C12Q 1/6883; C12Q 2600/156; C12Q 2525/131; C12Q 2525/155; C12Q 2525/161
See application file for complete search history.

(56) References Cited

U.S. PATENT DOCUMENTS

| | | | |
|---|---|---|---|
| 7,435,794 | B2 | 10/2008 | Lukyanov et al. |
| 7,846,657 | B2 | 12/2010 | Van Eijk |
| 7,883,849 | B1 | 2/2011 | Dahl |
| 7,888,017 | B2 | 2/2011 | Quake et al. |
| 7,951,569 | B2 | 5/2011 | Hirakawa et al. |

(Continued)

FOREIGN PATENT DOCUMENTS

| | | |
|---|---|---|
| CA | 2767028 A1 | 6/2011 |
| WO | WO2010/113031 A2 | 10/2010 |

(Continued)

OTHER PUBLICATIONS

Kuhnemund, M. et al. Nucleic Acids Research 45(8):e59. Nov. 2017. (Year: 2017).*

(Continued)

*Primary Examiner* — Diana B Johannsen

(74) *Attorney, Agent, or Firm* — Shay Glenn LLP

(57) ABSTRACT

Disclosed herein are methods, compositions, and kits related to the identification and/or quantification of target molecules.

18 Claims, 44 Drawing Sheets

Specification includes a Sequence Listing.

(56) References Cited

U.S. PATENT DOCUMENTS

| | | | |
|---|---|---|---|
| 8,101,356 | B2 | 1/2012 | Yoo |
| 8,195,415 | B2 | 6/2012 | Fan et al. |
| 8,222,003 | B2 | 7/2012 | Gupta et al. |
| 8,574,842 | B2 | 11/2013 | Fan et al. |
| 8,703,652 | B2 | 4/2014 | Quake et al. |
| 8,808,991 | B2 | 8/2014 | Hodgers |
| 8,877,442 | B2 | 11/2014 | Quake et al. |
| 8,916,349 | B2 | 12/2014 | Nadeau et al. |
| 9,040,287 | B2 | 5/2015 | Chang et al. |
| 9,090,934 | B2 | 7/2015 | Lucero et al. |
| 9,267,174 | B2 | 2/2016 | Quake et al. |
| 9,404,157 | B2 | 8/2016 | Fan et al. |
| 9,487,802 | B2 | 11/2016 | Quake et al. |
| 9,683,259 | B2 | 6/2017 | Chun et al. |
| 9,828,629 | B2 | 11/2017 | Gupta |
| 9,982,291 | B2 | 5/2018 | Johnson et al. |
| 10,066,241 | B2 | 9/2018 | Quake et al. |
| 10,117,911 | B2 | 11/2018 | Quake et al. |
| 10,240,198 | B2 | 3/2019 | Dahl et al. |
| 10,253,365 | B1 | 4/2019 | Doudna et al. |
| 10,533,223 | B2 | 1/2020 | Oliphant et al. |
| 10,590,474 | B2 | 3/2020 | Belousov et al. |
| 10,961,569 | B2 | 3/2021 | Balmforth et al. |
| 2006/0292611 | A1 | 12/2006 | Berka et al. |
| 2010/0279295 | A1 | 11/2010 | Roy et al. |
| 2012/0065076 | A1 | 3/2012 | Peters et al. |
| 2014/0186827 | A1 | 7/2014 | Pieprzyk et al. |
| 2016/0102339 | A1 | 4/2016 | Komiya et al. |
| 2016/0281130 | A1 | 9/2016 | Dahl et al. |
| 2016/0333416 | A1 | 11/2016 | Babiarz et al. |
| 2017/0242960 | A1 | 8/2017 | Rabinowitz et al. |
| 2019/0177768 | A1 | 6/2019 | Kim et al. |
| 2019/0194758 | A1 | 6/2019 | Babiarz et al. |
| 2021/0189478 | A1 | 6/2021 | Balmforth et al. |
| 2025/0197936 | A1* | 6/2025 | Schoenbrunner .... C12Q 1/6813 |

FOREIGN PATENT DOCUMENTS

| | | | |
|---|---|---|---|
| WO | WO2015/069933 | A1 | 5/2015 |
| WO | WO2021/180791 | A1 | 9/2021 |

OTHER PUBLICATIONS

Wan, J.C.M. et al. Nature Reviews: Cancer 17:223. Apr. 2017. (Year: 2017).*

Tsui, C.K.M. et al. IMA Fungus 2(2):177. Nov. 2011. (Year: 2011).*

Watanabe, M. et al. Clinical Cancer Research 21(15):3552. Aug. 2015. (Year: 2015).*

Blanco, L. et al. Nucleic Acids Research 13(4):1239. (Year: 1985).*

Altschul et al.; Gapped BLAST and PSI-BLAST: a new generation of protein database search programs; Nucleic Acids research; 25(17); pp. 3389-3402; Sep. 1997.

Altschul et al.; Basic local alignment search tool; 215(3); pp. 403-410; Oct. 1990.

Zhang et al.; Predicting DNA hybridization kinetics from sequence; Nature Chemistry; 10(1); pp. 91-98; 18 pages; (Author Manuscript); Jan. 2018.

Longo et al.; Use of uracil DNA glycosylase to control carry-over contamination in polymerase chain reaction ;. Gene; 93(1); pp. 125-128; Sep. 1, 1990.

Schoenbrunner et al.; U.S. Appl. No. 18/718,429 entitled "Sequence conversion reaction," filed Jun. 10, 2024.

Gormley et al.; Reactions of BgII and other type II restriction endonucleases with discontinuous recognition sites; Journal of Biological Chemistry; 275(10); pp. 6928-6936; Mar. 10, 2000.

Logsdon et al.; The structure, function and evolution of a complete human chromosome 8; Nature; 593(7857); pp. 101-132; Apr. 7, 2021.

Moshen et al.; The discovery of rolling circle amplification and rolling circle transcription; Accounts of chemical research; 49(11); pp. 2540-2550; Nov. 15, 2016.

Pingoud et al.; Type II restriction endonucleases: structure and mechanism; Cellular and molecular life sciences; vol. 62; pp. 685-707; Mar. 1, 2005.

Taylor et al.; Human chromosome 11 DNA sequence and analysis including novel gene identification; Nature; 440(7083); pp. 497-500; Mar. 23, 2006.

* cited by examiner

R: Ribose in Sequence Conversion Probe, it's the cleavage site for RNase H2 which binds to RNA-DNA duplexes and cleaves the RNA strand
Or
Recognition Site for Restriction Enzyme

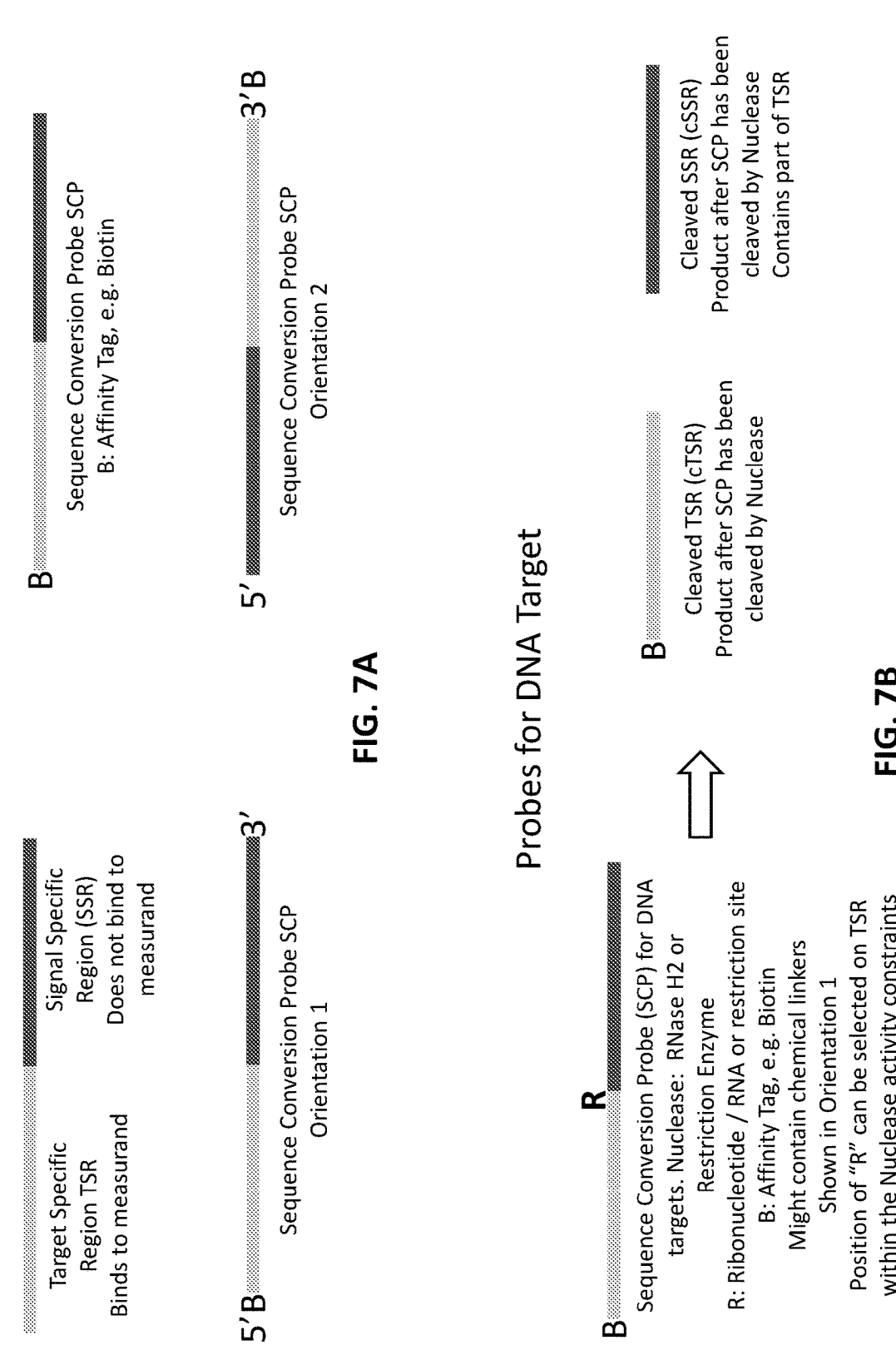

Basic Structure

Target Specific
Region TSR
Binds to measurand

Signal Specific
Region (SSR)
Does not bind to
measurand

B

Sequence Conversion Probe SCP
B: Affinity Tag, e.g. Biotin

5'B ............................ 3'

Sequence Conversion Probe SCP
Orientation 1

5' ............................ 3'B

Sequence Conversion Probe SCP
Orientation 2

FIG. 7A

Probes for DNA Target

B    R

Sequence Conversion Probe (SCP) for DNA
targets. Nuclease: RNase H2 or
Restriction Enzyme
R: Ribonucleotide / RNA or restriction site
B: Affinity Tag, e.g. Biotin
Might contain chemical linkers
Shown in Orientation 1
Position of "R" can be selected on TSR
within the Nuclease activity constraints

B ...........

Cleaved TSR (cTSR)
Product after SCP has been
cleaved by Nuclease

Cleaved SSR (cSSR)
Product after SCP has been
cleaved by Nuclease
Contains part of TSR

FIG. 7B

Probes for DNA and RNA Target

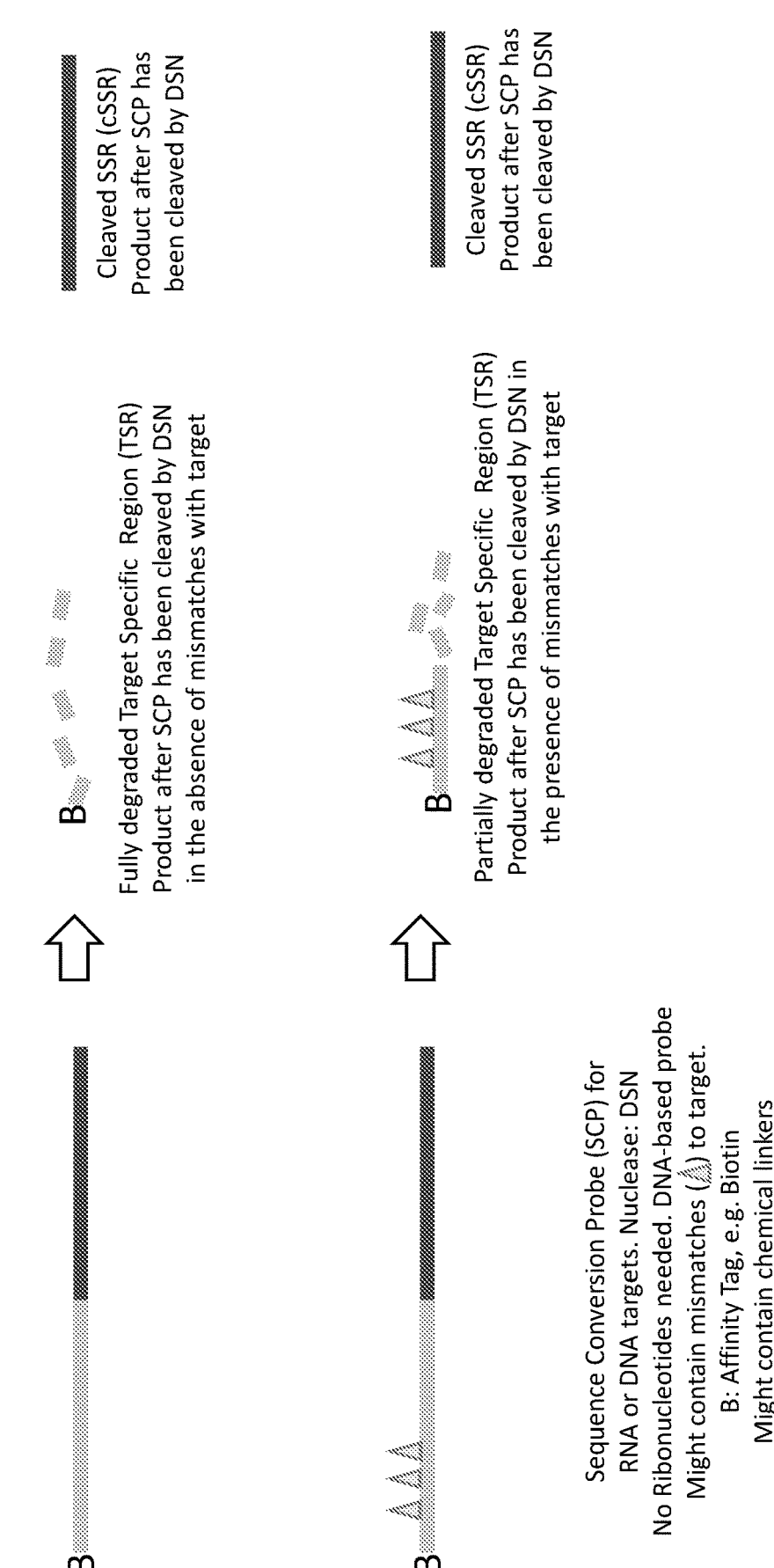

Cleaved SSR (cSSR)
Product after SCP has
been cleaved by DSN

Cleaved SSR (cSSR)
Product after SCP has
been cleaved by DSN

Fully degraded Target Specific Region (TSR)
Product after SCP has been cleaved by DSN
in the absence of mismatches with target Partially degraded Target Specific Region (TSR)
Product after SCP has been cleaved by DSN in
the presence of mismatches with target Sequence Conversion Probe (SCP) for
RNA or DNA targets. Nuclease: DSN
No Ribonucleotides needed. DNA-based probe
Might contain mismatches (△) to target.
B: Affinity Tag, e.g. Biotin
Might contain chemical linkers

Figures 8, 9:
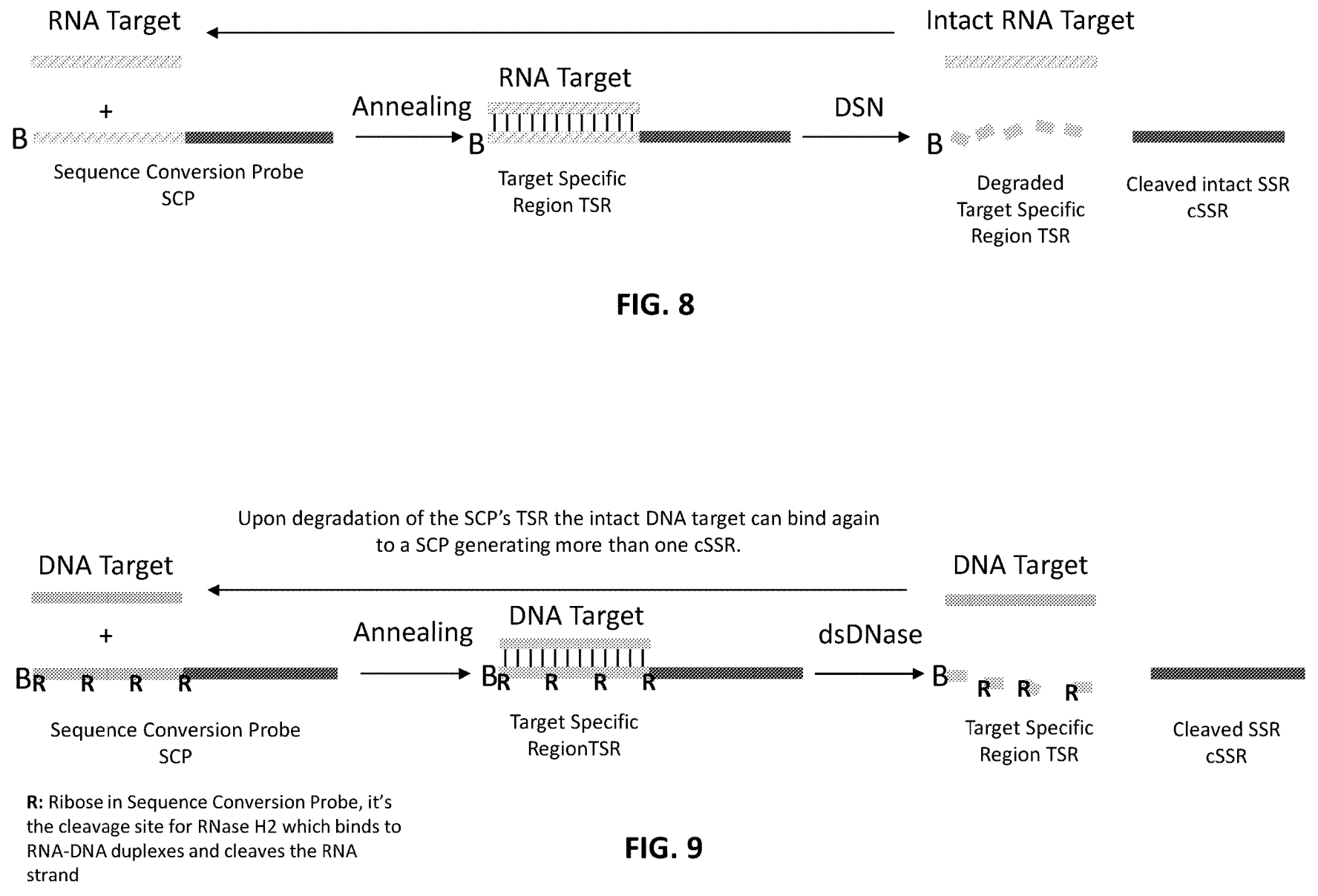

R: Ribose in Sequence Conversion Probe, it's
the cleavage site for RNase H2 which binds to
RNA-DNA duplexes and cleaves the RNA
strand R: Ribose in Sequence Conversion Probe, it's
the cleavage site for RNase H2 which binds to
RNA-DNA duplexes and cleaves the RNA
strand
Or
Recognition Site for Restriction Enzyme

SCP signal specific region (SSR)

Figures 17, 18:
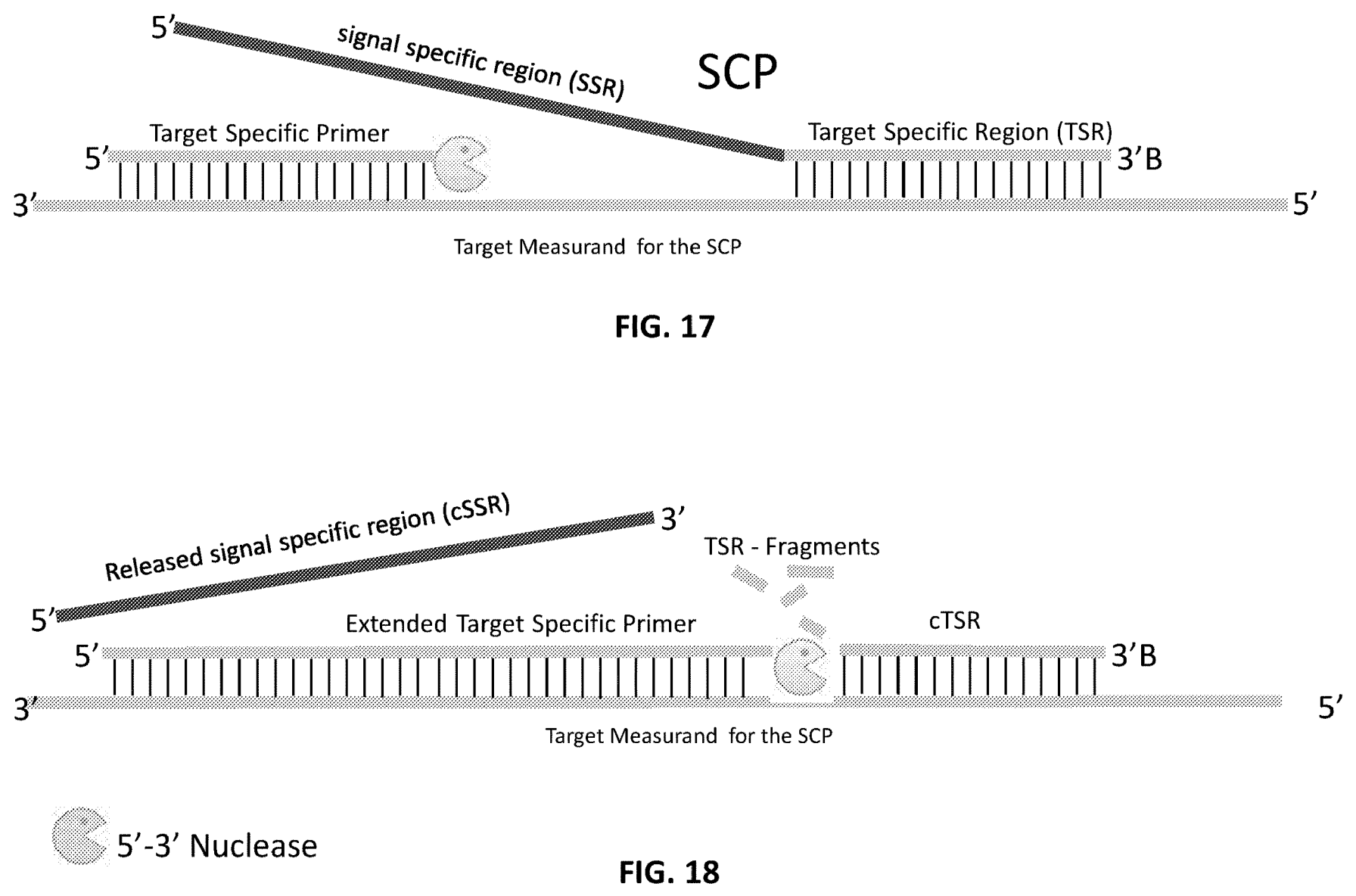

Target Specific Region (TSR)

3'B

5'

5'

Target Specific Primer

Target Measurand for the SCP

Released signal specific region (cSSR)

TSR - Fragments cTSR

3'B

5'

5'

Extended Target Specific Primer

Target Measurand for the SCP

5'-3' Nuclease

• delineates different functional regions

BspQI potential
recognition site

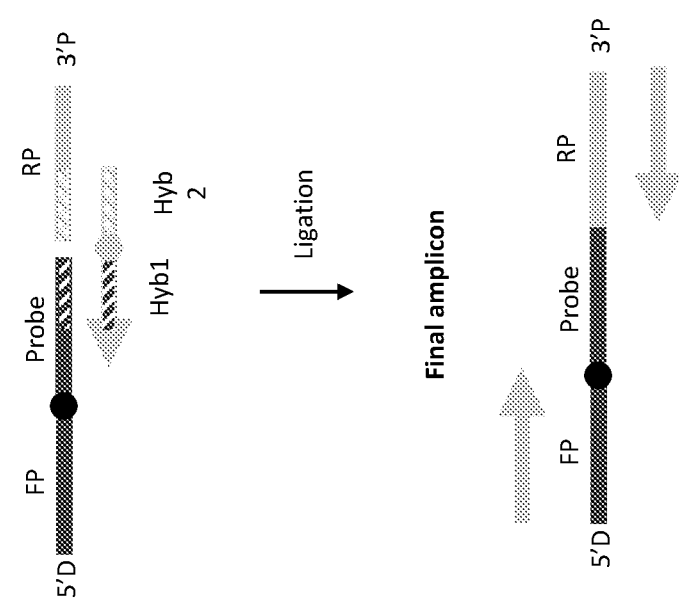
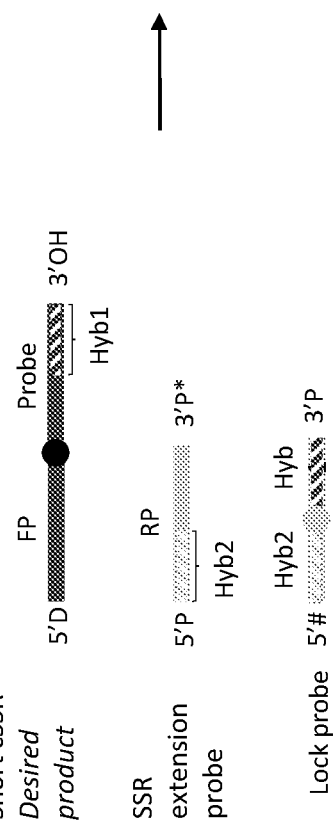
5' D: optional moiety to block ligation
P*: optional moiety (PO4) to block ligation, extension and/or exonuclease
5' #: optional moiety to block ligation
● delineates different functional regions
FIG. 29B

SEQUENCE LISTING

```
<160> NUMBER OF SEQ ID NOS: 99

<210> SEQ ID NO 1
<211> LENGTH: 65
<212> TYPE: DNA
<213> ORGANISM: Artificial Sequence
<220> FEATURE:
<223> OTHER INFORMATION: SSR Example 1

<400> SEQUENCE: 1
gctcggaccc tgctgtatcg ttcgcgggcc tcctcctcaa aaacgcgcca tatgagcccc      60
gtcgt                                                                   65

<210> SEQ ID NO 2
<211> LENGTH: 31
<212> TYPE: DNA
<213> ORGANISM: Artificial Sequence
<220> FEATURE:
<223> OTHER INFORMATION: SSR Example 1- Before abasic region

<400> SEQUENCE: 2
gctcggaccc tgctgtatcg ttcgcgggcc t                                      31

<210> SEQ ID NO 3
<211> LENGTH: 34
<212> TYPE: DNA
<213> ORGANISM: Artificial Sequence
<220> FEATURE:
<223> OTHER INFORMATION: SSR Example 1 - After abasic region

<400> SEQUENCE: 3
cctcctcaaa aacgcgccat atgagccccg tcgt                                   34

<210> SEQ ID NO 4
<211> LENGTH: 78
<212> TYPE: DNA
<213> ORGANISM: Artificial Sequence
<220> FEATURE:
<223> OTHER INFORMATION: SSR Example 2

<400> SEQUENCE: 4
gctcggaccc tgctgtatcg ttcgcgggcc tcctcctcaa aaacgcgcca tatgagcccc      60
gtcgtgatta cccgctga                                                     78
```

```
<210> SEQ ID NO 5
<211> LENGTH: 47
<212> TYPE: DNA
<213> ORGANISM: Artificial Sequence
<220> FEATURE:
<223> OTHER INFORMATION: SSR Example 2

<400> SEQUENCE: 5
cctcctcaaa aacgcgccat atgagccccg tcgtgattac ccgctga                47

<210> SEQ ID NO 6
<211> LENGTH: 18
<212> TYPE: DNA
<213> ORGANISM: Artificial Sequence
<220> FEATURE:
<223> OTHER INFORMATION: Forward primer for SSR Examples 1 and 2

<400> SEQUENCE: 6
cctcctcaaa aacgcgcc                                                18

<210> SEQ ID NO 7
<211> LENGTH: 18
<212> TYPE: DNA
<213> ORGANISM: Artificial Sequence
<220> FEATURE:
<223> OTHER INFORMATION: Reverse primer for SSR Examples 1 and 2

<400> SEQUENCE: 7
aggcccgcga acgataca                                                18

<210> SEQ ID NO 8
<211> LENGTH: 26
<212> TYPE: DNA
<213> ORGANISM: Artificial Sequence
<220> FEATURE:
<223> OTHER INFORMATION: TSR example 1 Chromosome 21 unique site with
      BSAI recognition site

<400> SEQUENCE: 8
taaaccctaa gagaccagat aaagct                                       26

<210> SEQ ID NO 9
<211> LENGTH: 91
<212> TYPE: DNA
<213> ORGANISM: Artificial Sequence
<220> FEATURE:
<223> OTHER INFORMATION: SCP combines Example 1 SSR with TSR example 1
      Chromosome 21 unique site with BSAI

<400> SEQUENCE: 9
gctcggaccc tgctgtatcg ttcgcgggcc tcctcctcaa aaacgcgcca tatgagcccc     60
gtcgttaaac cctaagagac cagataaagc t                                 91

<210> SEQ ID NO 10
<211> LENGTH: 31
<212> TYPE: DNA
<213> ORGANISM: Artificial Sequence
<220> FEATURE:
<223> OTHER INFORMATION: Partial SCP - Example 1 SSR before abasic site

<400> SEQUENCE: 10
gctcggaccc tgctgtatcg ttcgcgggcc t                                 31

<210> SEQ ID NO 11
```

-continued

```
<211> LENGTH: 60
<212> TYPE: DNA
<213> ORGANISM: Artificial Sequence
<220> FEATURE:
<223> OTHER INFORMATION: Partial SCP - Example 1 SSR with TSR example 1
      Chromosome 21 unique site with BSAI - after abasic site

<400> SEQUENCE: 11
cctcctcaaa aacgcgccat atgagccccg tcgttaaacc ctaagagacc agataaagct        60

<210> SEQ ID NO 12
<211> LENGTH: 26
<212> TYPE: DNA
<213> ORGANISM: Artificial Sequence
<220> FEATURE:
<223> OTHER INFORMATION: TSR example 2 Chromosome 21 unique site with
      BSAI

<400> SEQUENCE: 12
tcccctctgt gagaccttca gaaatc                                             26

<210> SEQ ID NO 13
<211> LENGTH: 91
<212> TYPE: DNA
<213> ORGANISM: Artificial Sequence
<220> FEATURE:
<223> OTHER INFORMATION: SCP combines Example 1 SSR with TSR example 2
      Chromosome 21 unique site with BSAI

<400> SEQUENCE: 13
gctcggaccc tgctgtatcg ttcgcgggcc tcctcctcaa aaacgcgcca tatgagcccc        60
gtcgttcccc tctgtgagac cttcagaaat c                                       91

<210> SEQ ID NO 14
<211> LENGTH: 60
<212> TYPE: DNA
<213> ORGANISM: Artificial Sequence
<220> FEATURE:
<223> OTHER INFORMATION: Partial SCP - Example 1 SSR with TSR example 2
      Chromosome 21 unique site with BSAI - after abasic site

<400> SEQUENCE: 14
cctcctcaaa aacgcgccat atgagccccg tcgttccct ctgtgagacc ttcagaaatc         60

<210> SEQ ID NO 15
<211> LENGTH: 26
<212> TYPE: DNA
<213> ORGANISM: Artificial Sequence
<220> FEATURE:
<223> OTHER INFORMATION: TSR example 3 Chromosome 21 unique site with
      BSAI

<400> SEQUENCE: 15
taatcaccgt gagaccagtt aatgag                                             26

<210> SEQ ID NO 16
<211> LENGTH: 91
<212> TYPE: DNA
<213> ORGANISM: Artificial Sequence
<220> FEATURE:
<223> OTHER INFORMATION: SCP combines Example 1 SSR with TSR example 3
      Chromosome 21 unique site with BSAI

<400> SEQUENCE: 16
gctcggaccc tgctgtatcg ttcgcgggcc tcctcctcaa aaacgcgcca tatgagcccc        60
gtcgttaatc accgtgagac cagttaatga g                                       91
```

```
<210> SEQ ID NO 17
<211> LENGTH: 60
<212> TYPE: DNA
<213> ORGANISM: Artificial Sequence
<220> FEATURE:
<223> OTHER INFORMATION: Partial SCP - Example 1 SSR with TSR example 3
      Chromosome 21 unique site with BSAI - after abasic site

<400> SEQUENCE: 17
cctcctcaaa aacgcgccat atgagccccg tcgttaatca ccgtgagacc agttaatgag        60

<210> SEQ ID NO 18
<211> LENGTH: 26
<212> TYPE: DNA
<213> ORGANISM: Artificial Sequence
<220> FEATURE:
<223> OTHER INFORMATION: TSR example 4 Chromosome 21 unique site with
      BSAI

<400> SEQUENCE: 18
aattttatga gagaccctag acagct                                             26

<210> SEQ ID NO 19
<211> LENGTH: 91
<212> TYPE: DNA
<213> ORGANISM: Artificial Sequence
<220> FEATURE:
<223> OTHER INFORMATION: SCP combines Example 1 SSR with TSR example 4
      Chromosome 21 unique site with BSAI

<400> SEQUENCE: 19
gctcggaccc tgctgtatcg ttcgcgggcc tcctcctcaa aaacgcgcca tatgagcccc        60
gtcgtaattt tatgagagac cctagacagc t                                       91

<210> SEQ ID NO 20
<211> LENGTH: 60
<212> TYPE: DNA
<213> ORGANISM: Artificial Sequence
<220> FEATURE:
<223> OTHER INFORMATION: Partial SCP - Example 1 SSR with TSR example 4
      Chromosome 21 unique site with BSAI - after abasic site

<400> SEQUENCE: 20
cctcctcaaa aacgcgccat atgagccccg tcgtaatttt atgagagacc ctagacagct        60

<210> SEQ ID NO 21
<211> LENGTH: 26
<212> TYPE: DNA
<213> ORGANISM: Artificial Sequence
<220> FEATURE:
<223> OTHER INFORMATION: TSR example 5 Chromosome 21 unique site with
      BSAI

<400> SEQUENCE: 21
gaattcttct gagacctgaa gtgtag                                             26

<210> SEQ ID NO 22
<211> LENGTH: 91
<212> TYPE: DNA
<213> ORGANISM: Artificial Sequence
<220> FEATURE:
<223> OTHER INFORMATION: SCP combines Example 1 SSR with TSR example 5
      Chromosome 21 unique site with BSAI

<400> SEQUENCE: 22
```
gctcggaccc tgctgtatcg ttcgcgggcc tcctcctcaa aaacgcgcca tatgagcccc          60
gtcgtgaatt cttctgagac ctgaagtgta g                                         91

<210> SEQ ID NO 23
<211> LENGTH: 60
<212> TYPE: DNA
<213> ORGANISM: Artificial Sequence
<220> FEATURE:
<223> OTHER INFORMATION: Partial SCP - Example 1 SSR with TSR example 5
      Chromosome 21 unique site with BSAI - after abasic site

<400> SEQUENCE: 23
cctcctcaaa aacgcgccat atgagcccg tcgtgaattc ttctgagacc tgaagtgtag          60

<210> SEQ ID NO 24
<211> LENGTH: 26
<212> TYPE: DNA
<213> ORGANISM: Artificial Sequence
<220> FEATURE:
<223> OTHER INFORMATION: TSR example 6 Chromosome 21 unique site with
      BSAI

<400> SEQUENCE: 24
gtcacaaaaa gagaccctgt gtttaa                                               26

<210> SEQ ID NO 25
<211> LENGTH: 91
<212> TYPE: DNA
<213> ORGANISM: Artificial Sequence
<220> FEATURE:
<223> OTHER INFORMATION: SCP combines Example 1 SSR with TSR example 6
      Chromosome 21 unique site with BSAI

<400> SEQUENCE: 25
gctcggaccc tgctgtatcg ttcgcgggcc tcctcctcaa aaacgcgcca tatgagcccc          60
gtcgtgtcac aaaaagagac cctgtgttta a                                         91

<210> SEQ ID NO 26
<211> LENGTH: 60
<212> TYPE: DNA
<213> ORGANISM: Artificial Sequence
<220> FEATURE:
<223> OTHER INFORMATION: Partial SCP - Example 1 SSR with TSR example 6
      Chromosome 21 unique site with BSAI - after abasic site

<400> SEQUENCE: 26
cctcctcaaa aacgcgccat atgagcccg tcgtgtcaca aaaagagacc ctgtgtttaa          60

<210> SEQ ID NO 27
<211> LENGTH: 26
<212> TYPE: DNA
<213> ORGANISM: Artificial Sequence
<220> FEATURE:
<223> OTHER INFORMATION: TSR example 7 Chromosome 21 unique site with
      BSAI

<400> SEQUENCE: 27
agccaaaaaa gagacctttc aaccca                                               26

<210> SEQ ID NO 28
<211> LENGTH: 91
<212> TYPE: DNA
<213> ORGANISM: Artificial Sequence
<220> FEATURE:
<223> OTHER INFORMATION: SCP combines Example 1 SSR with TSR example 7
      Chromosome 21 unique site with BSAI -continued

```
<400> SEQUENCE: 28
gctcggaccc tgctgtatcg ttcgcgggcc tcctcctcaa aaacgcgcca tatgagcccc       60
gtcgtagcca aaaagagac ctttcaaccc a                                        91

<210> SEQ ID NO 29
<211> LENGTH: 60
<212> TYPE: DNA
<213> ORGANISM: Artificial Sequence
<220> FEATURE:
<223> OTHER INFORMATION: Partial SCP - Example 1 SSR with TSR example 7
      Chromosome 21 unique site with BSAI - after abasic site

<400> SEQUENCE: 29
cctcctcaaa aacgcgccat atgagccccg tcgtagccaa aaagagacc tttcaaccca        60

<210> SEQ ID NO 30
<211> LENGTH: 26
<212> TYPE: DNA
<213> ORGANISM: Artificial Sequence
<220> FEATURE:
<223> OTHER INFORMATION: TSR example 8 Chromosome 21 unique site with
      BSAI

<400> SEQUENCE: 30
agccccctaa gagaccaaaa tagcaa                                            26

<210> SEQ ID NO 31
<211> LENGTH: 91
<212> TYPE: DNA
<213> ORGANISM: Artificial Sequence
<220> FEATURE:
<223> OTHER INFORMATION: SCP combines Example 1 SSR with TSR example 8
      Chromosome 21 unique site with BSAI

<400> SEQUENCE: 31
gctcggaccc tgctgtatcg ttcgcgggcc tcctcctcaa aaacgcgcca tatgagcccc       60
gtcgtagccc cctaagagac caaaatagca a                                      91

<210> SEQ ID NO 32
<211> LENGTH: 60
<212> TYPE: DNA
<213> ORGANISM: Artificial Sequence
<220> FEATURE:
<223> OTHER INFORMATION: Partial SCP - Example 1 SSR with TSR example 8
      Chromosome 21 unique site with BSAI - after abasic site

<400> SEQUENCE: 32
cctcctcaaa aacgcgccat atgagccccg tcgtagcccc ctaagagacc aaaatagcaa       60

<210> SEQ ID NO 33
<211> LENGTH: 26
<212> TYPE: DNA
<213> ORGANISM: Artificial Sequence
<220> FEATURE:
<223> OTHER INFORMATION: TSR example 9 Chromosome 21 unique site with
      BSAI

<400> SEQUENCE: 33
aattataaat gagacctagg atgcag                                            26

<210> SEQ ID NO 34
<211> LENGTH: 91
<212> TYPE: DNA
<213> ORGANISM: Artificial Sequence
```

<220> FEATURE:
<223> OTHER INFORMATION: SCP combines Example 1 SSR with TSR example 9
     Chromosome 21 unique site with BSAI

<400> SEQUENCE: 34
gctcggaccc tgctgtatcg ttcgcgggcc tcctcctcaa aaacgcgcca tatgagcccc     60
gtcgtaatta taaatgagac ctaggatgca g                                    91

<210> SEQ ID NO 35
<211> LENGTH: 60
<212> TYPE: DNA
<213> ORGANISM: Artificial Sequence
<220> FEATURE:
<223> OTHER INFORMATION: Partial SCP - Example 1 SSR with TSR example 9
     Chromosome 21 unique site with BSAI - after abasic site

<400> SEQUENCE: 35
cctcctcaaa aacgcgccat atgagccccg tcgtaattat aaatgagacc taggatgcag     60

<210> SEQ ID NO 36
<211> LENGTH: 26
<212> TYPE: DNA
<213> ORGANISM: Artificial Sequence
<220> FEATURE:
<223> OTHER INFORMATION: TSR example 10 Chromosome 21 unique site with
     BSAI

<400> SEQUENCE: 36
tcaccctaaa gagaccaagg aagaat                                          26

<210> SEQ ID NO 37
<211> LENGTH: 91
<212> TYPE: DNA
<213> ORGANISM: Artificial Sequence
<220> FEATURE:
<223> OTHER INFORMATION: SCP combines Example 1 SSR with TSR example 10
     Chromosome 21 unique site with BSAI

<400> SEQUENCE: 37
gctcggaccc tgctgtatcg ttcgcgggcc tcctcctcaa aaacgcgcca tatgagcccc     60
gtcgttcacc ctaaagagac caaggaagaa t                                    91

<210> SEQ ID NO 38
<211> LENGTH: 60
<212> TYPE: DNA
<213> ORGANISM: Artificial Sequence
<220> FEATURE:
<223> OTHER INFORMATION: Partial SCP - Example 1 SSR with TSR example 10
     Chromosome 21 unique site with BSAI - after abasic site

<400> SEQUENCE: 38
cctcctcaaa aacgcgccat atgagccccg tcgttcaccc taaagagacc aaggaagaat     60

<210> SEQ ID NO 39
<211> LENGTH: 26
<212> TYPE: DNA
<213> ORGANISM: Artificial Sequence
<220> FEATURE:
<223> OTHER INFORMATION: TSR example 11 Chromosome 21 unique site with
     BSAI

<400> SEQUENCE: 39
tctaactaaa gagaccatta acgcaa                                          26

<210> SEQ ID NO 40

```
<211> LENGTH: 91
<212> TYPE: DNA
<213> ORGANISM: Artificial Sequence
<220> FEATURE:
<223> OTHER INFORMATION: SCP combines Example 1 SSR with TSR example 11
      Chromosome 21 unique site with BSAI

<400> SEQUENCE: 40
gctcggaccc tgctgtatcg ttcgcgggcc tcctcctcaa aaacgcgcca tatgagcccc      60
gtcgttctaa ctaaagagac cattaacgca a                                     91

<210> SEQ ID NO 41
<211> LENGTH: 60
<212> TYPE: DNA
<213> ORGANISM: Artificial Sequence
<220> FEATURE:
<223> OTHER INFORMATION: Partial SCP - Example 1 SSR with TSR example 11
      Chromosome 21 unique site with BSAI - after abasic site

<400> SEQUENCE: 41
cctcctcaaa aacgcgccat atgagccccg tcgttctaac taaagagacc attaacgcaa      60

<210> SEQ ID NO 42
<211> LENGTH: 27
<212> TYPE: DNA
<213> ORGANISM: Artificial Sequence
<220> FEATURE:
<223> OTHER INFORMATION: TSR example 12 Chromosome 21 unique site with
      BspQI

<400> SEQUENCE: 42
gtcccgagct gaagagcttt aaaacct                                          27

<210> SEQ ID NO 43
<211> LENGTH: 92
<212> TYPE: DNA
<213> ORGANISM: Artificial Sequence
<220> FEATURE:
<223> OTHER INFORMATION: SCP combines Example 1 SSR with TSR example 12
      Chromosome 21 unique site with BspQI

<400> SEQUENCE: 43
gctcggaccc tgctgtatcg ttcgcgggcc tcctcctcaa aaacgcgcca tatgagcccc      60
gtcgtgtccc gagctgaaga gctttaaaac ct                                    92

<210> SEQ ID NO 44
<211> LENGTH: 61
<212> TYPE: DNA
<213> ORGANISM: Artificial Sequence
<220> FEATURE:
<223> OTHER INFORMATION: Partial SCP - Example 1 SSR with TSR example 12
      Chromosome 21 unique site with BspQI - after abasic site

<400> SEQUENCE: 44
cctcctcaaa aacgcgccat atgagccccg tcgtgtcccg agctgaagag ctttaaaacc      60
t                                                                      61

<210> SEQ ID NO 45
<211> LENGTH: 27
<212> TYPE: DNA
<213> ORGANISM: Artificial Sequence
<220> FEATURE:
<223> OTHER INFORMATION: TSR example 13 Chromosome 21 unique site with
      BspQI

<400> SEQUENCE: 45
```

```
ccacctaact gaagagcgtt gggagcc                                              27

<210> SEQ ID NO 46
<211> LENGTH: 92
<212> TYPE: DNA
<213> ORGANISM: Artificial Sequence
<220> FEATURE:
<223> OTHER INFORMATION: SCP combines Example 1 SSR with TSR example 13
      Chromosome 21 unique site with BspQI

<400> SEQUENCE: 46
gctcggaccc tgctgtatcg ttcgcgggcc tcctcctcaa aaacgcgcca tatgagcccc        60
gtcgtccacc taactgaaga gcgttgggag cc                                       92

<210> SEQ ID NO 47
<211> LENGTH: 61
<212> TYPE: DNA
<213> ORGANISM: Artificial Sequence
<220> FEATURE:
<223> OTHER INFORMATION: Partial SCP - Example 1 SSR with TSR example 13
      Chromosome 21 unique site with BspQI - after abasic site

<400> SEQUENCE: 47
cctcctcaaa aacgcgccat atgagccccg tcgtccacct aactgaagag cgttgggagc        60
c                                                                          61

<210> SEQ ID NO 48
<211> LENGTH: 27
<212> TYPE: DNA
<213> ORGANISM: Artificial Sequence
<220> FEATURE:
<223> OTHER INFORMATION: TSR example 14 Chromosome 21 unique site with
      BspQI

<400> SEQUENCE: 48
ctttggtggt gaagagctgc caccaaa                                             27

<210> SEQ ID NO 49
<211> LENGTH: 92
<212> TYPE: DNA
<213> ORGANISM: Artificial Sequence
<220> FEATURE:
<223> OTHER INFORMATION: SCP combines Example 1 SSR with TSR example 14
      Chromosome 21 unique site with BspQI

<400> SEQUENCE: 49
gctcggaccc tgctgtatcg ttcgcgggcc tcctcctcaa aaacgcgcca tatgagcccc        60
gtcgtctttg gtggtgaaga gctgccacca aa                                       92

<210> SEQ ID NO 50
<211> LENGTH: 61
<212> TYPE: DNA
<213> ORGANISM: Artificial Sequence
<220> FEATURE:
<223> OTHER INFORMATION: Partial SCP - Example 1 SSR with TSR example 14
      Chromosome 21 unique site with BspQI - after abasic site

<400> SEQUENCE: 50
cctcctcaaa aacgcgccat atgagccccg tcgtctttgg tggtgaagag ctgccaccaa        60
a                                                                          61

<210> SEQ ID NO 51
<211> LENGTH: 27
```

-continued

```
<212> TYPE: DNA
<213> ORGANISM: Artificial Sequence
<220> FEATURE:
<223> OTHER INFORMATION: TSR example 15 Chromosome 21 unique site with
      BspQI

<400> SEQUENCE: 51
aagtggtctg gaagagccgg gggagtg                                          27

<210> SEQ ID NO 52
<211> LENGTH: 92
<212> TYPE: DNA
<213> ORGANISM: Artificial Sequence
<220> FEATURE:
<223> OTHER INFORMATION: SCP combines Example 1 SSR with TSR example 15
      Chromosome 21 unique site with BspQI

<400> SEQUENCE: 52
gctcggaccc tgctgtatcg ttcgcgggcc tcctcctcaa aaacgcgcca tatgagcccc      60
gtcgtaagtg gtctggaaga gccgggggag tg                                    92

<210> SEQ ID NO 53
<211> LENGTH: 61
<212> TYPE: DNA
<213> ORGANISM: Artificial Sequence
<220> FEATURE:
<223> OTHER INFORMATION: Partial SCP - Example 1 SSR with TSR example 15
      Chromosome 21 unique site with BspQI - after abasic site

<400> SEQUENCE: 53
cctcctcaaa aacgcgccat atgagccccg tcgtaagtgg tctggaagag ccggggggagt      60 g                                                                      61

<210> SEQ ID NO 54
<211> LENGTH: 27
<212> TYPE: DNA
<213> ORGANISM: Artificial Sequence
<220> FEATURE:
<223> OTHER INFORMATION: TSR example 16 Chromosome 21 unique site with
      BspQI

<400> SEQUENCE: 54
gtcacctaaa gaagagcctt caggaat                                          27

<210> SEQ ID NO 55
<211> LENGTH: 92
<212> TYPE: DNA
<213> ORGANISM: Artificial Sequence
<220> FEATURE:
<223> OTHER INFORMATION: SCP combines Example 1 SSR with TSR example 16
      Chromosome 21 unique site with BspQI

<400> SEQUENCE: 55
gctcggaccc tgctgtatcg ttcgcgggcc tcctcctcaa aaacgcgcca tatgagcccc      60
gtcgtgtcac ctaaagaaga gccttcagga at                                    92

<210> SEQ ID NO 56
<211> LENGTH: 61
<212> TYPE: DNA
<213> ORGANISM: Artificial Sequence
<220> FEATURE:
<223> OTHER INFORMATION: Partial SCP - Example 1 SSR with TSR example 16
      Chromosome 21 unique site with BspQI - after abasic site

<400> SEQUENCE: 56
```

-continued cctcctcaaa aacgcgccat atgagccccg tcgtgtcacc taaagaagag ccttcaggaa          60
t                                                                           61

<210> SEQ ID NO 57
<211> LENGTH: 27
<212> TYPE: DNA
<213> ORGANISM: Artificial Sequence
<220> FEATURE:
<223> OTHER INFORMATION: TSR example 17 Chromosome 21 unique site with
      BspQI

<400> SEQUENCE: 57
tctagattct gaagagccag aactcta                                              27

<210> SEQ ID NO 58
<211> LENGTH: 92
<212> TYPE: DNA
<213> ORGANISM: Artificial Sequence
<220> FEATURE:
<223> OTHER INFORMATION: SCP combines Example 1 SSR with TSR example 17
      Chromosome 21 unique site with BspQI

<400> SEQUENCE: 58
gctcggaccc tgctgtatcg ttcgcgggcc tcctcctcaa aaacgcgcca tatgagcccc          60
gtcgttctag attctgaaga gccagaactc ta                                        92

<210> SEQ ID NO 59
<211> LENGTH: 61
<212> TYPE: DNA
<213> ORGANISM: Artificial Sequence
<220> FEATURE:
<223> OTHER INFORMATION: Partial SCP - Example 1 SSR with TSR example 17
      Chromosome 21 unique site with BspQI - after abasic site

<400> SEQUENCE: 59
cctcctcaaa aacgcgccat atgagccccg tcgttctaga ttctgaagag ccagaactct          60
a                                                                           61

<210> SEQ ID NO 60
<211> LENGTH: 27
<212> TYPE: DNA
<213> ORGANISM: Artificial Sequence
<220> FEATURE:
<223> OTHER INFORMATION: TSR example 18 Chromosome 21 unique site with
      BspQI

<400> SEQUENCE: 60
cctggaactg gaagagccgt gtgttta                                              27

<210> SEQ ID NO 61
<211> LENGTH: 92
<212> TYPE: DNA
<213> ORGANISM: Artificial Sequence
<220> FEATURE:
<223> OTHER INFORMATION: SCP combines Example 1 SSR with TSR example 18
      Chromosome 21 unique site with BspQI

<400> SEQUENCE: 61
gctcggaccc tgctgtatcg ttcgcgggcc tcctcctcaa aaacgcgcca tatgagcccc          60
gtcgtcctgg aactggaaga gccgtgtgtt ta                                        92

<210> SEQ ID NO 62
<211> LENGTH: 61
<212> TYPE: DNA

<213> ORGANISM: Artificial Sequence
<220> FEATURE:
<223> OTHER INFORMATION: Partial SCP - Example 1 SSR with TSR example 18
      Chromosome 21 unique site with BspQI - after abasic site

<400> SEQUENCE: 62
cctcctcaaa aacgcgccat atgagccccg tcgtcctgga actggaagag ccgtgtgttt        60
a                                                                        61

<210> SEQ ID NO 63
<211> LENGTH: 27
<212> TYPE: DNA
<213> ORGANISM: Artificial Sequence
<220> FEATURE:
<223> OTHER INFORMATION: TSR example 19 Chromosome 21 unique site with
      BspQI

<400> SEQUENCE: 63
cccatttgtg gaagagcatg aaatggg                                            27

<210> SEQ ID NO 64
<211> LENGTH: 92
<212> TYPE: DNA
<213> ORGANISM: Artificial Sequence
<220> FEATURE:
<223> OTHER INFORMATION: SCP combines Example 1 SSR with TSR example 19
      Chromosome 21 unique site with BspQI

<400> SEQUENCE: 64
gctcggaccc tgctgtatcg ttcgcgggcc tcctcctcaa aaacgcgcca tatgagcccc        60
gtcgtcccat ttgtggaaga gcatgaaatg gg                                      92

<210> SEQ ID NO 65
<211> LENGTH: 61
<212> TYPE: DNA
<213> ORGANISM: Artificial Sequence
<220> FEATURE:
<223> OTHER INFORMATION: Partial SCP - Example 1 SSR with TSR example 19
      Chromosome 21 unique site with BspQI - after abasic site

<400> SEQUENCE: 65
cctcctcaaa aacgcgccat atgagccccg tcgtcccatt tgtggaagag catgaaatgg        60
g                                                                        61

<210> SEQ ID NO 66
<211> LENGTH: 27
<212> TYPE: DNA
<213> ORGANISM: Artificial Sequence
<220> FEATURE:
<223> OTHER INFORMATION: TSR example 20 Chromosome 21 unique site with
      BspQI

<400> SEQUENCE: 66
ccaggtctga gaagagcaca tttcatc                                            27

<210> SEQ ID NO 67
<211> LENGTH: 92
<212> TYPE: DNA
<213> ORGANISM: Artificial Sequence
<220> FEATURE:
<223> OTHER INFORMATION: SCP combines Example 1 SSR with TSR example 20
      Chromosome 21 unique site with BspQI

<400> SEQUENCE: 67
gctcggaccc tgctgtatcg ttcgcgggcc tcctcctcaa aaacgcgcca tatgagcccc        60
gtcgtccagg tctgagaaga gcacatttca tc                                        92

<210> SEQ ID NO 68
<211> LENGTH: 61
<212> TYPE: DNA
<213> ORGANISM: Artificial Sequence
<220> FEATURE:
<223> OTHER INFORMATION: Partial SCP - Example 1 SSR with TSR example 20
      Chromosome 21 unique site with BspQI - after abasic site

<400> SEQUENCE: 68
cctcctcaaa aacgcgccat atgagccccg tcgtccaggt ctgagaagag cacatttcat      60
c                                                                         61

<210> SEQ ID NO 69
<211> LENGTH: 27
<212> TYPE: DNA
<213> ORGANISM: Artificial Sequence
<220> FEATURE:
<223> OTHER INFORMATION: TSR example 21 Chromosome 21 unique site with
      BspQI

<400> SEQUENCE: 69
caggatgtga gaagagcctg gtgcata                                             27

<210> SEQ ID NO 70
<211> LENGTH: 92
<212> TYPE: DNA
<213> ORGANISM: Artificial Sequence
<220> FEATURE:
<223> OTHER INFORMATION: SCP combines Example 1 SSR with TSR example 21
      Chromosome 21 unique site with BspQI

<400> SEQUENCE: 70
gctcggaccc tgctgtatcg ttcgcgggcc tcctcctcaa aaacgcgcca tatgagcccc      60
gtcgtcagga tgtgagaaga gcctggtgca ta                                       92

<210> SEQ ID NO 71
<211> LENGTH: 61
<212> TYPE: DNA
<213> ORGANISM: Artificial Sequence
<220> FEATURE:
<223> OTHER INFORMATION: Partial SCP - Example 1 SSR with TSR example 21
      Chromosome 21 unique site with BspQI - after abasic site

<400> SEQUENCE: 71
cctcctcaaa aacgcgccat atgagccccg tcgtcaggat gtgagaagag cctggtgcat      60
a                                                                         61

<210> SEQ ID NO 72
<211> LENGTH: 27
<212> TYPE: DNA
<213> ORGANISM: Artificial Sequence
<220> FEATURE:
<223> OTHER INFORMATION: TSR example 22 Chromosome 21 unique site with
      BspQI

<400> SEQUENCE: 72
taaaccattg gaagagcttg tgctctg                                             27

<210> SEQ ID NO 73
<211> LENGTH: 92
<212> TYPE: DNA
<213> ORGANISM: Artificial Sequence

```
<220> FEATURE:
<223> OTHER INFORMATION: SCP combines Example 1 SSR with TSR example 22
      Chromosome 21 unique site with BspQI

<400> SEQUENCE: 73
gctcggaccc tgctgtatcg ttcgcgggcc tcctcctcaa aaacgcgcca tatgagcccc      60
gtcgttaaac cattggaaga gcttgtgctc tg                                    92

<210> SEQ ID NO 74
<211> LENGTH: 61
<212> TYPE: DNA
<213> ORGANISM: Artificial Sequence
<220> FEATURE:
<223> OTHER INFORMATION: Partial SCP - Example 1 SSR with TSR example 22
      Chromosome 21 unique site with BspQI - after abasic site

<400> SEQUENCE: 74
cctcctcaaa aacgcgccat atgagccccg tcgttaaacc attggaagag cttgtgctct      60
g                                                                      61

<210> SEQ ID NO 75
<211> LENGTH: 21
<212> TYPE: DNA
<213> ORGANISM: Artificial Sequence
<220> FEATURE:
<223> OTHER INFORMATION: TSR example 23 Chromosome 21 unique site with
      BspQI

<400> SEQUENCE: 75
tgtggaagag catgaaatgg g                                                 21

<210> SEQ ID NO 76
<211> LENGTH: 92
<212> TYPE: DNA
<213> ORGANISM: Artificial Sequence
<220> FEATURE:
<223> OTHER INFORMATION: SCP combines Example 1 SSR with TSR example 23
      Chromosome 21 unique site with BspQI

<400> SEQUENCE: 76
gctcggaccc tgctgtatcg ttcgcgggcc tcctcctcaa aaacgcgcca tatgagcccc      60
gtcgtcccat ttgtggaaga gcatgaaatg gg                                    92

<210> SEQ ID NO 77
<211> LENGTH: 61
<212> TYPE: DNA
<213> ORGANISM: Artificial Sequence
<220> FEATURE:
<223> OTHER INFORMATION: Partial SCP - Example 1 SSR with TSR example 23
      Chromosome 21 unique site with BspQI - after abasic site

<400> SEQUENCE: 77
cctcctcaaa aacgcgccat atgagccccg tcgtcccatt gtggaagag catgaaatgg       60 g                                                                      61

<210> SEQ ID NO 78
<211> LENGTH: 43
<212> TYPE: DNA
<213> ORGANISM: Artificial Sequence
<220> FEATURE:
<223> OTHER INFORMATION: Partial SCP - Example 3 partial SSR region
      before abasic site

<400> SEQUENCE: 78
```

-continued

```
gagccccgtc gtgctcggac cctgctgtat cgttcgcggg cct                         43

<210> SEQ ID NO 79
<211> LENGTH: 30
<212> TYPE: DNA
<213> ORGANISM: Artificial Sequence
<220> FEATURE:
<223> OTHER INFORMATION: Partial SCP - Example 3 partial SSR region
      after abasic site

<400> SEQUENCE: 79
cctcctcaaa aacgcgccat atgtcagaat                                        30

<210> SEQ ID NO 80
<211> LENGTH: 51
<212> TYPE: DNA
<213> ORGANISM: Artificial Sequence
<220> FEATURE:
<223> OTHER INFORMATION: Partial SCP - Example 19 TSR with partial SSR
      region after abasic site

<400> SEQUENCE: 80
cctcctcaaa aacgcgccat atgtcagaat tgtggaagag catgaaatgg g               51

<210> SEQ ID NO 81
<211> LENGTH: 25
<212> TYPE: DNA
<213> ORGANISM: Artificial Sequence
<220> FEATURE:
<223> OTHER INFORMATION: Lock Probe Example 1

<400> SEQUENCE: 81
gagccccgtc gtgctcggac cctgc                                            25

<210> SEQ ID NO 82
<211> LENGTH: 31
<212> TYPE: DNA
<213> ORGANISM: Artificial Sequence
<220> FEATURE:
<223> OTHER INFORMATION: Lock Probe Example 2

<400> SEQUENCE: 82
gagccccgtc gtcccattgc tcggaccctg c                                     31

<210> SEQ ID NO 83
<211> LENGTH: 99
<212> TYPE: DNA
<213> ORGANISM: Artificial Sequence
<220> FEATURE:
<223> OTHER INFORMATION: SCR0083 (iSpc3 i.e. internal 3 carbon propane
      diol spacers, which serve as extension blockers may also present)

<400> SEQUENCE: 83
gctcggaccc tgctgtatcg ttcgcgggcc tcctcctcaa aaacgcgcca tatgagcccc      60
gtcgtgatta cccgctgatg gtgaagagct gccaccaaa                             99

<210> SEQ ID NO 84
<211> LENGTH: 21
<212> TYPE: DNA
<213> ORGANISM: Artificial Sequence
<220> FEATURE:
<223> OTHER INFORMATION: SCR0113

<400> SEQUENCE: 84
tttggtggca gctcttcacc a                                                21
```

```
<210> SEQ ID NO 85
<211> LENGTH: 24
<212> TYPE: DNA
<213> ORGANISM: Artificial Sequence
<220> FEATURE:
<223> OTHER INFORMATION: SCR0080

<400> SEQUENCE: 85
cagggtccga gctcagcggg taat                                              24

<210> SEQ ID NO 86
<211> LENGTH: 15
<212> TYPE: DNA
<213> ORGANISM: Artificial Sequence
<220> FEATURE:
<223> OTHER INFORMATION: SSR1_FP

<400> SEQUENCE: 86
cctcaaaaac gcgcc                                                        15

<210> SEQ ID NO 87
<211> LENGTH: 18
<212> TYPE: DNA
<213> ORGANISM: Artificial Sequence
<220> FEATURE:
<223> OTHER INFORMATION: SSR1_RP

<400> SEQUENCE: 87
aggcccgcga acgataca                                                     18

<210> SEQ ID NO 88
<211> LENGTH: 22
<212> TYPE: DNA
<213> ORGANISM: Artificial Sequence
<220> FEATURE:
<223> OTHER INFORMATION: SCR0078 (Reporter i.e. FAM and Quencher i.e.
      ZEN and Iowa Black)

<400> SEQUENCE: 88
tcagcgggta atcacggggc tc                                                22

<210> SEQ ID NO 89
<211> LENGTH: 78
<212> TYPE: DNA
<213> ORGANISM: Artificial Sequence
<220> FEATURE:
<223> OTHER INFORMATION: SCR0076

<400> SEQUENCE: 89
cctcctcaaa aacgcgccat atgagccccg tcgtgattac ccgctgagct cggaccctgc       60
tgtatcgttc gcgggcct                                                     78

<210> SEQ ID NO 90
<211> LENGTH: 78
<212> TYPE: DNA
<213> ORGANISM: Artificial Sequence
<220> FEATURE:
<223> OTHER INFORMATION: SCR0136

<400> SEQUENCE: 90
cctcctcaaa aacgcgccat ataacgggcg gacggcgtag ttctgctgct cggaccctgc       60
tgtatcgttc gcgggcct                                                     78

<210> SEQ ID NO 91
```

```
<211> LENGTH: 25
<212> TYPE: DNA
<213> ORGANISM: Artificial Sequence
<220> FEATURE:
<223> OTHER INFORMATION: SCR0134 (Reporter i.e. HEX and Quencher i.e.
      ZENQ and Iowa Black)

<400> SEQUENCE: 91
agcagaacta cgccgtccgc ccgtt                                      25

<210> SEQ ID NO 92
<211> LENGTH: 99
<212> TYPE: DNA
<213> ORGANISM: Artificial Sequence
<220> FEATURE:
<223> OTHER INFORMATION: iSpc3 i.e. internal 3 carbon propane diol
      spacers, which serve as extension blockers may also present

<400> SEQUENCE: 92
gctcggaccc tgctgtatcg ttcgcgggcc tcctcctcaa aaacgcgcca tataacgggc   60
ggacggcgta gttctgctaa gagaagagca aaaacccta                         99

<210> SEQ ID NO 93
<211> LENGTH: 24
<212> TYPE: DNA
<213> ORGANISM: Artificial Sequence
<220> FEATURE:
<223> OTHER INFORMATION: SCR0135

<400> SEQUENCE: 93
cagggtccga gcagcagaac tacg                                       24

<210> SEQ ID NO 94
<211> LENGTH: 25
<212> TYPE: DNA
<213> ORGANISM: Artificial Sequence
<220> FEATURE:
<223> OTHER INFORMATION: Reporter i.e. HEX and Quencher i.e. ZENQ and
      Iowa Black

<400> SEQUENCE: 94
agcagaacta cgccgtccgc ccgtt                                      25

<210> SEQ ID NO 95
<211> LENGTH: 18
<212> TYPE: DNA
<213> ORGANISM: Artificial Sequence
<220> FEATURE:
<223> OTHER INFORMATION: SCR0142

<400> SEQUENCE: 95
tgtatcgttc gcgggcct                                              18

<210> SEQ ID NO 96
<211> LENGTH: 18
<212> TYPE: DNA
<213> ORGANISM: Artificial Sequence
<220> FEATURE:
<223> OTHER INFORMATION: SCR0142a

<400> SEQUENCE: 96
tgtatcgttc gcgggcct                                              18

<210> SEQ ID NO 97
<211> LENGTH: 47
<212> TYPE: DNA
```

-continued

```
<213> ORGANISM: Artificial Sequence
<220> FEATURE:
<223> OTHER INFORMATION: SCR0146

<400> SEQUENCE: 97
cctcctcaaa aacgcgccat atgagccccg tcgtgattac ccgctga               47

<210> SEQ ID NO 98
<211> LENGTH: 22
<212> TYPE: DNA
<213> ORGANISM: Artificial Sequence
<220> FEATURE:
<223> OTHER INFORMATION: SCR0147

<400> SEQUENCE: 98
gcgaacgata catcagcggg ta                                          22

<210> SEQ ID NO 99
<211> LENGTH: 99
<212> TYPE: DNA
<213> ORGANISM: Artificial Sequence
<220> FEATURE:
<223> OTHER INFORMATION: SCR0133 (iSpc3 i.e. internal 3 carbon propane
      diol spacers, which serve as extension blockers may also present)

<400> SEQUENCE: 99
gctcggaccc tgctgtatcg ttcgcgggcc tcctcctcaa aaacgcgcca tataacgggc     60
ggacggcgta gttctgctaa gagaagagca aaaaccta                            99
```

SEQUENCE CONVERSION REACTION

CROSS REFERENCE TO RELATED APPLICATIONS

This patent application is a U.S. national phase application under 35 U.S.C. 371 of International Patent Application No. PCT/US2021/036766, titled "SEQUENCE CONVERSION REACTION," filed on Jun. 10, 2021 now International Patent Publication No. WO2021/252733, which claims priority to U.S. provisional patent application No. 63/037,575, titled "SEQUENCE CONVERSION REACTION," and filed on Jun. 10, 2020, and to U.S. provisional patent application No. 63/166,955, titled "SEQUENCE CONVERSION REACTION," filed on Mar. 26, 2021, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure relates to compositions, kits, and methods for detecting and quantifying molecular targets, and especially for detecting and quantifying DNA and RNA. The apparatuses and methods may find use in a variety of applications including prenatal testing, detection of pathogens and screening of cancer.

BACKGROUND

There is a need for genetic assays that provide highly accurate and reproducible results. However, these highly reproducible results are difficult to achieve, when the amount of starting genetic material may be low in quantity and/or quality. As an example the theoretically required dPCR partitions proposed by Evans et al is about 220,000 to reliably detect trisomy with a 99% detection rate and a 1% false-positive rate at 2% fetal fraction. Attempts to achieve this number by dPCR have failed so far, because the mother's blood has on average only 1000 genome copies of cell free DNA (cfDNA) per 1-2 mL of plasma. It would therefore require to detect about 200 alleles each on chromosomes 13, 18 and 21. In such a scenario 1800 oligonucleotides would be required and for a number of technical reasons this is not practical. It is therefore desirable to reduce the complexity of such assays to make dPCR a useful tools for NIPT. Such reduced complexity assays would be particularly useful for genetic screening. Such assays may be useful not only for prenatal testing, including in particular non-invasive prenatal testing, but also pathogen, cancer screening and other applications.

Non-invasive prenatal testing refers to testing the characteristics of a fetus from a pregnant female, from a tissue sample obtained from the pregnant female. Fetal cells and parts of fetal cells including fetal nucleic acid are present in the pregnant female's bloodstream and the fetal tissue can provide a wealth of information. A blood sample can be easily and safely obtained from the pregnant female with no harm to the fetus. Advances in DNA amplification techniques such as polymerase chain reaction (PCR) and next generation sequencing (NGS) have led to substantial increases in our ability to perform prenatal testing and several prenatal tests are commercially available. Existing DNA amplification techniques, like dPCR, have various technical limitations such as nonspecific and biased amplification when trying to detect many different target sequences. These limitations can lead to results that cannot be interpreted. Next generation Sequences (NGS) techniques provide technical advantages but suffer from complex workflows associated with high cost and long turnaround time. Accordingly, there is a need for improved methods for performing these and other tests. In particular it would be desirable to enable dPCR for these tests due to low cost, fast turnaround time and relative ease of use especially compared to NGS.

Since the discovery of cell-free fetal DNA (cffDNA) in maternal plasma there has been rapid progress in harnessing this as a source of fetal genetic material for prenatal diagnosis. The majority of cell-free DNA (cfDNA) is maternal in origin, with the fetal proportion emanating from the placenta detectable in the maternal circulation from around 9 weeks after gestation and constituting around only 10% of cfDNA in early pregnancy. However, as cffDNA is cleared rapidly from the maternal circulation after delivery, it offers great potential as a source of fetal genetic material for prenatal diagnosis. Technological advances associated with the development of next-generation sequencing (NGS) have enabled accurate counting of DNA sequences that are associated with specific chromosomes present in maternal blood, which has allowed very rapid development of non-invasive prenatal testing (NIPT) for aneuploidy. Between 2011 and 2017 99.7% of all NIPT samples in published studies were run on Illumina NGS Systems, albeit for a while alternative approaches have been proposed. A method based on rolling circle amplification and counting of fluorescent objects was first commercialized in 2018.

The reliability of a quantitative measurement improves with the number of measurements (replicates). Often there is not enough material available to yield the number of measurements (copy number too low) needed to achieve the required accuracy and precision. For example, as mentioned before and as applicable to NIPT, the number of genomes (number of chromosome copies, number of allele copies) represented in 1-2 ml of plasma as cell-free DNA (cfDNA) is estimated to be approximately 1000 copies. This is (for example) not sufficient for NIPT by dPCR. Prior work has utilized hundreds of thousands of counts, using an alternative technology, to achieve the required performance.

Digital polymerase chain reaction (dPCR) is a biotechnological refinement of conventional PCR methods that can be used to directly quantify and clonally amplify nucleic acids strands including DNA, cDNA or RNA. In dPCR the sample is separated into a large number of partitions (e.g. droplets, microfluidic chambers, etc.) and the reaction is carried out in each partition individually. This separation allows absolute quantification without the need for a standard curve. The main technical reason why dPCR is not commonly used in NIPT despite the listed theoretical advantages and years of development are problems with the fact that the copy number of cfDNA is too low to deliver the required statistical precision. Theoretically, one can perform multiplexed dPCR, amplifying many alleles on chromosomes of interest in order to address the inherent low copy number issue. However, primer—primer—probe interactions in multiplexed dPCR causes unspecific and biased amplification, manifesting as a visible phenomenon called "rain", a form of background noise in dPCR. This problem is in particular pronounced in challenging samples. Diagnostic tests require high robustness, and the assumption has to be that samples are challenging. PCR amplifies target exponentially and small differences in reaction efficiency lead to very different copy numbers at the end of the reaction (e.g. 40 plus cycles) even when the copy number at the beginning of the reaction was the same.

Even though digital PCR is a digital yes/no reaction, the data analysis ultimately depends on a positive reaction i.e. TaqMan signal above background. This in turn depends on having enough TaqMan probe cleaved for a partition to be considered positive, which depends on how much amplicon was made by the end of cycling. Having different PCR efficiencies in different partitions may result in different amounts of amplicon in different partitions and hence in some partitions less cut probe compared to others (lower signal). This may lead to "rain" and the difficulty to clearly distinguish positive from negative.

Furthermore, cfDNA fragments of typically less than 300 base pairs in length may be distributed into individual partitions, with hundreds or thousands of potential target sequences (measurands) from a given chromosome. In order to examine in a clinically relevant manner multiple (e.g., three or more) chromosomes the assay needs to be able to potentially amplify many e.g. 100 different allele sites (measurands) per chromosome. This means that, in this example, each partition may need enough of each of the 300 primer pairs (600 primers) and 300 different probes to support detection of each measurand. There has to be enough primer and probe in each partition to support the reaction of a single target measurand, while at the same time the unused primer and probes need to be present but not interfere with a single target measurand (unique sequence) or cause a false positive result. In practical terms such a reaction cannot be performed reliably. It would be beneficial to reduce the complexity of the reaction and provide reliable target detection and quantitation.

SUMMARY OF THE DISCLOSURE

Described herein are methods, kits, and compositions that may address the limitations and needs described above. In particular, described herein are methods, including sequence conversion methods, which may be referred to as sequence conversion assays or sequence conversion reactions. As used herein, a sequence conversion method may convert one (or more preferentially more) target region, e.g., a target measurand or allele, into a signal specific region (SSR) that is engineered to include a polynucleotide marker region ("engineered polynucleotide marker") and in some cases primer regions for copying and/or amplifying and/or detecting the engineered polynucleotide marker. A number of different target regions, which may share a common property, such as being part of a particular chromosome, gene, plasmid, genetic pathway, or the like, may share a common signal specific region, by linking the same signal specific region to these different target measurand regions ("target-specific regions" or TSR) in a subset of sequence conversion probes (SCPs). Multiple subsets of sequence conversion probes may then be combined. This may also allow reduction in the complexity and variability of the assay to provide substantial advantages in sensitivity, accuracy and precision.

In general, these methods include detection of a natural occurring nucleic acid sequence by amplifying and detecting a synthetic sequence that is different from the original sequence.

These assays may therefore allow the parallel processing of large amounts of genetic material. Furthermore, the methods and compositions (including kits) described herein may allow the sequence conversion probes to be used with either or both DNA and RNA including very small, previously difficult to assay, fragments of RNA and/or DNA. The sequence conversion methods described herein may, with great fidelity, convert target measurands (or multiple target measurands) to signal specific regions (e.g., engineered polynucleotide markers) that may be directly assayed, e.g., by binding to one or more signal probes or signal labels, and/or by genetic amplification and detection (e.g., digital PCR, etc.).

For example, described herein are methods including: combining a plurality of sequence conversion probes (SCPs) with a sample mixture including one or more target measurand, wherein each SCP comprises a polynucleotide target-specific region (TSR), an affinity tag, and a signal specific region (SSR), the SSR comprising a first engineered polynucleotide region (which may be referred to herein as a marker, and may be recognized by one or more specific primers), further wherein the plurality of SCPs include different TSRs; hybridizing the TSRs of the SCPs to the one or more target measurand; cutting SCPs having TSRs that are hybridized to the one or more target measurands to release cut SSRs (cSSRs) without releasing SSRs of un-hybridized SCPs, wherein the cSSRs do not include the affinity tag; isolating the cSSRs from un-hybridized SCPs and the hybridized TSRs; and detecting the first engineered polynucleotide marker from the cSSRs.

A method may include: combining a plurality of sequence conversion probes (SCPs) with a sample mixture including one or more target measurand, wherein each SCP comprises a polynucleotide target-specific region (TSR) between an affinity tag and a signal specific region (SSR) comprising a first engineered polynucleotide marker and one or more primer regions, further wherein the plurality of SCPs comprises a plurality of different TSRs configured to hybridize to different target measurands and the same SSR; hybridizing the TSRs of the SCPs to the one or more target measurand; cutting SCPs having TSRs that are hybridized to the one or more target measurands to release cut SSRs (cSSRs) without releasing SSRs of un-hybridized SCPs; isolating the cSSRs from un-hybridized SCPs and the hybridized TSRs; and detecting the first engineered polynucleotide marker from the cSSRs.

In some variations, a method may include: combining a plurality of sequence conversion probes (SCPs) with a sample mixture including one or more target measurand, wherein each SCP comprises a polynucleotide target-specific region (TSR) between an affinity tag and a signal specific region (SSR) comprising a first engineered polynucleotide marker between a first forward primer region and a first reverse primer region, further wherein the plurality of SCPs comprises a plurality of different TSRs configured to hybridize to different target measurands, and each SCP of the plurality of SCPs comprises the same first forward primer region and first reverse primer region; hybridizing the TSRs of the SCPs to the one or more target measurand; cutting SCPs having TSRs that are hybridized to the one or more target measurands to release cut SSRs (cSSRs) without releasing SSRs of un-hybridized SCPs; isolating the cSSRs from un-hybridized SCPs and from the hybridized TSRs; and detecting the first engineered polynucleotide marker from the cSSRs. As described elsewhere, the primer regions (e.g., the first forward primer region and first reverse primer region) are also engineered, in addition to the engineered polynucleotide marker. In some variations the engineered polynucleotide marker may include one or more (including the first forward and first reverse) primer regions.

A method may include: combining a plurality of sequence conversion probes (SCPs) with a sample mixture including one or more target measurand, wherein each SCP comprises a polynucleotide target-specific region (TSR) between an affinity tag and a signal specific region (SSR) comprising a first engineered polynucleotide marker between a first forward primer region and a first reverse primer region, further wherein the plurality of SCPs comprises a plurality of different TSRs configured to hybridize to different target measurands, wherein at least some of the SCPs of the plurality of SCPs have different first forward primer regions and first reverse primer regions, wherein there are fewer different first forward primer regions and first reverse primer regions than there are different TSRs; hybridizing the TSRs of the SCPs to the one or more target measurand; cutting SCPs having TSRs that are hybridized to the one or more target measurands to release cut SSRs (cSSRs) without releasing SSRs of un-hybridized SCPs; isolating the cSSRs from un-hybridized SCPs and from the hybridized TSRs; and detecting the first engineered polynucleotide marker from the cSSRs In some variations the one or more primer regions may comprise a first forward primer region and a first reverse primer region, wherein the first engineered polynucleotide marker is flanked by the first forward primer region and the second forward primer region.

The plurality of SCPs may comprise a plurality of different one or more primer regions so that a sequence of the one or more primer regions of different SCPs have different sequences. In some variations the one or more primer regions have the same sequences (e.g. a forward primer and a reverse primer). The primers may be specific to each different engineered polynucleotide marker (and may be part of the engineered polynucleotide marker or separate from it).

In general, the signal specific region (SSR) (e.g., the engineered polynucleotide marker) may be designed to be approximately the same size, GC content, etc. between different signal specific regions so that they will be amplified with approximately the same frequency and/or efficiency, to prevent bias in the detection and/or measurements.

In any of the methods described herein, the cut SSRs (cSSRs) may be isolated from the un-cut (e.g., full length SCPs). For example, isolating the cSSRs may comprise using the affinity tag to separate the un-hybridized SCPs and the hybridized TSRs from the cSSRs.

In general, the sample mixture may be a biological sample or extracted from a biological sample. For example, the sample mixture may be blood or an extract of blood or any other bodily fluid and/or tissue. For example, as described herein in some variations the sample mixture is a blood sample taken from a pregnant woman that includes both maternal and fetal genetic material.

In some variations the TSR may be between the affinity tag and the SSR on each SCP. As mentioned, any appropriate target measurand may be used. For example, the one or more target measurand may be a DNA or an RNA. For example, the one or more target measurand may be an mRNA, a micro-RNA, an rRNA, an snRNA, or an RNAi, snoRNA, a guide RNA, a ribonuclease, a Y RNA, a telomerase RNA component, an antisense RNA (aRNA), a CRISPR RNA, a long noncoding RNA, a Piwi-interacting RNA, a small interfering RNA, a short hairpin RNA, a trans-acting siRNA, a repeat associated siRNA, an enhancer RNA, viral RNA, satellite RNA, genomic DNA, cfDNA, circulating tumor DNA, cell free fetal DNA (cffDNA), cell free maternal DNA, single stranded DNA (ssDNA), etc.

The target-specific region (TSR) of the sequence conversion probe (SCP) may be any appropriate length. For example, the TSR may be between about 13 and 100 bp long, e.g., between about 13-50 bp, between about 13-45 bp, between about 13-40 bp, between about 13-35 bp long, between about 13-30 bp long, etc. (e.g., between about 14-80 bp, between about 15-80 bp, etc.). In some variations, the TSR may be configured to hybridize to the one or more target measurand with 3 or fewer mismatches (e.g., with 2 or fewer mismatches, with 1 or fewer mismatches, etc.). The TSR is typically selected so that it represents a region of the genome that is unique to greater than 80%, meaning that the target-specific region does not share 80% or more identity with any other region in the genome of the target organism (e.g., the human genome). The TSR is selected as described herein so that it will hybridize to only a single (target) region of the genome. The methods and compositions described herein may, however, allow for individual variations (e.g., polymorphisms) that may be present between individuals while still only hybridizing to the specified (unique) target region. For example, the methods described herein may allow hybridizing of the region with 80% or greater identity. Because the TSR is selected to be a region that is unique in the target genome up to 80% identity (allowing some variation/polymorphisms), the TSR may be used to identify target regions that are 80% or more (e.g., 81% or more, 82% or more, 83% or more, 84% or more, 85% or more, 86% or more, 87% or more, 88% or more, 89% or more, 90% or more, 95% or more, etc.) identity.

The sequence conversion probe (SCP) may include any appropriate affinity tag. The affinity tag may be on the target-specific region, e.g., opposite from the signal specific region (SSR) of the SCP. In some variations the affinity tag is on the distal end of the TSR (e.g., opposite from the SSR, which may be either a 5' or 3' end). Although many of the examples described herein include biotin as the affinity tag (which may bind to a streptavidin group), any other affinity tag that may allow specific and secure binding between the affinity tag and the affinity partner may be used. For example, the affinity tag may be one or more of: a peptide tag or epitope tag or polynucleotide tag. Non-limiting examples of affinity tags may include: Albumin-binding protein (ABP), Alkaline Phosphatase (AP), AU1 epitope, AU5 epitope, Bacteriophage T7 epitope (T7-tag), Bacteriophage V5 epitope (V5-tag), Biotin-carboxy carrier protein (BCCP), Bluetongue virus tag (B-tag), Calmodulin binding peptide (CBP), Chloramphenicol Acetyl Transferase (CAT), Cellulose binding domain (CBP), Chitin binding domain (CBD), Choline-binding domain (CBD), Dihydrofolate reductase (DHFR), E2 epitope, FLAG epitope, Galactose-binding protein (GBP), Green fluorescent protein (GFP), Glu-Glu (EE-tag), Glutathione S-transferase (GST), Human influenza hemagglutinin (HA), HaloTag®, Histidine affinity tag (HAT), Horseradish Peroxidase (HRP), HSV epitope, Ketosteroid isomerase (KSI), KT3 epitope, LacZ, Luciferase, Maltose-binding protein (MBP), Myc epitope, NusA, PDZ domain, PDZ ligand, Polyarginine (Arg-tag), Polyaspartate (Asp-tag), Polycysteine (Cys-tag), Polyhistidine (His-tag), Polyphenylalanine (Phe-tag), Profinity eXact, Protein C, S1-tag, S-tag, Streptavadin-binding peptide (SBP), Staphylococcal protein A (Protein A), Staphylococcal protein G (Protein G), Strep-tag, Streptavadin, Small Ubiquitin-like Modifier (SUMO), Tandem Affinity Purification (TAP), T7 epitope, Thioredoxin (Trx), TrpE, Ubiquitin, Universal, VSV-G, etc.

As mentioned, any of these methods may include cutting the SCPs that are hybridized to the one or more target measurands with a nuclease. Any appropriate nuclease may be used. For example, the nuclease may be one or more of: a flap endonuclease/5' nuclease, a double-strand nuclease, an RNA specific nuclease, a CAS. In some variations, the nuclease may comprise one of: an RNase H, a duplex-specific nuclease (DSN) (e.g. Evrogen cat #EA 001), a double-stranded DNase (dsDNase), and a restriction endonuclease. For example, the nuclease may be RNase H2. The one or more target measurand may be an RNA, and the first engineered polynucleotide marker may comprise a DNA.

In general, the cut signal specific region (cSSR) may be isolated from the non-cut SCP (including non-cut SCP's own SSR) by binding the affinity tag to a substrate to remove the un-hybridized SCPs and the hybridized TSRs. In some variations the substrate is a solid phase substrate, such as, e.g., a magnetic bead or microwell titer plate.

Any of the sequence conversion probes may include one or more predetermined cutting or cleavage regions, e.g., between the SSR and the TSR (and/or part of the TSR). In some variations, particularly those using a RNase H2, for example, the SCP may include one or more ribose configured to serve as a cleavage site for cutting the SCPs having TSRs that are hybridized to the one or more target measurands.

In any of these methods, detecting the first engineered polynucleotide marker from the cSSRs may include amplifying the first engineered polynucleotide marker using one or more primers specific to the SSR.

As mentioned, the cut signal specific region may be detected specifically and effectively by one or more techniques described herein. For example, the SSR (and particularly the engineered polynucleotide marker) may be detected by amplifying the first engineered polynucleotide marker using a primer configured to hybridize to the first forward primer region and a primer configured to hybridize to the first reverse primer region. For example, detecting may include detecting the first engineered polynucleotide marker from the cSSRs by amplifying the first engineered polynucleotide marker using primers configured to hybridize to the different first forward primer regions and primers configured to hybridize to the first reverse primer regions. Alternatively or additionally, detecting the first engineered polynucleotide marker may include hybridizing the cSSR to a labeled signal probe and detecting a signal from the labeled signal probe. As described in greater detail herein, in some variations, the SSRs described herein may include only one primer region (and not a pair); for example, isothermal amplification and RCA with one primer may be used.

Detecting the first engineered polynucleotide marker may include hybridizing the cSSR to a labeled signal probe and to a capture probe and detecting a signal from the labeled signal probe.

Also described herein are kits to perform any of the methods described herein. For example a kit may include a first plurality of sequence conversion probes (SCPs) directed against a plurality of target measurands, wherein each SCP comprises a polynucleotide target-specific region (TSR) configured to hybridize with one target measurand of the plurality of target measurands, wherein the TSR is between an affinity tag and a signal specific region (SSR), the SSR comprising a first engineered polynucleotide marker; a nuclease configured to cut SCPs having TSRs that are hybridized to target measurand; and a substrate comprising a binding partner that specifically binds to the affinity tag.

In some variations a kit includes: a first plurality of sequence conversion probes (SCPs) directed against a plurality of target measurands, wherein each SCP comprises a polynucleotide target-specific region (TSR) configured to hybridize with one target measurand of the plurality of target measurands, wherein the TSR is between an affinity tag and a signal specific region (SSR), the SSR comprising a first engineered polynucleotide marker; a nuclease configured to cut SCPs having TSRs that are hybridized to target measurand; and a substrate comprising a binding partner that specifically binds to the affinity tag.

For example, a kit may include: a first plurality of sequence conversion probes (SCPs) directed against a first plurality of target measurands, wherein each SCP comprises: a polynucleotide target-specific region (TSR) configured to hybridize with one target measurand of the first plurality of target measurands, and wherein the TSR is between an affinity tag and a signal specific region (SSR), the SSR comprising a first engineered polynucleotide marker between a first forward primer region and a first reverse primer region; a nuclease configured to cut SCPs having TSRs that are hybridized to target measurand; a first forward primer configured to hybridize to the first forward primer region and a first reverse primer configured to hybridize to the first reverse primer region; and a substrate comprising a binding partner that specifically binds to the affinity tag.

The plurality of SCPs may comprise a plurality of different first forward primer regions and first reverse primer regions, further wherein there are substantially fewer different first forward primer regions and first reverse primer regions than there are different TSRs. The plurality of SCPs may comprise a same first forward primer region and first reverse primer region.

Any of these kits may include a first forward primer configured to hybridize to the first forward primer region and a first reverse primer configured to hybridize to the first reverse primer region. In some variations, the kit may include one or more additional pluralities of sequence conversion probes (SCPs) directed against one or more additional pluralities of target measurands that are different from the first plurality of target measurands and different from each other, wherein each SCP of the one or more additional plurality of SCPs comprises: a polynucleotide target-specific region (TSR) configured to hybridize with one target measurand of the one or more additional pluralities of target measurands, and wherein the TSR is between the affinity tag and a second signal specific region (sSSR), wherein each of the one or more additional pluralities has a different sSSR comprising a second engineered polynucleotide marker between a second forward primer region and a second reverse primer region, wherein for each of the one or more additional pluralities the second forward primer region is the same or different from the first forward primer region and the second reverse primer region is the same or different from the second forward primer region. Each of the one or more the pluralities of SCPs may comprise a plurality of different second forward primer regions and second reverse primer regions, further wherein there substantially fewer different second forward primer regions and second reverse primer regions than there are different TSRs. A second forward primer may be configured to hybridize to the second forward primer region and a second reverse primer configured to hybridize to the second reverse primer region.

In some variations of the kit, the SCPs comprise at least one ribose configured to serve as a cutting site for the nuclease. Any of these kits may include a capture probe configured to hybridize to the engineered polynucleotide marker and a capture probe configured to hybridize to the engineered polynucleotide marker or a complex of the capture probe and the engineered polynucleotide marker. Any of these kits may include a nucleic acid amplification master mix.

Also described herein are applications of the sequence conversion methods described. For example, described herein are methods of nucleic acid amplification. For example, a method may include: combining a plurality of sets of sequence conversion probes (SCPs) with a sample mixture including a plurality of target measurands, wherein each set of SCPs comprises a plurality of SCPs, wherein each SCP includes: a polynucleotide target-specific region (TSR), an affinity tag and a signal specific region (SSR) comprising an engineered polynucleotide marker and one or more primer regions, wherein each set of SCPs comprises a plurality of different TSRs configured to hybridize to different target measurands and the same SSR; hybridizing the TSRs of the SCPs of the plurality of sets of SCPs to the target measurands; cutting SCPs having TSRs that are hybridized to target measurands to release cut SSRs (cSSRs) without releasing SSRs of un-hybridized SCPs; isolating the cSSRs from un-hybridized SCPs and the hybridized TSRs using the affinity tag to form a pool of cSSRs; and performing digital PCR using the pool of cSSRs and primers configured to hybridize to the one or more primer regions of the cSSRs to amplify the engineered polynucleotide markers.

In some variations the assays described herein may include or may be part of a method such as a digital PCR method. For example, described herein are methods of digital PCR, the method comprising: combining a mixture of genetic material with a mixture of sequence conversion probes (SCPs), wherein the SCPs each include a target-specific region (TSR) configured to hybridize to one of a plurality of target measurands in the genetic material, and a signal specific region (SSR) comprising one of a set of engineered polynucleotide markers that each indicates a subset of the target measurands; hybridizing the TSRs of the mixture of SCPs to target measurands in the genetic material; cutting the SCPs having hybridized TSRs to release cut signal specific regions (cSSRs) from the hybridized SCPs; removing any SCPs that were not cut using an affinity marker adjacent to the TSRs of the SCPs to form a pool of cSSRs; and performing digital PCR using the pool of cSSRs and one or more primers specific to the cSSR that amplify the engineered polynucleotide markers of the cSSRs.

For example, a method of digital PCR may include: combining a mixture of genetic material with a mixture of sequence conversion probes (SCPs), wherein the SCPs each include a target-specific region (TSR) configured to hybridize to one of a plurality of target measurands in the genetic material, and a signal specific region (SSR) comprising one of a set of engineered polynucleotide markers that indicates on which chromosome the target measurand that hybridizes to the TSR is located; hybridizing the TSRs of the mixture of SCPs to any target measurands in the genetic material; cutting the SCPs having hybridized TSRs to release cut signal specific regions (cSSRs) from the hybridized SCPs; removing any SCPs that were not cut using an affinity marker adjacent to the TSRs of the SCPs to form a pool of cSSRs; and performing digital PCR using the pool of cSSRs and one or more primers specific to the cSSR that amplify the engineered polynucleotide markers of the cSSRs. Any of these methods may also include removing material/fetal genetic material that is bound to the TSR. Thus later steps of the method may proceed without the material/fetal genetic material.

The method may include performing digital PCR using the pool of cSSRs and the one or more primers comprises performing digital PCR using the cSSRs and a single pair of primers specific to all of the cSSRs. Any of these methods may include performing digital PCR using the pool of cSSRs and the one or more primers comprises performing digital PCR using a plurality of primers, wherein the total number of primers is less than a total number of target measurands.

The mixture of genetic material may comprise a mixture of maternal and fetal genetic material from a maternal blood sample.

As mentioned, cutting may comprise cutting with a nuclease (e.g., a flap endonuclease/5' nuclease, a double-strand nuclease, an RNA specific nuclease, a CAS, etc.), for example, an RNase H, a duplex-specific nuclease, a double-stranded DNase (dsDNase), and a restriction endonuclease. In some variations the nuclease comprises RNase H2.

In general, the engineered polynucleotide markers described herein may be non-cognate with the genetic material.

Performing digital PCR may comprise distributing the pool of cSSRs into a plurality of reaction samples at a dilution such that at least some of the reaction samples contain cSSRs and some do not contain cSSRs. These methods may include analyzing the engineered polynucleotide markers of the cSSRs present or absent in individual reaction samples to provide a first number of binary results representing presence or absence of a presumably euploid chromosome in the reaction samples and a second number of binary results representing presence or absence of a presumably aneuploid chromosome in the reaction samples. The method may include determining the presence or absence of an aneuploidy by comparing said first number with said second number, wherein a differential between the first number and the second number indicates the presence of polyploidy and/or aneuploidy.

For example, a method of determining a fetal aneuploidy may include: combining a mixture of maternal and fetal genetic material with a plurality of sequence conversion probes (SCPs), wherein each SCP comprises a polynucleotide target-specific region (TSR) between an affinity tag and a signal specific region (SSR), wherein the TSR is configured to hybridize to a target measurand from the maternal and fetal genetic material, and wherein the SSR comprises an engineered polynucleotide marker and one or more primer regions, further wherein the plurality of SCPs comprises a plurality of different TSRs configured to hybridize to different target measurands from the maternal and fetal genetic material, and each SCP of the plurality of SCPs comprises one of a first plurality of different engineered polynucleotide markers; hybridizing the TSRs of the plurality of SCPs to the target measurands; cutting SCPs from the plurality of SCPs having TSRs that are hybridized to the target measurands to release cut SSRs (cSSRs); isolating the cSSRs from un-hybridized SCPs and TSR hybridized to target measurands; distributing the cSSRs into a plurality of reaction samples at a dilution such that at least some of the reaction samples contain cSSRs and some do not contain cSSRs; analyzing the engineered polynucleotide markers of the cSSRs present or absent in individual reaction samples to provide a first number of binary results representing presence or absence of a presumably euploid fetal chromosome in the reaction samples and a second number of binary results representing presence or absence of a presumably aneuploid fetal chromosome in the reaction samples; determining the presence or absence of a fetal aneuploidy by identifying a differential between the first number and the second number. These methods may indicate several chromosomes based on the different engineered polynucleotide markers of the plurality of different engineered polynucleotide markers indicating different chromosomes.

Combining the mixture of maternal and fetal genetic material with the plurality of SCPs may include combining the mixture of maternal and fetal genetic material with a second plurality of SCPs, wherein the second plurality of SCPs comprises a second plurality of different TSRs configured to hybridize to different target measurands from the maternal and fetal genetic material, and each SCP of the second plurality of SCPs comprises the one or more second primer regions and one of a second plurality of different engineered polynucleotide markers. The first plurality of different engineered polynucleotide markers may indicate a first chromosome of the maternal and fetal genetic material and the second plurality of different engineered polynucleotide markers indicate a second chromosome of the maternal and fetal genetic material. The first plurality of different engineered polynucleotide markers may indicate different chromosomes of the maternal and fetal genetic material.

The engineered polynucleotide markers may each indicate a chromosome of the maternal and fetal genetic material. The plurality of SCPs may include a plurality of different TSRs configured to hybridize to target measurands on different chromosomes from the maternal and fetal genetic material, and the first plurality of different engineered polynucleotide markers may indicate which chromosome of the maternal and fetal genetic material a TSR corresponds to.

In general, one or more of the engineered polynucleotide markers, and the one or more second primer regions may be non-cognate with the maternal and fetal genetic material. The plurality of SCPs may comprise a plurality of different TSRs configured to hybridize to different target measurands on the same chromosome from the maternal and fetal genetic material.

The plurality of SCPs may comprise a plurality of different TSRs configured to hybridize to different target measurands on different chromosomes from the maternal and fetal genetic material. Distributing the cSSRs into the plurality of reaction samples may comprise distributing the cSSRs at low volume and/or high dilution whereby more engineered polynucleotide markers are detected in samples containing a trisomic or increased copy number of target measurand.

The mixture of maternal and fetal genetic material may be taken from less than 4 mL of blood.

For example, a method of determining a fetal aneuploidy may include: combining a mixture of maternal and fetal genetic material with a plurality of sequence conversion probes (SCPs) comprising a first subset of SCPs and a second subset of SCPs, wherein each of the SCPs in the plurality of SCPs comprises: a polynucleotide target-specific region (TSR) between an affinity tag and a signal specific region (SSR), wherein the TSR is configured to hybridize to a target measurand from the maternal and fetal genetic material, and wherein the SSR comprises an engineered polynucleotide marker between a forward primer region and a reverse primer region, further wherein the first subset of SCPs comprises a plurality of different TSRs configured to hybridize to different target measurands on a first chromosome, and each SSR of the first subset of SCPs comprises a same first forward primer region and a same first reverse primer region, and an engineered polynucleotide marker indicating the first chromosome, further wherein the second subset of SCPs comprises a plurality of different TSRs configured to hybridize to different target measurands on a second chromosome, and each SSR of the second subset of SCPs comprises a same second forward primer region and a same second reverse primer region and an engineered polynucleotide markers indicating the second chromosome, wherein the second forward primer region is the same or different from the first forward primer region and the second reverse primer region is the same or different from the second forward primer region; hybridizing the TSRs of the plurality of SCPs to the target measurands; cutting SCPs from the plurality of SCPs having TSRs that are hybridized to the target measurands to release cut SSRs (cSSRs); isolating the cSSRs from un-hybridized SCPs; distributing the cSSRs into a plurality of reaction samples at a dilution such that at least some of the reaction samples contain cSSRs and some do not contain cSSRs; analyzing the engineered polynucleotide markers of the cSSRs present or absent in individual reaction samples to provide a first number of binary results representing presence or absence of a presumably euploid fetal chromosome in the reaction samples and a second number of binary results representing presence or absence of a presumably aneuploid fetal chromosome in the reaction samples; determining the presence or absence of a fetal aneuploidy by comparing said first number with said second number.

The methods and compositions described herein may indicating the number of copies (or partial copies) of the one or more chromosomes being examined (e.g., chromosome 13, 18 and 21); for example, one or each one can be aneuploid (and/or polyploid). For example, 2 out of 3 may be euploid, 1 out of three may be euploid, and/or all of them or none of them may be euploid. Thus, the method described herein generally do not require the presence of a predefined euploid reference, and these methods may take the ratio and whichever one is "more" is aneuploid.

In any of the methods described herein, the assay may examine more than two chromosome (e.g., 13, 18 and 21, and in some variations, Y, plus X).

Any of the kits described herein may be used or adapted for use with a digital PCR method. For example, a kit that may be used for digital PCR as described herein may include, for example: a mixture of sequence conversion probes (SCPs), wherein the SCPs each include a target-specific region (TSR) configured to hybridize to one of a plurality of target measurands in from a plurality of human chromosomes, a signal specific region (SSR) comprising one of a set of engineered polynucleotide markers that indicate on which chromosome the target measurand that hybridizes to the TSR is located, wherein the engineered polynucleotide marker is flanked by a forward primer region and reverse primer region, and an affinity tag on the SCP on a region that does not overlap with the SSR; a nuclease configured to cut SCPs having TSRs that are hybridized to target measurand; a substrate comprising a binding partner that specifically binds to the affinity tag; and a first forward primer configured to hybridize to the first forward primer region and a first reverse primer (in some variations) configured to hybridize to the first reverse primer region. The kit may include a set of probes configured to uniquely identify individual engineered polynucleotide markers.

Another variation of a method as described herein includes the use of one or more sequence conversion probes configured as inversion (e.g., padlock) probes. For example, described herein are methods comprising: combining a plurality of sets of circularizing sequence conversion probes (cSCPs) with a sample mixture including a plurality of target measurands, wherein each set of cSCPs comprises a plurality of cSCPs, wherein each cSCP includes: a first end comprising a sense probe configured to hybridize to a first target-specific region, a second end comprising an antisense probe configured to hybridize to a second target-specific region, and a signal specific region (SSR) comprising an engineered polynucleotide marker a forward primer region and a reverse primer region, wherein each set of cSCPs comprises the same SSR and a plurality of different first and second target-specific regions configured to hybridize to different target measurands; hybridizing the cSCPs of the plurality of sets of cSCPs to the target measurands to produce circularization complexes; contacting the circularization complexes with a circularizing agent to circularize the cSCPs of the circularization complexes; and performing digital PCR using circularized cSCPs and primers configured to hybridize to the forward primer region and the reverse primer region (e.g., in some variations, if needed) of the cSSRs to amplify the engineered polynucleotide markers.

For example, a method may include: combining a plurality of subsets of circularizing sequence conversion probes (cSCPs) with a sample mixture including a plurality of target measurands to form a combined mixture, wherein each subset of cSCPs comprises a plurality of cSCPs each having a same signal specific region (SSR) including an engineered polynucleotide marker and a pair of target-specific regions (TSRs) configured to hybridize to a different target measurand; hybridizing cSCPs of the plurality of subsets of cSCPs to the target measurands to produce circularization complexes; contacting the circularization complexes with a circularizing agent to circularize the cSCPs of the circularization complexes; contacting un-circularized cSCPs in the combined mixture with exonuclease to cut the un-circularized cSCPs; and performing digital PCR using the circularized cSCPs and primers configured to hybridize to one or more primer region of the SSR to amplify the engineered polynucleotide markers.

A sequence conversion probe configured as an inversion probe method may be configured as a method of determining a fetal aneuploidy. For example, a method may include: combining a mixture of maternal and fetal genetic material including a plurality of target measurands with a plurality of sets of circularizing sequence conversion probes (cSCPs), wherein each set of cSCPs comprises a plurality of cSCPs, further wherein each cSCP includes: a first end comprising a sense probe to a first target-specific region specific to a particular target measurand from the plurality of target measurands, a second end comprising an antisense probe to a second target-specific region specific to the particular target measurand, and a signal specific region (SSR) comprising an engineered polynucleotide marker indicating a human chromosome associated with the particular target measurand, a forward primer region, and a reverse primer region, wherein each set of cSCPs comprises the same SSR and a plurality of different first and second target-specific regions configured to hybridize to different specific target measurands; hybridizing the cSCPs of the plurality of sets of cSCPs to the target measurands to produce circularization complexes; contacting the circularization complexes with a circularizing agent to circularize the cSCPs of the circularization complexes; and distributing the cSCPs into a plurality of reaction samples at a dilution such that at least some of the reaction samples contain cSCPs and some do not contain cSCPs; analyzing the engineered polynucleotide markers of the cSCPs present or absent in individual reaction samples to provide a first number of binary results representing presence or absence of a presumably euploid fetal chromosome in the reaction samples and a second number of binary results representing presence or absence of a presumably aneuploid fetal chromosome in the reaction samples; determining the presence or absence of a fetal aneuploidy by comparing said first number with said second number.

The engineered polynucleotide marker may be flanked by the forward and reverse primer regions, further comprising isolating the circularized cSCPs from linear cSCPs using an exonuclease. The number of primers may be much less than the number of target measurands. The sample mixture may include a mixture of maternal and fetal genetic material from a maternal blood sample. Performing digital PCR may include distributing the pool of cSCPs into a plurality of reaction samples at a dilution such that at least some of the reaction samples contain cSCPs and some do not contain cSCPs. The method may further include analyzing the engineered polynucleotide markers of the cSCPs present or absent in individual reaction samples to provide a first number of binary results representing presence or absence of a presumably euploid chromosome in the reaction samples and a second number of binary results representing presence or absence of a presumably aneuploid chromosome in the reaction samples.

Any of these methods may include determining the presence or absence of an aneuploidy by comparing said first number with said second number, wherein a differential between the first number and the second number indicates the presence of aneuploidy. The circularizing agent may be, for example, a ligase.

Another variation of a sequence conversion method as described herein includes primer driven methods and compositions. For example, described herein are methods, comprising: combining a plurality of subsets of primer-coupled target-specific probes with a sample mixture including a plurality of target measurands to form a combined mixture, wherein each primer-coupled target-specific probe comprises a target-specific region configured to hybridize to a target measurand of the plurality of target measurands and a sequence conversion primer (SC primer), wherein each subset of the primer-coupled target-specific probes incudes a same SC primer and multiple different target-specific regions; hybridizing the target-specific region of the primer-coupled target-specific probes to the target measurands; cutting primer-coupled target-specific probes that are hybridized to the target measurands to release SC primers without releasing SC primers of un-hybridized primer-coupled target-specific probes; contacting the released SC primers with sequence conversion templates (SCTs) and extending the SC primers to form copies of the SCTs, wherein the SCTs include an engineered polynucleotide marker; separating the copies of the SCT from the SCTs; and performing digital PCR using the copies of the SCTs and primers configured to hybridize to one or more primer region on the copy of the SCTs to amplify the engineered polynucleotide markers.

Cutting primer-coupled target-specific probes that are hybridized to the target measurands may include contacting the primer-coupled target-specific probes with a 5'-nuclease.

The SC primer may be coupled to an affinity tag so that the SC primers remain affinity tagged after cutting from the target-specific region of the primer-coupled target-specific probes. Contacting the released SC primers with the SCTs may include contacting the released SC primers with a circularized SCT. The SCTs may each couple to an affinity tag and separating the copies of the SCT from the SCTs may include binding the SCTs to a substrate.

The one or more target measurand may be a DNA or an RNA.

For example, a method of determining a fetal aneuploidy may include: combining a plurality of subsets of primer-coupled target-specific probes with a sample mixture of maternal and fetal genetic material including a plurality of target measurands to form a combined mixture, wherein each primer-coupled target-specific probe comprises a target-specific region (TSR) configured to hybridize to a target measurand of the plurality of target measurands and a sequence conversion primer (SC primer), wherein each subset of the primer-coupled target-specific probes incudes a same SC primer and multiple different target-specific regions; hybridizing the target-specific region of the primer-coupled target-specific probes to the target measurands; contacting the primer-coupled target-specific probes with a nuclease to release SC primers from primer-coupled target-specific probes that are hybridized to a target measurand, without releasing SC primers of un-hybridized primer-coupled target-specific probes; hybridizing the released SC primers to a subset of sequence conversion templates (SCTs) coupled to an affinity tag; extending hybridized SC primers to form copies of the SCTs, wherein the copies of the SCTs include an engineered polynucleotide marker; separating the copies of the SCT from the SCTs using the affinity tag; and performing digital PCR using the copies of the SCTs and primers configured to hybridize to one or more primer region on the copy of the SCTs to amplify the engineered polynucleotide markers. Also described herein are kits configured to perform these methods.

In general, the methods described herein may be used with or adapted for use with detection by nucleic acid amplification. Detection by nucleic acid amplification may include PCR and/or isothermal amplification. In some variations these nucleic acid amplification methods and techniques may only require one primer. In any of these methods an engineered polynucleotide marker (e.g., any SSR) may be detected by nucleic acid amplification technologies (such as, but not limited to PCR, digital PCR, etc.) and/or hybridization. In particular, the methods described herein may use or be adapted for use with isothermal amplification techniques (e.g. NASBA, LAMP, NEAR, WGA, SDA, HDA, RDA, CPT etc.).

Also described herein are sequence conversion probes (SCPs) and methods of engineering them. For example, a sequence conversion probe (SCP), may include: a target-specific region (TSR) extending between 15 and 50 base pairs (bp), wherein a polynucleotide sequence of the TSR is at least 80% identity to only a single region of one chromosome within a human genome, wherein the TSR includes a cognate restriction site for a type IIs restriction enzyme having a cut site that is at or near a first end of the TSR, further wherein the TSR has a GC content of greater than 50%; and a sequence-specific region (SSR) having a polynucleotide sequence extending greater than 40 bp (e.g., greater than 45 bp, greater than 50 bp, greater than 55 bp, between 40 and 100 bp, between 40-90 bp, between 40-80 bp, between 50-100 bp, between 50-90 bp, between 50-80 bp, etc.), wherein the polynucleotide sequence of the SSR sequence does not occur in the human genome, further wherein the SSR has a CG content of greater than 50%, wherein the TSR is joined to the SSR at the first end, further wherein the cognate restriction site is not part of a hairpin structure in the SCP. The SSR may include a forward primer region and a reverse primer region. For example, the SSR may include a forward primer region and a reverse primer region and an abasic region between the forward primer region and the reverse primer region.

The SCP may have a predicted secondary structure having an absolute minimum free energy (MFE) of less than 50 kcal/mol (e.g., less than 45, less than 40, less than 35, less than 30, etc.) kcal/mol.

The cut site for the type IIs restriction enzyme may be at the 5' end of the TSR. The TSR may have a melting temperature (Tm) of greater than 55 degrees C. The TSR may have a GC content of greater than 50%.

The type IIs restriction enzyme may be one of: BsaI and BspQI. In some examples the type IIs restriction enzyme is one of: BsaI, BspQI, BbsI-HF, BtsCI, BtsI-v2, BtsIMutI, FauI, BsrDI, BsrI, BsmBI, BsmFI, or BsmI.

For example, a sequence conversion probe may include: a target-specific region (TSR) extending between 15 and 50 base pairs (bp), wherein a polynucleotide sequence of the TSR is at least 80% identity to only a single region of one chromosome within a human genome, wherein the TSR includes a cognate restriction site for a type IIs restriction enzyme having a cut site that is at or near a first end of the TSR; and a sequence-specific region (SSR) extending greater than 40 bp (e.g., greater than 45 bp, greater than 50 bp, greater than 55 bp, between 40 and 100 bp, between 40-90 bp, between 40-80 bp, between 50-100 bp, between 50-90 bp, between 50-80 bp, etc.), wherein a polynucleotide sequence of the SSR sequence does not occur in the human genome and will not anneal to human chromosomal polynucleotides, further wherein the SSR includes a forward primer region and a reverse primer region and an abasic region between the forward primer region and the reverse primer region, wherein the TSR is joined to the SSR at the first end, further wherein the cognate restriction site is not part of a hairpin structure in the SCP and the SCP has a GC content that is greater than 50%.

For example, described herein are sequence conversion probes (SCPs) having: a target-specific region (TSR) extending between 15 and 50 base pairs (bp), wherein a polynucleotide sequence of the TSR is at least 80% identity to only a single region of one chromosome within a human genome; and a sequence-specific region (SSR) comprising a sequence of SEQ ID NO. 1, wherein the TSR is joined to the SSR.

For example, a sequence conversion probe (SCP) may include: a target-specific region (TSR) extending between 15 and 50 base pairs (bp), wherein a polynucleotide sequence of the TSR is at least 80% identity to only a single region of one chromosome within a human genome; and a sequence-specific region (SSR) comprising a sequence of SEQ ID NO. 1 wherein the SSR includes an abasic region within the sequence, further wherein the TSR is joined to the SSR.

A sequence conversion probe (SCP) may include: a target-specific region (TSR) extending between 15 and 50 base pairs (bp), wherein a polynucleotide sequence of the TSR is at least 80% identity to only a single region of one chromosome within a human genome; and a sequence-specific region (SSR) comprising: a polynucleotide of SEQ ID NO. 10 coupled to an abasic region that is coupled to a polynucleotide of SEQ ID NO. 11, wherein the TSR is joined to the SSR.

A sequence conversion probe (SCP) may include: a target-specific region (TSR) having a sequence of any one of: SEQ ID No. 8, 12, 15, 18, 21, 24, 27, 30, 33, 36, 39, 42, 45, 48, 51, 54, 57, 60, 63, 66, 69, 72, or 75; and a sequence-specific region (SSR) having a sequence of SEQ ID NO. 1 or SEQ ID NO. 4, wherein the TSR is joined to the SSR.

A sequence conversion probe (SCP) may include: a target-specific region (TSR) having a sequence of any one of: SEQ ID No. 8, 12, 15, 18, 21, 24, 27, 30, 33, 36, 39, 42, 45, 48, 51, 54, 57, 60, 63, 66, 69, 72, or 75; and a sequence-specific region (SSR) comprising a sequence of SEQ ID NO. 1 or SEQ ID NO. 4 wherein the SSR includes an abasic region within the sequence, further wherein the TSR is joined to the SSR.

A sequence conversion probe (SCP) may include: a target-specific region (TSR) having a sequence of any one of: SEQ ID No. 8, 12, 15, 18, 21, 24, 27, 30, 33, 36, 39, 42, 45, 48, 51, 54, 57, 60, 63, 66, 69, 72, or 75; and a sequence-specific region (SSR) comprising: a polynucleotide of SEQ ID NO. 10 coupled to an abasic region that is coupled to a polynucleotide of SEQ ID NO. 10, further wherein the TSR is joined to the SSR.

Also described herein are kits including any of the SCPs, and preferentially multiple types of SCPS that all have the same SSR. For example, a kit may include: a first sequence conversion probes (SCP) comprising: a first target-specific region (TSR) extending between 13 and 50 base pairs (bp) (e.g., between 14 and 50 bp, between 15 and 50 bp, etc.), wherein a polynucleotide sequence of the first TSR is at least 80% identity (at least 81%, at least 82%, at least 83%, at least 84%, at least 85% identity, etc.) to only a single region of one chromosome within a human genome, wherein the first TSR includes a cognate restriction site for a type IIs restriction enzyme having a cut site that is at or near a first end of the first TSR, further wherein the first TSR has a GC content of greater than 50%; and a first sequence-specific region (SSR) having a polynucleotide sequence extending greater than 40 bp (e.g., greater than 45 bp, greater than 50 bp, greater than 55 bp, between 40 and 100 bp, between 40-90 bp, between 40-80 bp, between 50-100 bp, between 50-90 bp, between 50-80 bp, etc.), wherein the polynucleotide sequence of the first SSR sequence does not occur in the human genome, further wherein the first SSR has a CG content of greater than 50%, wherein the first TSR is joined to the first SSR at the first end, further wherein the cognate restriction site is not part of a hairpin structure in the first SCP; and a second SCP comprising: a second TSR extending between 15 and 50 base pairs (bp), wherein a polynucleotide sequence of the second TSR is at least 80% identity to only a single region of one chromosome within the human genome, wherein the second TSR includes the cognate restriction site for the type IIs restriction enzyme having the cut site that is at or near a first end of the second TSR, further wherein the second TSR has a GC content of greater than 50%; and a second SSR having the same polynucleotide sequence as the first SSR, wherein the second TSR is joined to the second SSR at the first end, further wherein the cognate restriction site is not part of a hairpin structure in the second SCP.

Any of these kits may also include primers (e.g., a forward primer, a reverse primer, a link probe, etc.).

For example, described herein are methods, comprising: combining a first plurality of sequence conversion probes (SCPs) with a sample mixture including one or more target measurand, wherein each SCP comprises a polynucleotide including a target-specific region (TSR) and a circularizable signal specific region (SSR), the circularizable SSR comprising a first engineered polynucleotide marker including one or more primer regions, further wherein the first plurality of SCPs comprise a plurality of different TSRs configured to hybridize to different target measurands, wherein each SCP of the first plurality of SCPs includes the same SSR; hybridizing the TSRs to the one or more target measurand within the sample mixture; cutting SCPs having TSRs that are hybridized to the one or more target measurands to release cut SSRs (cSSRs) without releasing SSRs of un-hybridized SCPs; and hybridizing each of the cSSRs to a lock probe to produce circularization complexes; contacting the circularization complexes with a circularizing agent to circularize the cSSRs; and detecting the first engineered polynucleotide marker from the circularized cSSRs.

A method may include: combining a first plurality of sequence conversion probes (SCPs) with a sample mixture including one or more target measurand, wherein each SCP comprises a polynucleotide including a target-specific region (TSR) and a circularizable signal specific region (SSR), the circularizable SSR comprising a first engineered polynucleotide marker including one or more primer regions, further wherein the first plurality of SCPs comprise a plurality of different TSRs configured to hybridize to different target measurands, wherein each SCP of the first plurality of SCPs includes the same SSR; hybridizing the TSRs to the one or more target measurand within the sample mixture; cutting SCPs having TSRs that are hybridized to the one or more target measurands to release cut SSRs (cSSRs) without releasing SSRs of un-hybridized SCPs, wherein the cut does not produce an overhang; and hybridizing each of the cSSRs to a lock probe having a first sequence to produce circularization complexes; contacting the circularization complexes with a circularizing agent to circularize the cSSRs; and detecting the first engineered polynucleotide marker by performing digital PCR using the circularized cSSRs (cirSSR) and one or more primers configured to hybridize to the one or more primer regions to amplify the first engineered polynucleotide markers.

A method may include: combining a plurality of sets of sequence conversion probes (SCPs) with a sample mixture including a plurality of target measurands, wherein each set of SCPs comprises a plurality of SCPs, wherein each SCP includes: a polynucleotide target-specific region (TSR), and a circularizable signal specific region (SSR), the circularizable SSR comprising a first engineered polynucleotide marker including one or more primer regions, further wherein the plurality of SCPs include different TSRs; wherein each set of SCPs comprises the same SSR, and a plurality of different TSRs each configured to hybridize to a different target measurand; hybridizing the TSRs to target measurands in the sample mixture; cutting SCPs having TSRs that are hybridized to target measurands to release cut SSRs (cSSRs) without releasing SSRs of un-hybridized SCPs; hybridizing each of the cSSRs to a lock probe to produce circularization complexes; contacting the circularization complexes with a circularizing agent to circularize the cSSRs; and detecting the first engineered polynucleotide marker from the circularized cSSRs.

A method of determining a fetal aneuploidy may include: combining a mixture of maternal and fetal genetic material including a plurality of target measurands with a plurality of sets of sequence conversion probes (SCPs), wherein each set of SCPs comprises a plurality of SCPs, further wherein each SCP includes: a polynucleotide target-specific region (TSR), and a circularizable signal specific region (SSR), the circularizable SSR comprising a first engineered polynucleotide marker including one or more primer regions, further wherein the plurality of SCPs includes different TSRs; wherein each set of SCPs comprises the same SSR and a plurality of different TSRs configured to hybridize to different target measurands; hybridizing the TSRs to target measurands in the mixture; cutting SCPs having TSRs that are hybridized to the target measurands to release cut SSRs (cSSRs) without releasing SSRs of un-hybridized SCPs; hybridizing each of the cSSRs to a lock probe to produce circularization complexes; contacting the circularization complexes with a circularizing agent to circularize the cSSRs; distributing the circularized cSSRs into a plurality of reaction samples at a dilution such that at least some of the reaction samples contain cSSR and some do not contain cSSRs; analyzing the engineered polynucleotide markers of the cSSRs present or absent in individual reaction samples to provide a first number of binary results representing presence or absence of a presumably euploid fetal chromosome in the reaction samples and a second number of binary results representing presence or absence of a presumably aneuploid fetal chromosome in the reaction samples; and determining the presence or absence of a fetal aneuploidy by comparing said first number with said second number.

A method of determining a fetal aneuploidy may include: combining a mixture of maternal and fetal genetic material with a plurality of sequence conversion probes (SCPs), wherein each SCP comprises a polynucleotide target-specific region (TSR) and a signal specific region (SSR), wherein the TSR is configured to hybridize to a target measurand from the maternal and fetal genetic material, and wherein the SSR comprises an engineered polynucleotide marker including one or more primer regions, further wherein the plurality of SCPs comprises a plurality of different TSRs configured to hybridize to different target measurands from the maternal and fetal genetic material, and each SCP of the plurality of SCPs comprises one of a first plurality of different engineered polynucleotide markers; hybridizing the TSRs of the plurality of SCPs to the target measurands; cutting SCPs from the plurality of SCPs having TSRs that are hybridized to the target measurands without leaving an overhang, to release cut SSRs (cSSRs); hybridizing each of the cSSRs to a lock probe having a first polynucleotide sequence, to produce circularization complexes; contacting the circularization complexes with a circularizing agent to circularize the cSSRs; distributing the circularized cSSRs into a plurality of reaction samples at a dilution such that at least some of the reaction samples contain circularized cSSRs and some do not contain circularized cSSRs; analyzing the engineered polynucleotide markers of the circularized cSSRs present or absent in individual reaction samples to provide a first number of binary results representing presence or absence of a presumably euploid fetal chromosome in the reaction samples and a second number of binary results representing presence or absence of a presumably aneuploid fetal chromosome in the reaction samples; determining the presence or absence of a fetal aneuploidy by identifying a differential between the first number and the second number.

A method may include: hybridizing a target-specific region (TSR) of a sequence conversion probe (SCP) to a target measurand in a mixture; cutting the SCP having TSRs that is hybridized to the target measurand to release a cut sequence specific region (cSSR) from the SCP into the mixture; ligating an SSR extension probe comprising a second primer region to the cSSRs to form a long SSR; and performing digital PCR using the long SSR and primers configured to hybridize to one or more primer regions of the cSSR and to the second primer region of the SSR extension probe to amplify a portion of the long SSR.

A method of determining a fetal aneuploidy may include: combining a mixture of maternal and fetal genetic material with a plurality of sequence conversion probes (SCPs) comprising a first subset of SCPs and a second subset of SCPs, wherein each of the SCPs in the plurality of SCPs comprises: a polynucleotide target-specific region (TSR) and a signal specific region (SSR), wherein the TSR is configured to hybridize to a target measurand from the maternal and fetal genetic material, and wherein the SSR comprises an engineered polynucleotide marker having a forward primer region and a reverse primer region, further wherein the first subset of SCPs comprises a plurality of different TSRs configured to hybridize to different target measurands on a first chromosome, and each SCP of the first subset of SCPs comprises a same first forward primer region and a same first reverse primer region indicating the first chromosome, further wherein the second subset of SCPs comprises a plurality of different TSRs configured to hybridize to different target measurands on a second chromosome, and each SCP of the second subset of SCPs comprises a same second forward primer region and a same second reverse primer region indicating the second chromosome, wherein the second forward primer region is the same or different from the first forward primer region and the second reverse primer region is the same or different from the second forward primer region; hybridizing the TSRs of the plurality of SCPs to the target measurands; cutting SCPs from the plurality of SCPs having TSRs that are hybridized to the target measurands to release cut SSRs (cSSRs); isolating the cSSRs from un-hybridized SCPs; hybridizing each of the cSSRs to a lock probe having a first polynucleotide sequence, to produce circularization complexes; contacting the circularization complexes with a circularizing agent to circularize the cSSRs; distributing the circularized cSSRs into a plurality of reaction samples at a dilution such that at least some of the reaction samples contain circularized cSSRs and some do not contain circularized cSSRs; analyzing the engineered polynucleotide markers of the circularized cSSRs present or absent in individual reaction samples to provide a first number of binary results representing presence or absence of a presumably euploid fetal chromosome in the reaction samples and a second number of binary results representing presence or absence of a presumably aneuploid fetal chromosome in the reaction samples; determining the presence or absence of a fetal aneuploidy by comparing said first number with said second number.

A sequence conversion probe (SCP) may include: a target-specific region (TSR) extending between 14 and 50 base pairs (bp), wherein a polynucleotide sequence of the TSR has at least 80% identity to only a single region of one chromosome within a human genome, wherein the TSR includes a cognate restriction site for a type IIs restriction enzyme having a cut site that is at or near a first end of the TSR, further wherein the TSR has a GC content of greater than 50%; and a sequence-specific region (SSR) having a polynucleotide sequence extending greater than 40 bp, wherein the polynucleotide sequence of the SSR sequence does not occur in the human genome, further wherein the SSR has a CG content of greater than 50%, wherein the TSR is joined to the SSR at the first end, further wherein the cognate restriction site is not part of a hairpin structure in the SCP.

A kit may include: a first sequence conversion probes (SCP) comprising: a target-specific region (TSR) extending between 14 and 50 base pairs (bp), wherein a polynucleotide sequence of the TSR has at least 80% identity to only a single region of one chromosome within a human genome, wherein the TSR includes a cognate restriction site for a type IIs restriction enzyme having a cut site that is at or near a first end of the TSR, further wherein the TSR has a GC content of greater than 50%; a sequence-specific region (SSR) having a polynucleotide sequence extending greater than 40 bp, wherein the polynucleotide sequence of the SSR sequence does not occur in the human genome, further wherein the SSR has a CG content of greater than 50%, wherein the TSR is joined to the SSR at the first end, further wherein the cognate restriction site is not part of a hairpin structure in the SCP; and at least a first primer region in the SSR; and a first primer that hybridizes with the first primer region; and a lock probe that hybridizes to both a 5' end of SSR and to a 3' end of the SSR.

The SSR may further comprise a second primer region in the SSR, further wherein the kit comprises a second primer that hybridizes with the second primer region. Any of these kits may include the type IIs restriction enzyme.

A sequence conversion probe (SCP) may include: a target-specific region (TSR) extending between 14 and 50 base pairs (bp), wherein a polynucleotide sequence of the TSR has at least 80% identity to only a single region of one chromosome within a human genome, wherein the TSR includes a cognate restriction site for a type IIs restriction enzyme having a cut site that is at or near a first end of the TSR; and a sequence-specific region (SSR) extending greater than 40 bp, wherein a polynucleotide sequence of the SSR sequence does not occur in the human genome and will not anneal to human chromosomal polynucleotides, further wherein the SSR includes a forward primer region and a reverse primer region and an abasic region between the forward primer region and the reverse primer region, wherein the TSR is joined to the SSR at the first end, further wherein the cognate restriction site is not part of a hairpin structure in the SCP and the SCP has a GC content that is greater than 50%.

A kit may include: a first sequence conversion probes (SCP) comprising: a first target-specific region (TSR) extending between 15 and 50 base pairs (bp), wherein a polynucleotide sequence of the first TSR has at least 80% identity to only a single region of one chromosome within a human genome, wherein the first TSR includes a cognate restriction site for a type IIs restriction enzyme having a cut site that is at or near a first end of the first TSR, further wherein the first TSR has a GC content of greater than 50%; and a first sequence-specific region (SSR) having a polynucleotide sequence extending greater than 40 bp, wherein the polynucleotide sequence of the first SSR sequence does not occur in the human genome, further wherein the first SSR has a CG content of greater than 50%, wherein the first TSR is joined to the first SSR at the first end, further wherein the cognate restriction site is not part of a hairpin structure in the first SCP; and a second SCP comprising: a second TSR extending between 15 and 50 base pairs (bp), wherein a polynucleotide sequence of the second TSR has at least 80% identity to only a single region of one chromosome within the human genome, wherein the second TSR includes the cognate restriction site for the type IIs restriction enzyme having the cut site that is at or near a first end of the second TSR, further wherein the second TSR has a GC content of greater than 50%; and a second SSR having the same polynucleotide sequence as the first SSR, wherein the second TSR is joined to the second SSR at the first end, further wherein the cognate restriction site is not part of a hairpin structure in the second SCP.

A method may include: combining a plurality of sequence conversion probes (SCPs) with a sample mixture including one or more target measurand, wherein each SCP comprises a polynucleotide including target-specific region (TSR), and a signal specific region (SSR), the SSR comprising a first engineered polynucleotide marker, further wherein the plurality of SCPs include different TSRs; hybridizing the TSRs of the SCPs to the one or more target measurand; cutting SCPs having TSRs that are hybridized to the one or more target measurands to release cut SSRs (cSSRs) without releasing SSRs of un-hybridized SCPs; and detecting the first engineered polynucleotide marker from the cSSRs.

A method may include: combining a plurality of sequence conversion probes (SCPs) with a sample mixture including one or more target measurand, wherein each SCP comprises a polynucleotide including a target-specific region (TSR) and a signal specific region (SSR) comprising a first engineered polynucleotide marker including one or more primer regions, further wherein the plurality of SCPs comprises a plurality of different TSRs configured to hybridize to different target measurands, wherein each SCP of the plurality of SCPs includes the same SSR; hybridizing the TSRs of the SCPs to target measurand within the sample mixture; cutting SCPs having TSRs that are hybridized to the one or more target measurands to release cut SSRs (cSSRs) without releasing SSRs of un-hybridized SCPs; and detecting the first engineered polynucleotide marker from the cSSRs.

A method may include: combining a plurality of sequence conversion probes (SCPs) with a sample mixture including one or more target measurand, wherein each SCP comprises a polynucleotide including a target-specific region (TSR) and a signal specific region (SSR), the SSR comprising a first engineered polynucleotide including one or more primer regions, further wherein the plurality of SCPs comprises a plurality of different TSRs configured to hybridize to different target measurands, and each SCP of the plurality of SCPs comprises the same one or more primer regions; hybridizing the TSRs of the SCPs to the one or more target measurand; cutting SCPs having TSRs that are hybridized to the one or more target measurands to release cut SSRs (cSSRs) without releasing SSRs of un-hybridized SCPs; isolating the cSSRs from un-hybridized SCPs and from the hybridized TSRs; and detecting the first engineered polynucleotide marker from the cSSRs.

A method may include: combining a plurality of sequence conversion probes (SCPs) with a sample mixture including one or more target measurand, wherein each SCP comprises a polynucleotide target-specific region (TSR) and a signal specific region (SSR), the SSR comprising a first engineered polynucleotide marker including a first primer region, further wherein the plurality of SCPs comprises a plurality of different TSRs configured to hybridize to different target measurands, wherein at least some of the SCPs of the plurality of SCPs have different first primer regions, wherein there are fewer different first primer regions than there are different TSRs; hybridizing the TSRs of the SCPs to the one or more target measurand within the sample mixture; cutting SCPs having TSRs that are hybridized to the one or more target measurands to release cut SSRs (cSSRs) without releasing SSRs of un-hybridized SCPs; ligating an SSR extension probe comprising a second primer region to the cSSRs, wherein the second primer region; and detecting the first engineered polynucleotide marker from the cSSRs.

Any of these methods may include using a ligation blocker to prevent undesired ligation. For example, the both the 5' end of the SSR and the 3' end of the SSR extension probe may each includes a ligation blocker. The ligation blocker may include one of: 5' H, 5' biotin, 5' inverted bases, 5' digoxin. 5' D-bases. 3' PO4, 3' biotin, 3' inverted bases, 3' D-bases.

A method may include: combining a plurality of sequence conversion probes (SCPs) with a sample mixture including one or more target measurand, wherein each SCP comprises a polynucleotide target-specific region (TSR) and a signal specific region (SSR), the SSR comprising a first engineered polynucleotide marker including a first forward primer region and a first reverse primer region, further wherein the plurality of SCPs comprises a plurality of different TSRs configured to hybridize to different target measurands, wherein at least some of the SCPs of the plurality of SCPs have different first forward primer regions and first reverse primer regions, wherein there are fewer different first forward primer regions and first reverse primer regions than there are different TSRs; hybridizing the TSRs of the SCPs to the one or more target measurand within the sample mixture; cutting SCPs having TSRs that are hybridized to the one or more target measurands to release cut SSRs (cSSRs) without releasing SSRs of un-hybridized SCPs; isolating the cSSRs from un-hybridized SCPs and from the hybridized TSRs; and detecting the first engineered polynucleotide marker from the cSSRs.

A kit may include: a first plurality of sequence conversion probes (SCPs) directed against a plurality of target measurands, wherein each SCP comprises a polynucleotide target-specific region (TSR) configured to hybridize with one target measurand of the plurality of target measurands, wherein the TSR is between an affinity tag and a signal specific region (SSR), the SSR comprising a first engineered polynucleotide marker; a nuclease configured to cut SCPs having TSRs that are hybridized to target measurand; and a substrate comprising a binding partner that specifically binds to the affinity tag.

A method may include: hybridizing a target-specific region (TSR) of a sequence conversion probe (SCP) to a target measurand in a mixture; cutting the SCP having the TSRs that is hybridized to the target measurand to release a cut sequence specific region (cSSR) from the SCP into the mixture; hybridizing the cSSRs to a lock probe in the presence of a circularizing agent to circularize the cSSRs into a circularized SSR (cirSSR); and performing digital PCR using the circularized SSR and primers configured to hybridize to one or more primer regions of the cSSR to amplify a portion of the cSSR.

A kit may include: a first plurality of sequence conversion probes (SCPs) directed against a plurality of target measurands, wherein each SCP comprises a polynucleotide target-specific region (TSR) configured to hybridize with one target measurand of the plurality of target measurands, wherein the TSR is between an affinity tag and a signal specific region (SSR), the SSR comprising a first engineered polynucleotide marker; a nuclease configured to cut SCPs having TSRs that are hybridized to target measurand; and a substrate comprising a binding partner that specifically binds to the affinity tag.

A kit may include: a first plurality of sequence conversion probes (SCPs) directed against a first plurality of target measurands, wherein each SCP comprises: a polynucleotide target-specific region (TSR) configured to hybridize with one target measurand of the first plurality of target measurands, and wherein the TSR is between an affinity tag and a signal specific region (SSR), the SSR comprising a first engineered polynucleotide marker comprising one or more primer region; a nuclease configured to cut SCPs having TSRs that are hybridized to target measurand; a first forward primer configured to hybridize to the first forward primer region and a first reverse primer configured to hybridize to the first reverse primer region; and a substrate comprising a binding partner that specifically binds to the affinity tag.

A method may include: combining a plurality of sets of sequence conversion probes (SCPs) with a sample mixture including a plurality of target measurands, wherein each set of SCPs comprises a plurality of SCPs, wherein each SCP includes: a polynucleotide target-specific region (TSR), an affinity tag and a signal specific region (SSR) comprising an engineered polynucleotide marker and one or more primer regions, wherein each set of SCPs comprises a plurality of different TSRs configured to hybridize to different target measurands and the same SSR; hybridizing the TSRs of the SCPs of the plurality of sets of SCPs to the target measurands; cutting SCPs having TSRs that are hybridized to target measurands to release cut SSRs (cSSRs) without releasing SSRs of un-hybridized SCPs; isolating the cSSRs from un-hybridized SCPs and the hybridized TSRs using the affinity tag to form a pool of cSSRs; and performing digital PCR using the pool of cSSRs and primers configured to hybridize to the one or more primer regions of the cSSRs to amplify the engineered polynucleotide markers.

A method of digital PCR may include: combining a mixture of genetic material with a mixture of sequence conversion probes (SCPs), wherein the SCPs each include a target-specific region (TSR) configured to hybridize to one of a plurality of target measurands in the genetic material, and a signal specific region (SSR) comprising one of a set of engineered polynucleotide markers that each indicates a subset of the target measurands; hybridizing the TSRs of the mixture of SCPs to target measurands in the genetic material; cutting the SCPs having hybridized TSRs to release cut signal specific regions (cSSRs) from the hybridized SCPs; removing any SCPs that were not cut using an affinity marker adjacent to the TSRs of the SCPs to form a pool of cSSRs; and performing digital PCR using the pool of cSSRs and one or more primers specific to the cSSR that amplify the engineered polynucleotide markers of the cSSRs.

A method of digital PCR may include: combining a mixture of genetic material with a mixture of sequence conversion probes (SCPs), wherein the SCPs each include a target-specific region (TSR) configured to hybridize to one of a plurality of target measurands in the genetic material, and a signal specific region (SSR) comprising one of a set of engineered polynucleotide markers that indicates on which chromosome the target measurand that hybridizes to the TSR is located; hybridizing the TSRs of the mixture of SCPs to any target measurands in the genetic material; cutting the SCPs having hybridized TSRs to release cut signal specific regions (cSSRs) from the hybridized SCPs; removing any SCPs that were not cut using an affinity marker adjacent to the TSRs of the SCPs to form a pool of cSSRs; and performing digital PCR using the pool of cSSRs and one or more primers specific to the cSSR that amplify the engineered polynucleotide markers of the cSSRs.

A kit may include: a mixture of sequence conversion probes (SCPs), wherein the SCPs each include a target-specific region (TSR) configured to hybridize to one of a plurality of target measurands in from a plurality of human chromosomes, a signal specific region (SSR) comprising one of a set of engineered polynucleotide markers that indicate on which chromosome the target measurand that hybridizes to the TSR is located, wherein the engineered polynucleotide marker is flanked by a forward primer region and reverse primer region, and an affinity tag on the SCP on a region that does not overlap with the SSR; a nuclease configured to cut SCPs having TSRs that are hybridized to target measurand; a substrate comprising a binding partner that specifically binds to the affinity tag; and a first forward primer configured to hybridize to the first forward primer region and a first reverse primer configured to hybridize to the first reverse primer region.

A method may include: combining a plurality of sets of circularizing sequence conversion probes (cSCPs) with a sample mixture including a plurality of target measurands, wherein each set of cSCPs comprises a plurality of cSCPs, wherein each cSCP includes: a first end comprising a sense probe configured to hybridize to a first target-specific region, a second end comprising an antisense probe configured to hybridize to a second target-specific region, and a signal specific region (SSR) comprising an engineered polynucle-otide marker comprising: a forward primer region and a reverse primer region, wherein each set of cSCPs comprises the same SSR and a plurality of different first and second target-specific regions configured to hybridize to different target measurands; hybridizing the cSCPs of the plurality of sets of cSCPs to the target measurands to produce circular-ization complexes; contacting the circularization complexes with a circularizing agent to circularize the cSCPs of the circularization complexes; and performing digital PCR using circularized cSCPs and primers configured to hybrid-ize to the forward primer region and the reverse primer region of the cSSRs to amplify the engineered polynucle-otide markers.

A method may include: combining a plurality of subsets of circularizing sequence conversion probes (cSCPs) with a sample mixture including a plurality of target measurands to form a combined mixture, wherein each subset of cSCPs comprises a plurality of cSCPs each having a same signal specific region (SSR) including an engineered polynucle-otide marker and a pair of target-specific regions (TSRs) configured to hybridize to a different target measurand; hybridizing cSCPs of the plurality of subsets of cSCPs to the target measurands to produce circularization complexes; contacting the circularization complexes with a circularizing agent to circularize the cSCPs of the circularization com-plexes; contacting un-circularized cSCPs in the combined mixture with an exonuclease to cut the un-circularized cSCPs; and performing digital PCR using the circularized cSCPs and primers configured to hybridize to one or more primer region of the SSR to amplify the engineered poly-nucleotide markers.

A method of determining a fetal aneuploidy may include: combining a mixture of maternal and fetal genetic material including a plurality of target measurands with a plurality of sets of circularizing sequence conversion probes (cSCPs), wherein each set of cSCPs comprises a plurality of cSCPs, further wherein each cSCP includes: a first end comprising a sense probe to a first target-specific region specific to a particular target measurand from the plurality of target measurands, a second end comprising an antisense probe to a second target-specific region specific to the particular target measurand, and a signal specific region (SSR) com-prising an engineered polynucleotide marker indicating a human chromosome associated with the particular target measurand, a forward primer region, and a reverse primer region, wherein each set of cSCPs comprises the same SSR and a plurality of different first and second target-specific regions configured to hybridize to different specific target measurands; hybridizing the cSCPs of the plurality of sets of cSCPs to the target measurands to produce circularization complexes; contacting the circularization complexes with a circularizing agent to circularize the cSCPs of the circularization complexes; and distributing the cSCPs into a plural-ity of reaction samples at a dilution such that at least some of the reaction samples contain cSCPs and some do not contain cSCPs; analyzing the engineered polynucleotide markers of the cSCPs present or absent in individual reac-tion samples to provide a first number of binary results representing presence or absence of a presumably euploid fetal chromosome in the reaction samples and a second number of binary results representing presence or absence of a presumably aneuploid fetal chromosome in the reaction samples; determining the presence or absence of a fetal aneuploidy by comparing said first number with said second number.

A method may include: combining a plurality of subsets of primer-coupled target-specific probes with a sample mix-ture including a plurality of target measurands to form a combined mixture, wherein each primer-coupled target-specific probe comprises a target-specific region configured to hybridize to a target measurand of the plurality of target measurands and a sequence conversion primer (SC primer), wherein each subset of the primer-coupled target-specific probes incudes a same SC primer and multiple different target-specific regions; hybridizing the target-specific region of the primer-coupled target-specific probes to the target measurands; cutting primer-coupled target-specific probes that are hybridized to the target measurands to release SC primers without releasing SC primers of un-hybridized primer-coupled target-specific probes; contacting the released SC primers with sequence conversion templates (SCTs) and extending the SC primers to form copies of the SCTs, wherein the SCTs include an engineered polynucle-otide marker; removing the copies of the SCT from the SCTs; and performing digital PCR using the copies of the SCTs and primers configured to hybridize to one or more primer region on the copy of the SCTs to amplify the engineered polynucleotide markers.

A method of determining a fetal aneuploidy may include: combining a plurality of subsets of primer-coupled target-specific probes with a sample mixture of maternal and fetal genetic material including a plurality of target measurands to form a combined mixture, wherein each primer-coupled target-specific probe comprises a target-specific region (TSR) configured to hybridize to a target measurand of the plurality of target measurands and a sequence conversion primer (SC primer), wherein each subset of the primer-coupled target-specific probes incudes a same SC primer and multiple different target-specific regions; hybridizing the target-specific region of the primer-coupled target-specific probes to the target measurands; contacting the primer-coupled target-specific probes with an exonuclease to release SC primers from primer-coupled target-specific probes that are hybridized to a target measurand, without releasing SC primers of un-hybridized primer-coupled tar-get-specific probes; hybridizing the released SC primers to a subset of sequence conversion templates (SCTs) coupled to an affinity tag; extending hybridized SC primers to form copies of the SCTs, wherein the copies of the SCTs include an engineered polynucleotide marker; removing the copies of the SCT from the SCTs using the affinity tag; and performing digital PCR using the copies of the SCTs and primers configured to hybridize to one or more primer region on the copy of the SCTs to amplify the engineered polynucleotide markers.

Also described herein are sequence conversion probes. For example, a sequence conversion probe (SCP) may include: a target-specific region (TSR) extending between 15 and 50 base pairs (bp), wherein a polynucleotide sequence of the TSR has at least 80% identity to only a single region of one chromosome within a human genome; and a sequence-specific region (SSR) comprising a sequence of SEQ ID NO. 1, wherein the TSR is joined to the SSR.

A sequence conversion probe (SCP) may include: a target-specific region (TSR) extending between 15 and 50 base pairs (bp), wherein a polynucleotide sequence of the TSR has at least 80% identity to only a single region of one chromosome within a human genome; and a sequence-specific region (SSR) comprising a sequence of SEQ ID NO. 1 wherein the SSR includes an abasic region within the sequence, further wherein the TSR is joined to the SSR.

A sequence conversion probe (SCP) may include: a target-specific region (TSR) extending between 15 and 50 base pairs (bp), wherein a polynucleotide sequence of the TSR has at least 80% identity to only a single region of one chromosome within a human genome; and a sequence-specific region (SSR) comprising: a polynucleotide of SEQ ID NO. 10 coupled to an abasic region that is coupled to a polynucleotide of SEQ ID NO. 10, wherein the TSR is joined to the SSR.

A sequence conversion probe (SCP) may include: a target-specific region (TSR) having a sequence of any one of: SEQ ID No. 8, 12, 15, 18, 21, 24, 27, 30, 33, 36, 39, 42, 45, 48, 51, 54, 57, 60, 63, 66, 69, 72, or 75; and a sequence-specific region (SSR) having a sequence of SEQ ID NO. 1, wherein the TSR is joined to the SSR.

A sequence conversion probe (SCP) may include: a target-specific region (TSR) having a sequence of any one of: SEQ ID No. 8, 12, 15, 18, 21, 24, 27, 30, 33, 36, 39, 42, 45, 48, 51, 54, 57, 60, 63, 66, 69, 72, or 75; and a sequence-specific region (SSR) comprising a sequence of SEQ ID NO. 1 wherein the SSR includes an abasic region within the sequence, further wherein the TSR is joined to the SSR.

A sequence conversion probe (SCP) may include: a target-specific region (TSR) having a sequence of any one of: SEQ ID No. 8, 12, 15, 18, 21, 24, 27, 30, 33, 36, 39, 42, 45, 48, 51, 54, 57, 60, 63, 66, 69, 72, or 75; and a sequence-specific region (SSR) comprising: a polynucle-otide of SEQ ID NO. 10 coupled to an abasic region that is coupled to a polynucleotide of SEQ ID NO. 11, further wherein the TSR is joined to the SSR.

A method may include: hybridizing the target-specific region (TSR) of the sequence conversion probe (SCP) of any of the SCP described above to a target measurand in a mixture; cutting the SCP having the TSRs that is hybridized to the target measurands to release a cut sequence specific region (cSSR) from the SCP into the mixture; hybridizing the cSSRs to a lock probe in the presence of a circularizing agent to circularize the cSSRs into a circularized SSR (cirSSR); and performing digital PCR using the circularized SSR and primers configured to hybridize to one or more primer regions of the circularized SSR to amplify at least a portion of the c.

A method may include: combining a plurality of sets of sequence conversion probes (SCPs) with a sample mixture including a plurality of target measurands, wherein at least one of the SCPs of the set of SCPs is any of the SCP described above, further wherein the plurality of SCPs include different TSRs, and wherein each set of SCPs comprises the same SSR and a plurality of different first and second target-specific regions configured to hybridize to different target measurands; hybridizing the TSRs to target measurands; cutting SCPs having TSRs that are hybridized to the target measurands to release cut SSRs (cSSRs) with-out releasing SSRs of un-hybridized SCPs; hybridizing each of the cSSRs to a lock probe to produce circularization complexes; contacting the circularization complexes with a circularizing agent to circularize the cSSRs; and performing digital PCR using circularized cSSRs (cirSSRs) and primers configured to hybridize to the forward primer region and the reverse primer region of the cirSSRs to amplify at least a portion of the cirSSRs.

A method of determining a fetal aneuploidy may include: combining a mixture of maternal and fetal genetic material including a plurality of target measurands with a plurality of sets of sequence conversion probes (SCPs), wherein each set of SCPs comprises a plurality of SCPs, further wherein at least one of the SCPs of the set of SCPs is any of the SCPs described above, and wherein the plurality of SCPs includes different TSRs, further wherein each set of SCPs comprises the same SSR and a plurality of different first and second target-specific regions configured to hybridize to different target measurands; hybridizing the TSRs to target mea-surands; cutting SCPs having TSRs that are hybridized to the target measurands to release cut SSRs (cSSRs) without releasing SSRs of un-hybridized SCPs; hybridizing each of the cSSRs to a lock probe to produce circularization com-plexes; contacting the circularization complexes with a circularizing agent to circularize the cSSRs; and distributing the circularized cSSRs into a plurality of reaction samples at a dilution such that at least some of the reaction samples contain cSSR and some do not contain cSSRs; analyzing the engineered polynucleotide markers of the cSSRs present or absent in individual reaction samples to provide a first number of binary results representing presence or absence of a presumably euploid fetal chromosome in the reaction samples and a second number of binary results representing presence or absence of a presumably aneuploid fetal chro-mosome in the reaction samples; determining the presence or absence of a fetal aneuploidy by comparing said first number with said second number.

All of the methods and apparatuses described herein, in any combination, are herein contemplated and can be used to achieve the benefits as described herein.

BRIEF DESCRIPTION OF THE DRAWINGS

The novel features of the invention are set forth with particularity in the claims that follow. A better understanding of the features and advantages of the present invention will be obtained by reference to the following detailed descrip-tion that sets forth illustrative embodiments, in which the principles of the invention are utilized, and the accompany-ing drawings of which:

FIG. 1A shows an example of a sequence conversion method using a sequence conversion probe (SCP) for linearly converting a target polynucleotide into an engineered polynucleotide that may be detected using nucleic acid amplification and/or by hybridization to one or more probes. FIG. 1B is another example of a sequence conversion method in which the sequence conversion probe is coupled to a label. FIG. 1C is another example of a sequence conversion method in which the sequence conversion probe is bound to a substrate (e.g., magnetic bead).

FIG. 1D shows an example of a sequence conversion method similar to that shown in FIG. 1A, using a sequence conversion probe (SCP) for linearly converting a target polynucleotide into an engineered polynucleotide that may be detected using nucleic acid amplification and/or by hybridization to one or more probes.

FIG. 7A shows examples of sequence conversion probes (SCPs) as described herein, including a sequence conversion probe with an affinity tag (e.g., biotin) on either the 5' or 3' end of the sequence conversion probe.

FIG. 7B illustrates one example of cutting of a sequence conversion probe into a cut target-specific region (cTSR) and a cut or cleaved signal specific region (cSSR). The "R" in FIG. 7B may be a restriction site or a ribose. If the R is a ribose, the SCP is cut (e.g., after hybridizing to a target measurand sequence) by a nuclease that preferentially cuts ribonucleotides, such as RNase H2. Alternatively, the "R" may refer to a recognition site for a restriction enzyme (e.g., for cutting by a restriction site).

FIG. 7C illustrates examples of sequence conversion probes (SCPs) configured for RNA or DNA targets. The figure illustrates (top) a SCP that is cut by a duplex-specific nuclease (DSN) which may fully degrade the hybridized target-specific region (TSR), leaving intact the cut signal specific region (cSSR). FIG. 7C also illustrates partial (e.g., incomplete) degradation that may occur where there are mismatches between the TSR and the target measurand in the presences of DSN. Such mismatches may be intentionally introduced.

FIG. 8 schematically illustrates the use of a sequence conversion method as described herein to convert an RNA target measurand into a signal specific region (SSR or cSSR) DNA with amplification, as the target measurand RNA may be re-hybridized to SCP following degradation of the target-specific region (TSR). The amplification may be limited and may be linear; for example, amplification may be limited by the amount of SCP specific to the RNA target measurand.

FIG. 9 illustrates the use of a sequence conversion method similar to that shown in FIG. 8 but for DNA target measurands, in which the target DNA measurand is reused while the SCP is consumed by converting into cut or cleaved SSR (cSSR) and degraded target-specific region (TSR). In FIG. 9 the enzyme used is RNase H2 and the TSR includes a plurality of ribonucleotides that are preferentially cut by the RNase H2. In some variations, the same effect may be achieved by placing a single cleavage site towards the center of the TSR, e.g. a ribose for RNase H2 or a restriction site for a nick restriction enzyme.

In FIG. 11 the chromosome polynucleotides (chromosomes C13, C18, and C21) are show as solid lines; the actual genetic material used in the assay may be fractured as circulating cell free DNA.

In FIG. 14, the cut SSR may be directly detected by binding to a reporter probe (direction or indirectly) and/or a capture probe (directly or indirectly).

In FIG. 16 the restriction site is here configured to be recognized by BmtI-HF. Other restriction sites can be chosen to accommodate other restriction enzymes.

FIGS. 17 and 18 illustrate one example of a sequence conversion method in which the nuclease that may be used to cut the signal specific region from the rest of the sequence conversion probe is a flap endonuclease (e.g., FEN-1) or a 5'-3' nuclease.

FIG. 19A shows a linear version of the sequence conversion probe, which may be referred to as a circularizing sequence conversion probe (cSCPs). In this example, the cSCP includes a sense TSR1, a pair of primer regions, a signal specific region (SSR), and an antisense TSR2. FIG. 19B shows the cSCP of FIG. 19A hybridized to a measurand, forming a circularization complex that may be circularized, as shown in FIG. 19C, e.g., by the addition of a circularizing agent, such as a ligase.

In FIG. 20 the assay includes a plurality of circularizing sequence conversion probes (cSCPs) adapted for use as part of a digital PCR assay, e.g., for determining aneuploidy of one or more chromosomes. Multiple sets of cSCPs targeting specific target measurands on different chromosomes may combined with sample genetic material as shown, and circularized cSCPs may be formed and used as input into the digital PCR procedure. This configuration may be a fully engineered SSR (e.g., including synthetic sequence, not corresponding to genetic material from the target).

In FIG. 21A, the assay includes a plurality of sequence conversion probes that, after a target sequence region (TSR) of the SCP hybridizes to a target region (e.g., of measurand), may be cut by a restriction enzyme to release the signal specific region that may be circularized by a lock probe and a ligase to form cirSSR. Linear DNA (including hybridized DNA) may be digested, and remaining cirSSR may be amplified and/or detected. This may be part of a digital PCR quantification method, e.g., to detect chromosome ploidy.

In FIG. 21C, the SSR does not necessarily include a separate first and second hybridization region (e.g., Hyb1, Hyb2), but the lock probe may be configured to hybridize to the ends of the SSR where the ends may include the probe region and a primer region (e.g., forward primer).

In FIG. 22A the SC primer is combined with an affinity tagged sequence conversion template (SCT) and extended to make a copy of the sequence conversion template. In FIG. 22B the SC primer may be affinity tagged and, when hybridized to a circularized ("Cyclic template") sequence conversion template (SCT) to form a copy of the sequence conversion template (cSCT). The cSCT may be separated from the affinity tagged SCT (and from the original genetic material) and used for quantification, e.g., by direct quantification or by amplification (e.g., by digital PCR, etc.).

In FIG. 29A, a sequence conversion probe (SCP) for converting a target polynucleotide (target measurand) into an engineered polynucleotide combined with a sample mixture to be examined for a target measurand (e.g., shown as genomic DNA in FIG. 29A). SSR is released (as cSSR) only from those SCPs that hybridized to target measurand by digestion of hybridized SCPs.

FIG. 29B schematically illustrates conversion of the cSSR from FIG. 29A into a sequence (which does not include any genomic, e.g., target measurand, sequence) that may be detected using nucleic acid amplification and/or by hybridization. In FIG. 29B an SSR extension probe is selectively annealed to the 3' end of the cSSR by ligation and the resulting final amplicon (cSSR+SSR extension probe) is a linear polynucleotide product that may be detected to indicate the presence and/or amount of target measurand in the sample.

In FIG. 29C an SSR extension probe is added to the 3' end of the cSSR and the entire product (of cSSR+SSR extension probe) is circularized. The resulting circular SSR (cirSSR) may be detected to indicate the presence and/or amount of target measurand in the sample.

DETAILED DESCRIPTION

Figure 1A:
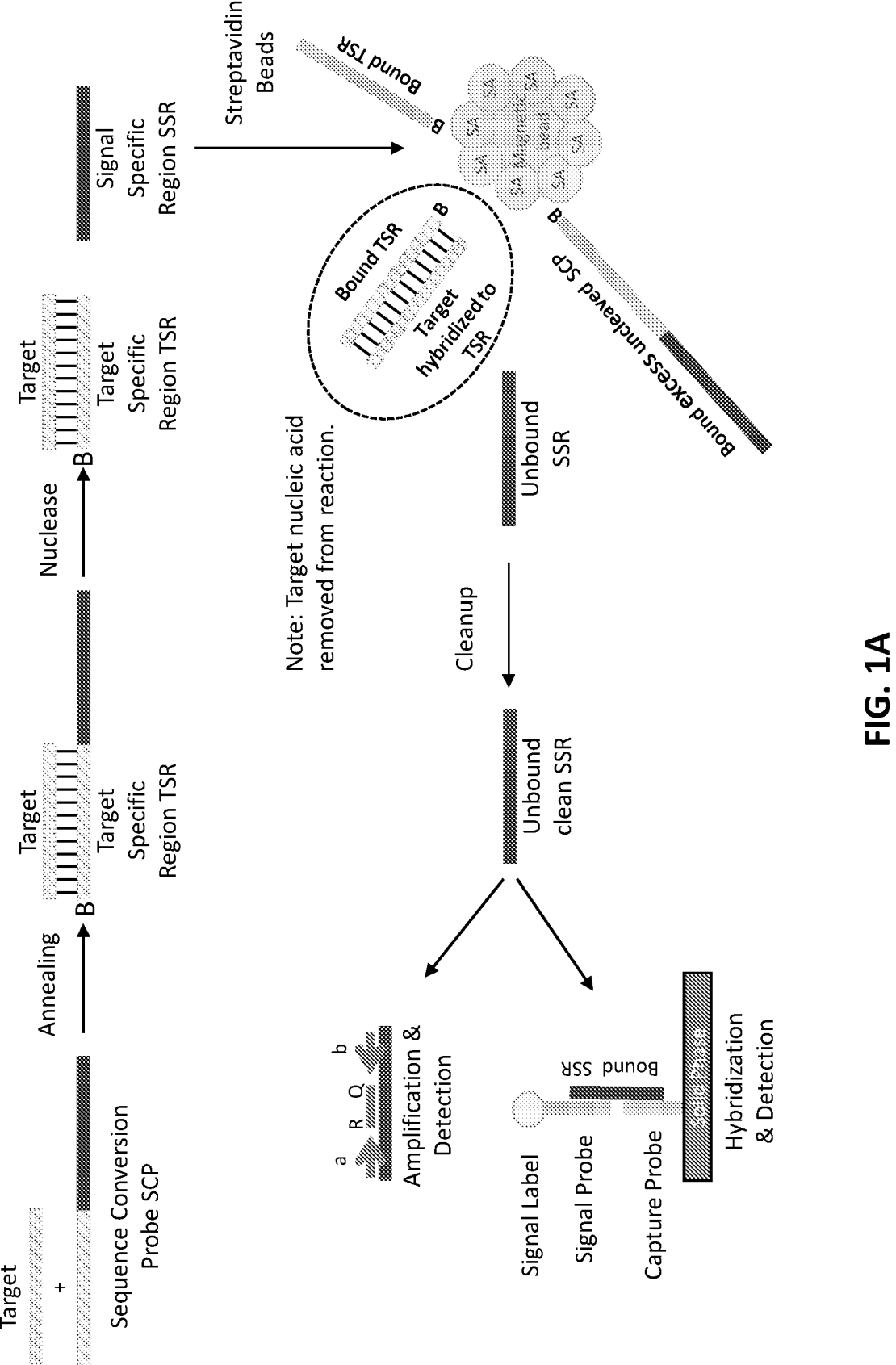
FIGS. 1A to 1C illustrate examples of sequence conver-sion methods as described herein.

Provided herein are compositions, kits, and methods for the detection and quantitation of nucleic acids. Practice of some methods and use of some compositions herein can simplify and improve the detection and quantitation of analytes quantitated through measuring their nucleic acids (e.g. the quantification of bacteria, human or other chromosomes, genes, pathogens, etc.). The disclosure herein provides methods for converting a plurality of measurands into a smaller number or even a single unified measurand. For example, the disclosure herein provides methods for converting a plurality of different nucleic acid targets for one or more alleles present on a chromosome into a single measurand. This approach thus may simplify assays using nucleic acid amplification and hybridization quantification methods, such as digital counting methods. It may also improve the accuracy of those methods. The current state of the art for performing non-invasive prenatal testing (NIPT) by PCR would require many unique primers and/or probes as each unique measurand requires two unique primers and may require a unique probe as well. The methods and compositions disclosed herein simplifies the chemistry to a few or even as little as one primer pair (2 primers) and 3 unique probes for NIPT for detecting trisomy 13, 18 and 21. This approach is broadly applicable to hybridization quantification methods.

This disclosure may significantly simplify the design for NIPT dPCR assays, offer flexibility to easily select target measurand sequences including shorter sequences, reduce the complexity of an assay for NIPT to a few or even a single primer pair for all chromosomes and may only require a single probe per chromosome, while allowing enough alleles on each chromosome to be targeted/tested to meet the statistically required number of replicates to achieve needed clinical performance.

This methods and compositions (including kits) described herein may require only two primers and three probes to allow digital PCR analysis, resulting in a clean reaction. Starting with maternal and fetal DNA extracted from 1-2 mL of plasma to achieve 100 000 counts per chromosome 13, 18 and 21 it is estimated with conventional methods 600 primers and 300 probes are needed, for 200 000 counts 1200 primers and 600 probes.

These simplifications increase the robustness of the assay and allow targeting a high number of sequences without having to worry about primer/primer/probe interaction causing an unspecific reaction.

Definitions

As used herein: accuracy refers to closeness of a measurement to a specific or correct value. Analyte refers to a substance of interest in an analysis, such as a nucleic acid of a specific chromosome, a specific virus, a specific bacterium, etc.

Analyte specific SSR refers to a common signal specific region (SSR) sequence for a defined analyte (e.g. a specific chromosome, a specific virus, a specific bacterium, etc.). The "analyte specific SSR" is connected on sequence conversion probe (SCPs) with different "measurand specific TSR". These sequence conversion probe (SCP) detect a common analyte by detecting a plurality of analyte specific measurands (e.g. different alleles on chromosomes or pathogens).

Aneuploidy refers to the state where the wrong number of chromosomes (e.g., the wrong number of full chromosomes or the wrong number of chromosome segments, such as the presence of deletions or duplications of a chromosome segment) is present in a cell. In the case of a somatic human cell it may refer to the case where a cell does not contain 22 pairs of autosomal chromosomes and one pair of sex chromosomes. In the case of a human gamete, it may refer to the case where a cell does not contain one of each of the 23 chromosomes. In the case of a single chromosome type, it may refer to the case where more or less than two homologous, but non-identical chromosome copies are present, or where there are two chromosome copies present that originate from the same parent. In some embodiments, the deletion of a chromosome segment is a microdeletion.

In the figures, "B" refers to an affinity tag, including (but not limited to) biotin or another affinity tag. The affinity tag may allow removal of unwanted moieties such as following hybridization and cutting steps.

Chromosome refers to either a full chromosome, or a segment or section of a chromosome.

CRISPR-Cas refers to a system for controlled or programmable genome engineering. CRISPR refers to clustered regularly interspaced short palindromic repeats. Cas is an endonuclease that cuts DNA at a location specified by a specific RNA (may be referred to as a guide RNA).

cirSSR is a circularized exonuclease resistant signal specific region (SSR) derived from a cSSR.

cSSR is a signal specific region (SSR) of a sequence conversion probe (SCP) after cutting such as by e.g., a nuclease.

cTSR is a target-specific region (TSR) portion of the sequence conversion probe (SCP) after cutting by e.g., a nuclease.

Digital PCR (dPCR) is an alternate method to conventional φRT-PCR for absolute quantification and detection of nucleic acid molecules. dPCR works by partitioning a sample of DNA or cDNA into many individual, parallel PCR reactions; some of these reactions contain the target nucleic acid molecule (positive) while others do not (negative) and amplifying the sample. A single starting molecule of DNA or cDNA can be amplified a million-fold or more. During amplification, dye-labeled probes are used to detect sequence-specific targets. When no target sequence is present, no signal accumulates. Following PCR analysis, the fraction of negative reactions is used to generate an absolute count of the number of target molecules in the sample, without the need for standards or endogenous controls.

Duplex refers to DNA:DNA double strand or DNA:RNA double strand.

Lock Probe refers to an oligonucleotide which, in the presence of ligase, facilitates formation of a cirSIR.

The term "kit" (or "kit of parts") refers to an article of manufacture including one or more containers and, optionally, a data carrier. The one or more containers may be filled with one or more of the reagents described herein. Additional containers may be included in the kit that contain, e.g., diluents, buffers and further reagents such as dNTPs. The data carrier may be a non-electronic data carrier, e.g., a graphical data carrier such as an information leaflet, an information sheet, a bar code or an access code, or an electronic data carrier such as a floppy disk, a compact disk (CD), a digital versatile disk (DVD), a microchip or another semiconductor-based electronic data carrier. The access code may allow the access to a database, e.g., an internet database, a centralized, or a decentralized database. The data carrier may include instructions for the use of the kit in the methods described herein. The data carrier may include a cut-off value or reference level. In case that the data carrier includes an access code which allows the access to a database, the threshold value or reference level is deposited in this database. In addition, the data carrier may comprise information or instructions on how to carry out the methods in this disclosure.

As used herein, a measurand refers to a nucleic acid representing one of many possible sequences/alleles of (or in) an analyte.

Measurand specific TSR refers to a target-specific region (TSR) specific for a measurand. Different "measurand specific TSRs" can be linked to a common "analyte specific SSR".

NIPT refers to non-invasive prenatal testing and in some cases may refer to trisomy-based analysis on cell-free DNA in maternal blood or plasma.

Nucleic acid or nucleic acid molecule refers to DNA and/or RNA.

Nuclease refers to an enzyme that degrades nucleic acids by breaking bonds between nucleotides in the nucleic acids. Nucleases can act on DNA (DNase) and/or RNA (RNase). A duplex specific nuclease (DSN) selectively cuts DNA in a nucleic acid duplex (DNA/DNA) or heteroduplex (e.g., RNA/DNA). A duplex specific nuclease may leave one strand or part of one strand intact. Many nucleases are commercially available and include, but are not limited to: Restriction enzymes, 5'-3' nucleases, RNase H, RNase H2, RNase HII, RNase V, duplex-specific nuclease (DSN), lambda exonuclease, T7 exonuclease, exonuclease III, RecJf, exonuclease I, exonuclease T, exonuclease V, BAL-31 nuclease, mung bean nuclease, DNase I, micrococcal nuclease, T7 endonuclease I, T5 exonuclease, Cas9 and any combination thereof. Information regarding nucleases and their substrates is found, e.g., in Mishra, Nawin C; (Nucleases: Molecular Biology and Applications, Wiley-Interscience (ISBN: 978-0-471-39461-7). Additional nucleases of interest include but are not limited to: RNase V1 (e.g., for cutting dsRNA), oligoribonucleases, (e.g., for cutting oligonucleotides), exoribonuclease II (e.g., for cutting mature miRNAs).

Oligonucleotide refers to a single-stranded multimer of nucleotides from 2 to about 500 nucleotides, e.g., 2 to 200 nucleotides. Oligonucleotides may be synthetic or may be made enzymatically, and, in some embodiments, are under 10 to 50 nucleotides in length. Oligonucleotides may contain ribonucleotide monomers (i.e., may be oligoribonucleotides or "RNA oligonucleotides") or deoxyribonucleotide monomers (i.e., may be oligodeoxyribonucleotides or "DNA oligonucleotides") or chemical linker. Oligonucleotides may be 10 to 20, 11 to 30, 31 to 40, 41 to 50, 51-60, 61 to 70, 71 to 80, 80 to 100, 100 to 150 or 150 to 200, up to 500 or more nucleotides in length, for example.

Padlock Probe refers to an oligonucleotide composed of two target complementary segments connected by a linker that may carry detectable functions. The two ends of the linear oligonucleotide probes are brought in juxtaposition by hybridization to a target sequence (e.g. a Lock Probe). This juxtaposition allows the two probe segments to be covalently joined by the action of a DNA ligase. As used herein, a padlock probe may be a specific type of inversion probe in which there is no gap between the target complementary regions at the ends of the probe (e.g., the target complementary regions span the entire target region upon hybridization, leaving no gaps). In general, an inversion probe may include no gaps (as in a padlock probe) or may include a gap (e.g., a gap of 1 bp, a gap of 2 bp, a gap of 3 bp, etc.). Inversion probes having larger gaps (e.g., >2-5 bp, >2 bp, >3 bp, >4 bp, >5 bp, etc.) may be referred to as connector inversion probes.

Primer refers to a single DNA molecule (a DNA oligomer) or a collection of DNA molecules (DNA oligomers) in which the DNA molecules are identical, or nearly so, and where the primer contains a region that is designed to hybridize to a targeted locus (e.g. a targeted polymorphic locus or a nonpolymorphic locus) and may contain a priming sequence designed to allow PCR amplification.

R refers to one or more Ribonucleotides or other nucleotide analog or a recognition site for a Restriction Enzyme; they may allow site-specific cutting upon hybridization to a nucleic acid target.

SCA refers to sequence conversion method.

SCORE refers to a sequence conversion reaction. A sequence conversion reaction "converts" a nucleic acid into a different form (sometimes referred to as a "proxy").

SCP refers to sequence conversion probe.

SSR refers to a signal specific region.

Sequence refers to a DNA sequence or a genetic sequence. It may refer to the primary, physical structure of the DNA molecule or strand in an individual. It may refer to the sequence of nucleotides found in that DNA molecule, or the complementary strand to the DNA molecule. It may refer to the information contained in the DNA molecule as its representation in silico.

Subject relates to any organism such as a vertebrate, particularly any mammal, including both a human and another mammal, e.g., an animal such as a rodent, a rabbit, or a non-human primate (e.g., a monkey). The rodent may be a mouse, rat, hamster, guinea pig, or chinchilla. In some embodiments, the subject is a pregnant human female.

A substrate refers to a substance on which an enzyme acts. For example,

T21, T18, T13 refer to trisomy of chromosomes 21, 18, 13, respectively.

TSR refers to target-specific region. A unique target-specific region represents a unique measurand. (e.g. a specific allele sequence)

An analyte can be quantified by a sum of measurements, e.g. the analyte human chromosome 21 includes potentially thousands of measurands represented by thousands of detectable sequences across chromosome 21. Chromosome 21 has a length of ~48 Mbases. This theoretically represents 480,000 unique measurands of an average length of 100 bases.

This method uses in some embodiments "analyte specific SSRs" [meaning e.g. chromosome specific SSR] linked to "measurand specific TSR" [specific to a unique sequence/allele on the chromosome].

Sequence Conversion Method

FIG. 1A illustrates one example of a sequence conversion method (e.g., a method of performing a sequence conversion reaction) for detecting a target of interest by converting the target of interest from a target measurand into a different form, e.g., an engineered "signal specific region" (SSR) that may act as a proxy for the target measurand, and then detecting the signal specific region (proxy). In some examples, the target measurand may be, for example, part of a chromosome allele. The method shown in FIG. 1A utilizes a sequence conversion probe (SCP) that has at least two different functional domains: a first, target-specific region (TSR) is configured to hybridize to the measurand of a target, and the second, the signal specific region (SSR) is engineered to be readily amplifiable and/or detectable.

FIG. 1A shows the target-specific region of the sequence conversion probe (SCP) hybridizing to a target measurand (e.g., a portion of a chromosome of interest) under appropriate annealing conditions to form a target-sequence conversion probe complex (target-SCP). The target-sequence conversion probe complex (target-SCP) has a double stranded region where the target measurand and target-specific region (TSR) of the sequence conversion probe are hybridized and a single stranded region, the signal specific region (SSR). When complexed with a target measurand, the sequence conversion probe (SCP) includes a nuclease recognition site and exposing the target-sequence conversion probe complex (target-SCP) to the nuclease results in cutting of the sequence conversion probe (SCP) at the nuclease recognition site and forming, in this example, a double stranded region where the target and target-specific region (TSR) of the sequence conversion probe is hybridized and a separate cleaved off single stranded region, the signal specific region. Although the target measurand is shown as a polynucleotide fragment, it may be any size, and may be part of a longer polynucleotide chain. The target measurand may be any appropriate polynucleotide, and the SCP may be adapted for use with a particular type of target (e.g., RNA, DNA, length of oligonucleotide etc.).

The affinity tag in FIG. 1A is shown as a biotin (B) and its binding partner, streptavidin (SA) is coupled to one example of a solid substrate (e.g., magnetic beads or microtiterplate). The sequence conversion probe (SCP) may be labeled with an affinity tag to aid in removal of unwanted forms of the sequence conversion probe; in particular, they may be labeled on the target-specific region. The streptavidin on the magnetic beads will bind to biotin affinity tag on the nucleic acid. The biotin-labeled nucleic acid may be the single-stranded uncleaved SCP or the target-specific region that is cleaved from the sequence conversion probe (which may be hybridized to the target measurand. Thus, uncleaved sequence conversion probe (SCP) (and in this variation, target DNA) may be removed from the reaction. A magnet field can be used to separate the streptavidin coated magnetic beads and bound biotinylated DNA from the signal specific region. For example, the cleaved signal specific regions can be removed from the magnetic beads (or vice versa), such as by using magnets or a spin column to separate out the magnetic beads. The solution can be analyzed for the presence of the signal specific region to determine the presence or absence of target measurand in the original sample. Any appropriate detection method may be used. In FIG. 1A, for example, amplification and detection or hybridization and detection may be used. Amplification and detection may be performed using a nucleotide amplification technique, including but not limited to digital PCR. Amplification may use one or more primers, such as in some variations a forward primer (primer a) and a reverse primer (primer b). In some variations this amplification may be quantified by use of a florescent marker, such as the Taqman assay including a probe with a fluorophore (R) and a quencher (Q). Other amplification detection techniques may be used.

Direct visualization of the cleaved SSR (cSSR) may also be used. For example, FIG. 1A illustrates a hybridization and detection using a capture probe attached or made to be attached to a solid phase and configured to hybridize to the signal specific region. Alternatively or additionally, a signal probe that is configured to bind (e.g., hybridize) the SSR (or the combination of the SSR and capture probe) may be used, as shown. The signal probe may include a signal label, such as a fluorescent label. The capture probe and/or signal probe may hybridize by annealing to the SSR, and/or they may specifically bind by other molecular interaction. For example, the probe(s) may be antibody probes (or portions of antibodies, such as Fab fragments, etc.), aptamer probes, or the like.

The SSR may be engineered to have a predetermined length, or range of lengths, polynucleotide content (e.g., GC ratio, etc.), and/or sequence. In particular in variations in which multiple different SSRs are used, either to indicate different specific target measurands (individual measurands) or to identify groups of target measurands (e.g., grouped by gene, by chromosome, by genetic pathway, by pathogen, mutations indicative of cancer, etc.), the SSRs may be distinct from each other, but may be engineered to have similar functional properties, such as melting temperature, primer regions, length, etc. This may help prevent bias that may otherwise occur during detection (e.g., amplification and/or binding).

Figure 1B:
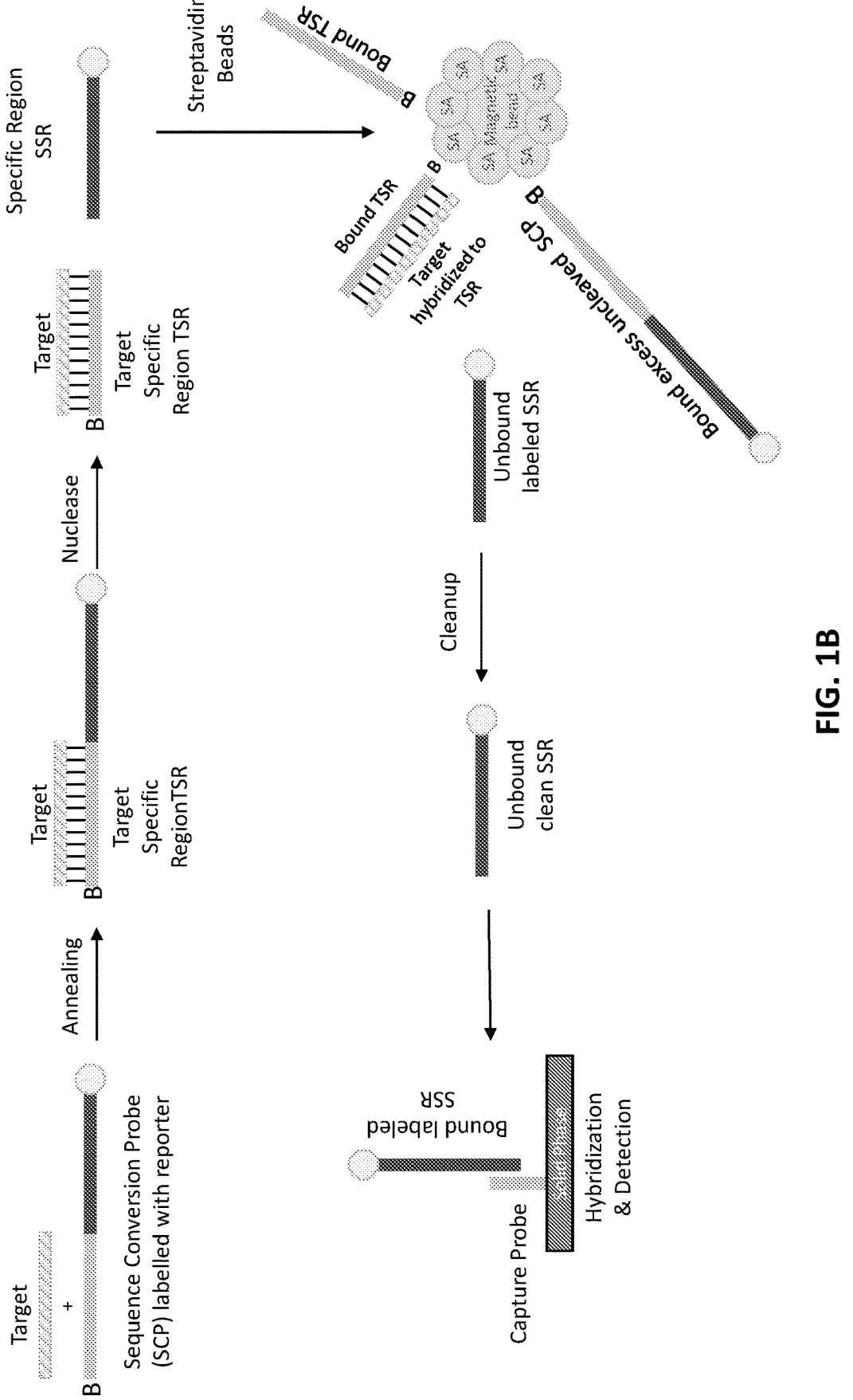

Any of these assays, including the one shown in FIG. 1A, may include the use of multiple SCPs and/or subsets of SCPs. Each subset of SCP may include the same SSR and different TSRs, as will be described in more detail below. In some variations the SSR that is released (cut or cleaved) from the SCP may be unlabeled or not directly labeled. In other variations the SSR may be directly labeled. For example, FIG. 1B shows another sequence conversion method that may be used for detecting a target measurand of interest by converting the target measurand into an engineered signal specific region (SSR), and then detecting the SSR. This reaction is similar to the sequence conversion reaction described in FIG. 1A except that the signal specific region of the sequence conversion probe is pre-labelled with a detectable reporter that may be used for detecting the signal specific region proxy DNA. In FIG. 1B the cSSR is bound to a solid phase (e.g., using a capture probe), and imaged directly, or reacted with an imaging agent. The SSR may be coupled to a reporter that may be directly imaged (e.g., a fluorophore) or indirectly imaged (e.g., an enzymatic reporter, such as HRP, etc.).

Figure 1C:
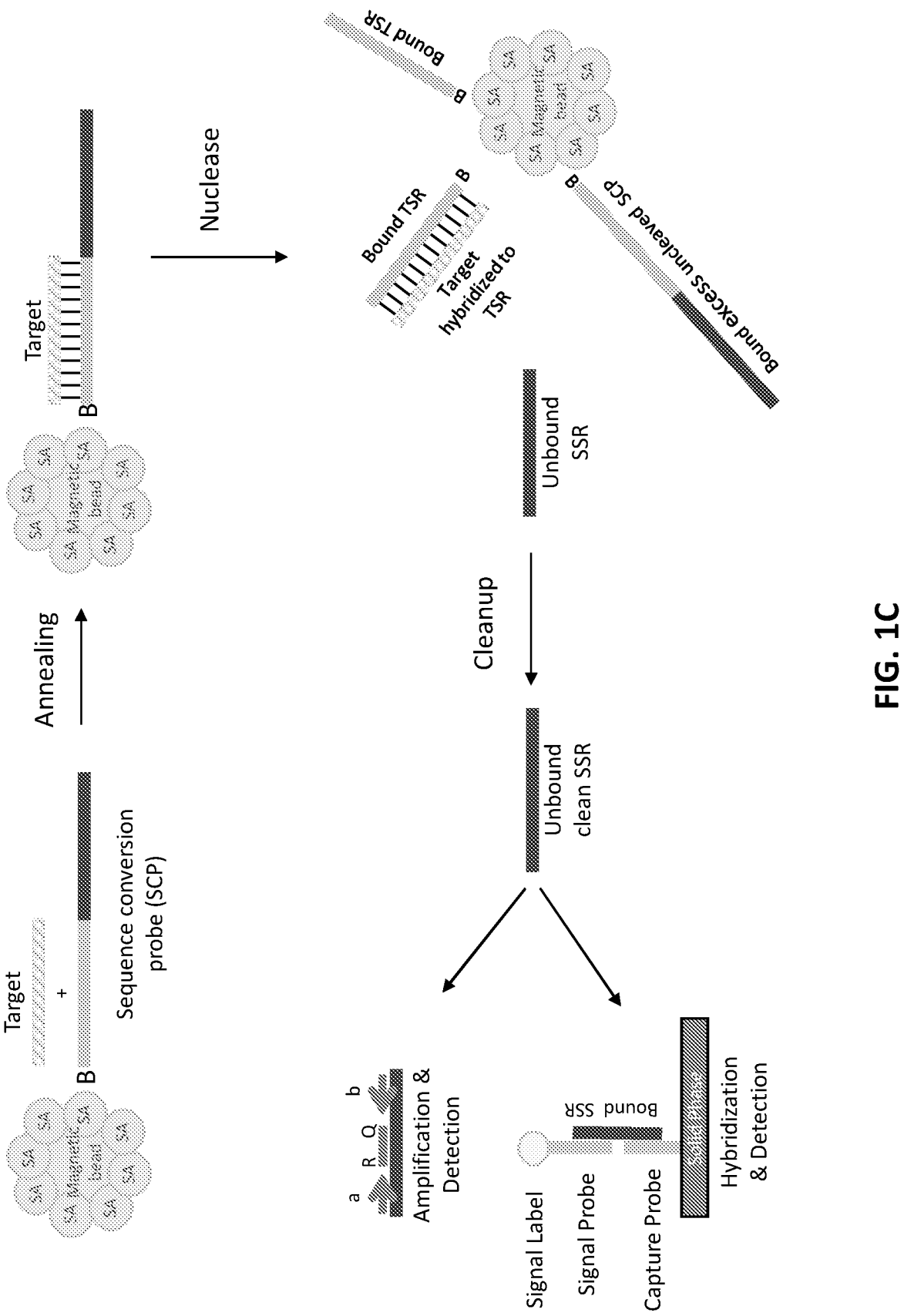

FIG. 1C illustrates another variation of a sequence conversion method similar to those shown in FIGS. 1A-1B. In this example, the SCP is initially bound to the solid phase (e.g., shown as a magnetic bead) and combined with the genetic material (including one or more target measurands).

In this variation the SCPs may then be hybridized to the target measurand, and a nuclease may be used to cleave the SCP, releasing the polynucleotide signal specific region (SSR), while the hybridized target-specific region (TSR) remains bound to the solid substrate via the affinity tag, along with the un-cleaved (and un-hybridized) SCP. Thus, multiple SCPs may be linked to the substrate. After separating the cut SSR from the cut TSR and un-cleaved SCP, the cut SSR may be detected as described above, e.g., by nucleic acid amplification technologies (such as, but not limited to PCR, digital PCR, etc.) and/or hybridization.

Figure 1D:
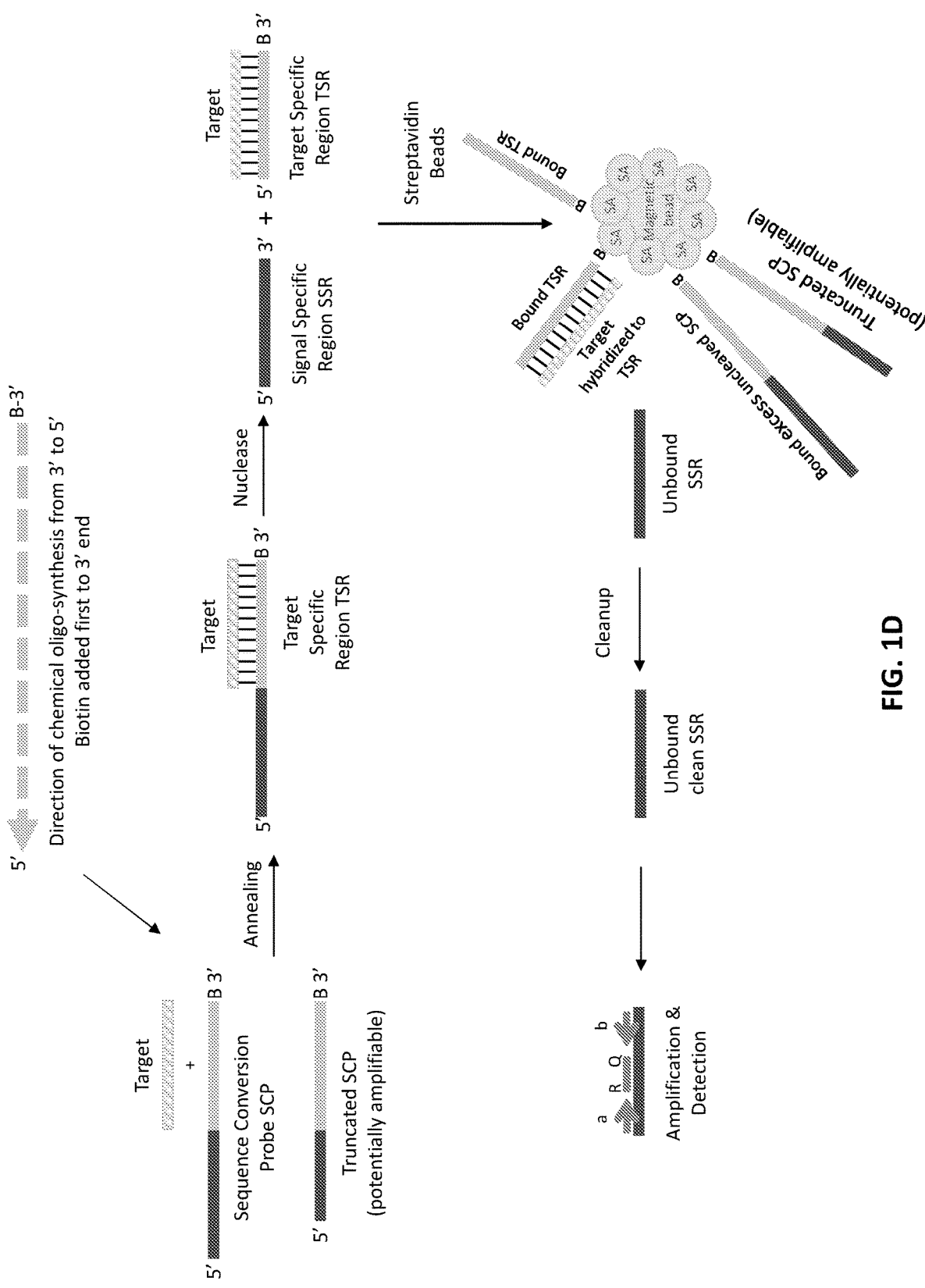
FIG. 1D illustrates another example of a sequence con-version method as described herein.

In FIG. 1A the sequence conversion probe (SCP) is biotinylated with one (or more, as described below) affinity tag (e.g., biotin) on or adjacent to the target specific region (TSR). As described in FIG. 7A, the TSR affinity tag may be at either the 5' or the 3' end of the SCP. In some variations, as shown in FIG. 1D, it may be particularly beneficial to include the TSR and affinity tag at the 3' end, where the SCP is synthesized using a technique (e.g., chemical oligo-synthesis) which extends from the 3' to 5' end, so that the affinity tag such as biotin may be added first to the 3' end. This may ensure that every SCP (and every TSR of an SCP) is biotinylated, even where there are incomplete SCPs. If the affinity tag is added at the end of synthesis (e.g., in some variations, at the 5' end of the SCP), then incomplete SCPs may form (e.g., if synthesis terminates before adding the affinity tag). 3' biotinylation may therefore reduce or eliminate a potentially significant source of background or false positives, which may otherwise result from SCPs that are not removed by the affinity tag. As mentioned above, another possible way to eliminate incomplete, and therefore untagged (by the affinity tag) SCPs would be to use only SCPs bound to a solid phase surface, such as a magnetic bead, as shown in FIG. 1C; these may be washed to remove untagged SCP.

The carryover of SCPs that are not removed by the affinity tag, either because they are not successfully coupled to an affinity tag, or because the un-cut SCP is not sufficiently retained and/or removed by the affinity tag following nuclease treatment (see, e.g., FIGS. 1A-1B) is potentially significant. SSR released from the SCP by the nuclease cutting, otherwise indicating a positive signal, in these examples is indistinguishable from un-cut SCP from which it is derived by many detection techniques, including by PCR. Any carryover of un-cut SCP into a subsequent TaqMan or dPCR may increase background and impact assay performance. For some ultrasensitive clinical applications, such as NIPT, as described herein, even minute levels of SCP carryover may lead to intolerable background signal.

Two potential sources of SCP carryover, and therefore background, include sequence conversion probe that is not bound to an affinity tag (as may occur with truncated SCPs), and sequence conversion probe that includes an affinity tag, but that remains unbound (as may occur with lower affinity or lower retention binding). The issue of SCP carryover is of particular relevance, as in highly sensitive applications such as NIPT, it may be critical to ensure that the final signal is only generated by the released SSR. When sequence conversion reactions are used for NIPT as described in some variations herein, such assays may contain ~200 or more different SCPs per chromosome to achieve significant clinical performance. For example, in cfDNA there may be ~1,000 genome copies per targeted allele in 1 ml of plasma, resulting in 200,000 molecules of SSR per chromosome. With a 50 pM concentration of each SCP in 100 µl (or approximately $6\times10^{11}$ molecules of SCP per chromosome) there is a $3\times10^6$ ratio of SCP:released SSR (per chromosome). For NIPT, as little as a 2% difference in aggregate released SSR from two chromosomes should ideally be detectable for samples with 4% fetal fraction. Thus, the maximal level of SCP carryover that would lead to intolerable background levels may be calculated. A reasonable specification could be that less than 10% of the signal difference between normal and trisomy attributable to the desired released SSR may come from carryover of uncleaved SCP. This translates into very strict tolerances: 10% (max background specification)×2% (copy number difference for 4% fetal fraction)×200,000 (molecules of SSR per chromosome)=400 molecules carryover SCP tolerated. 400 molecules of carryover intact SCP translates into a requirement to remove $400/6\times10^{11}$, or 99.9999999% of the SCP in order to resolve signal within the desired range. This strict tolerance may be highly demanding in practice.

Described herein are methods and compositions (including kits) that may address this. In general, the SCPs provided as part of these methods and compositions may be labeled with an affinity tag (such as biotin) in different configurations: at the 5' end, internal or at the 3' end (and in some variations, internally). 5' end and 3' end biotinylation is described in FIG. 7A. Commercially available HPLC-purified oligos are typically less than 95% pure with many of the impurities being 5' truncated species. Phosphoramidite-based synthesis of oligonucleotides occurs in the 3' to 5' direction and begins with a Control Pore Glass (CPG) amidite at the 3' end. If an affinity tag or label (in this example biotin), is placed at the 3' end, this means that the synthesis may begin with a CPG-biotin. If the tag is placed at the 5' end, it is the last phosphoramidite to be added prior to cleavage from the CPG solid support and deprotection and subsequent purification. In this case, only full-length oligos carry the 5' biotin. It is reasonable to assume that even highly purified 5'-biotinylated SCPs may contain >1% unbiotinylated truncated contaminants which may be detectable by, e.g., PCR, thus causing a background signal. Unbiotinylated SCP may not be removed by streptavidin coated magnetic beads because they lack the biotin required for binding. Since an impurity level of 1% in the synthesized SCPs probes cannot be removed with streptavidin (SA) beads these impurities may result in $6\times10^9$ molecules (e.g., 1% of $6\times10^{11}$ molecules) causing background.

However, in variations in which all of the SCP is labeled with a 3' biotin that is synthesized as described above, all of the probes will have the 3' biotin. This is therefore may be a preferred label configuration. See, e.g., FIG. 1D. In this example, the SCP oligos are synthesized as indicated, with the affinity tag (e.g., biotin) added at the 3' end and the direction of chemical oligo-synthesis proceeding from the 3' end to the 5' end. Thus, even where there are truncated (e.g., incompletely synthesized) SCP, as shown on the far left side, these truncated SCPs are still biotinylated at the 3' end. Following annealing to a measurand target (similar to that shown and described above in FIG. 1A), and nuclease treatment, signal specific regions (SSR) is release by cutting of those SCPs that are hybridized to measurand. Cleaved TSRs and uncleaved SCPs are then removed by binding to a solid phase substrate using the affinity marker, such as streptavidin beads, as shown. The resulting positive signal (unbound SSR) may be separated from the full-length SCP as well as any truncated SCP, allowing accurate amplification and/or detection, as shown (e.g., via PCR).

An alternative variation is illustrated above in FIG. 1C. As mentioned above, the background from unbiotinylated SCP impurities (e.g., truncated SCP that does not include an affinity marker) may also be avoided by pre-binding the SCPs to the affinity partner, such as pre-binding to Strepta-vidin (SA) beads, followed by copious washing, as illustrated in FIG. 1C. If the SCP is synthesized with the affinity tag added at the 3' end, this may eliminate truncated forms of the SCP. Thus, all unbiotinylated probes may be removed. As described above for FIG. 1C, the SCP bound to SA beads (pre-coated beads) may be added to the extracted cfDNA. The genomic target sequences may hybridize to the solid-phase probes. The hybridization step may take longer. Optionally additional SA beads may be added during the restriction digest to bind any biotin-SCP that is released from the initial SA beads.

If greater specificity is desired, addition affinity tags (e.g., orthogonal affinity tags), such as a digoxin, may be included on the SCP near the 5' end to exclude truncated impurities. It must be an orthogonal (i.e. not biotin) so that the 3' biotin-SCP are not removed. It may be near, but not at, the 5' $PO_4$ end so that it does not inhibit ligation.

In general, any of these methods and compositions may include multiple affinity tags, including multiple biotin groups. For example, multiple biotin groups may be sequentially added to the 5' end of the SCP or in some variations the 3' end of the SCP. To increase the strength of binding the avidity of the SCP to bind the affinity partner (e.g., SA) may be increased by using more than one affinity tag (e.g., biotin) per SCP. Avidity refers to the accumulated strength of multiple affinities of individual non-covalent binding inter-actions, such as between an antibody and an antigen, and is commonly referred to as functional affinity. To increase avidity, multiple (e.g. two to four) biotin tags may be added on the SCP which can interact with the four binding sites on each streptavidin (SA). Theoretically, if all four biotins are engaged in binding, the $K_d$ would be approximately $10^{-60}$ M, more than sufficient for the estimated stringency described above.

Even though the affinity of the biotin-streptavidin inter-action is extremely strong, with a best-case disassociation constant ($K_d$) of $10^{-15}$ M, a small amount of the biotin-SCP probe may still remain unbound, because even this extremely strong interaction is still an equilibrium between bound and unbound species. The theoretical level of unbound biotin-SCP was calculated under the expected reaction conditions at the reported ($10^{-15}$ M) and 10-fold lower $K_d$ ($10^{-14}$ M) as shown in Table 1.

| [streptavidin], M* | [biotin-SCP], M** | $K_d$, M | molecules free biotin-SCP |
|---|---|---|---|
| 1.00E−06 | 3.00E−08 | 1.00E−15 | 1,862 |
| 1.00E−06 | 3.00E−08 | 1.00E−14 | 18,619 |
| 1.00E−06 | 3.00E−08 | 1.00E−60 | 0 |

The last row of Table 1 illustrates the theoretical effect of including four biotin on, e.g., the 3' end of the SCP.

There are various well-known biotin modifications that may be added to the 3',5' end or placed internally, such as a standard (C6 linker) biotin, biotin-dT (which can be placed internally), and a dual biotin modification resulting in two functional biotin groups, which act to increase biotin-streptavidin binding affinity, and may be used for applications requiring high sensitivity, as described above.

Any of the methods and compositions (e.g., kits) described herein may provide cleavage of the SCP to release the SSR immediately adjacent to, or as close as possible (e.g., within 1 bp, within 2 bp, within 3 bp, within 4 bp, etc.) to the TSR that is hybridized to measurand, depending on the nuclease used. For example, restriction enzymes may be used, as described herein. Restriction enzymes may specifically cleave double stranded DNA. Cleavage specificity may be enhanced by cutting the double stranded TSR-target DNA as close as possible to the transition to the single stranded SSR. By engineering the cut-site to be as close as possible to the Y-intersection of double to single-stand DNA (e.g., the TSR-SSR boundary) the specificity of the DNA cutting may be enhanced. In some variations Type IIS restriction enzymes, such as BsaI or BspQI, which cleave outside of their recognition sequence to one side, and thus allow cleavage closer to the Y-transition from the double stranded TSR to the single stranded SSR, may be used. In one example, taking the enzymological requirements into consideration, the cut site can be moved to within two bases to the intersection. For example, BspQI may be used by targeting the BspQI recognition site as part of the TSR, at the TSR-SSR boundary.

In any of the sequence conversion methods (and assays including the sequence conversion method) multiple SCPs, directed to a variety of target measurands and including a subset of different SSRs may be used to consolidate groups of different target measurands by category or class identified by a common SSR.

For example, any of these assays may include a plurality of different sequence conversion probes (SCPs) that may be combined with a sample mixture of genetic material that includes target measurands. The combined mixture may be referred to as an assay mixture. As described above, each SCP may include a polynucleotide target-specific region (TSR), an affinity tag, and a signal specific region (SSR). The SSR includes an engineered polynucleotide marker. The SCPs may be configured to hybridize to a number (x) of different targets (e.g., may have different TSRs). Within the plurality of SCPs, different TSRs for which their target sequences (e.g., target RNA, target DNA, etc.) share a common class or category may have the same SSR. Thus, the number of different SSRs (y) may be less than the number of TSRs (e.g., there may be 2 time as many or more TSRs as SSRs, 3× or more as many, 4× or more as many, 5× or more as many 6× or more as may, 7× or more as many, 8× or more as many, 9× or more as many, 10× or more as many, 15× or more as many, 20× or more as many, 25× or more as many, 30× or more as many, 40× or more or many, 50× or more or many, 100× or more or many, 200× or more as many, 300× or more as many, etc.). Thus, these assays may be reductive assays, reducing a large number of diverse target measurands to a smaller number of uniform SSRs (e.g., engineered polynucleotide markers). The uniform SSRs may be configured to represent a category to which subsets of the target measurands are a member.

Figure 2:
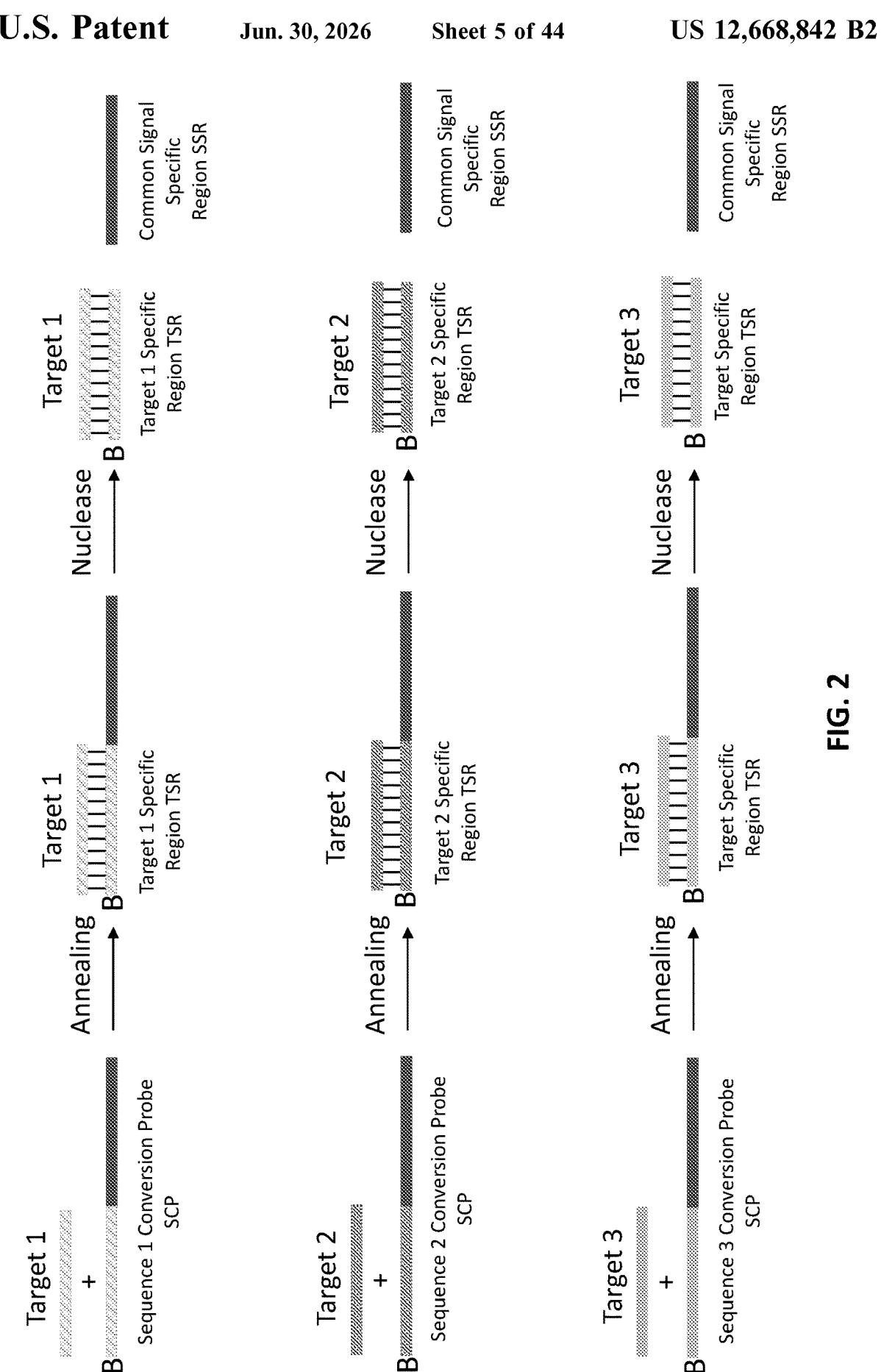
FIG. 2 illustrates the use of a sequence conversion method as described herein to consolidate signaling from multiple target measurands to a single signal using a subset of common signal specific regions (SSRs) on the sequence conversion probe.
Figure 4:
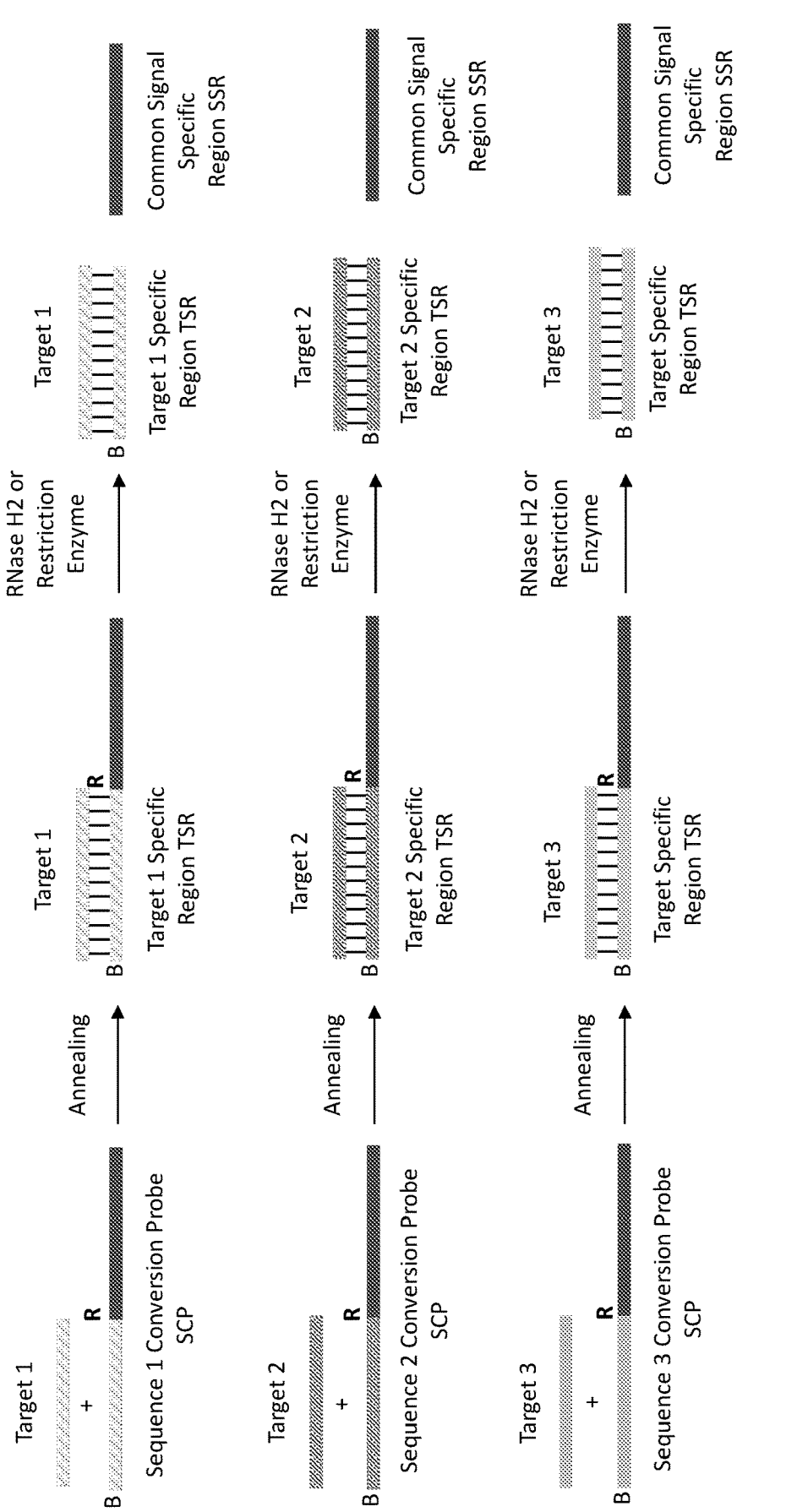
FIG. 4 is another example illustrating consolidation of a multiple different target measurands using a sequence conversion method such as the one illustrated in FIG. 3.

FIG. 2 illustrates one example of an assay in which three different measurands (Target 1, Target 2, Target 3) all share a common signal specific region (SSR). Thus, the detection of the common SSR, e.g., by detecting the engineered polynucleotide marker on each SSR, may signal the presence of any of Target 1, Target 2, or Target 3. This method may reduce three sequences into a single sequence. Other consolidations are possible, and additional SSRs may be used for different target measurands in the same solution (e.g., the same assay mixture). FIG. 4 shows a similar reduction using another variation of a sequence conversion method. In this example, Target 1 and Target 2 are consolidated into a first SSR (SSR 1), while Target 3 is converted to a second SSR (SSR 2). In addition, in this example, the SCP may include a ribose in or adjacent to the TSR providing a site for cleaving the SCP, for example by RNase H2, which binds specifically to RNA-DNA duplexes and cleaves the RNA strand; the ribose in the SCP is recognized by the RNase H2 as the RNA strand and may therefore be cleaved.

Figures 3, 5:
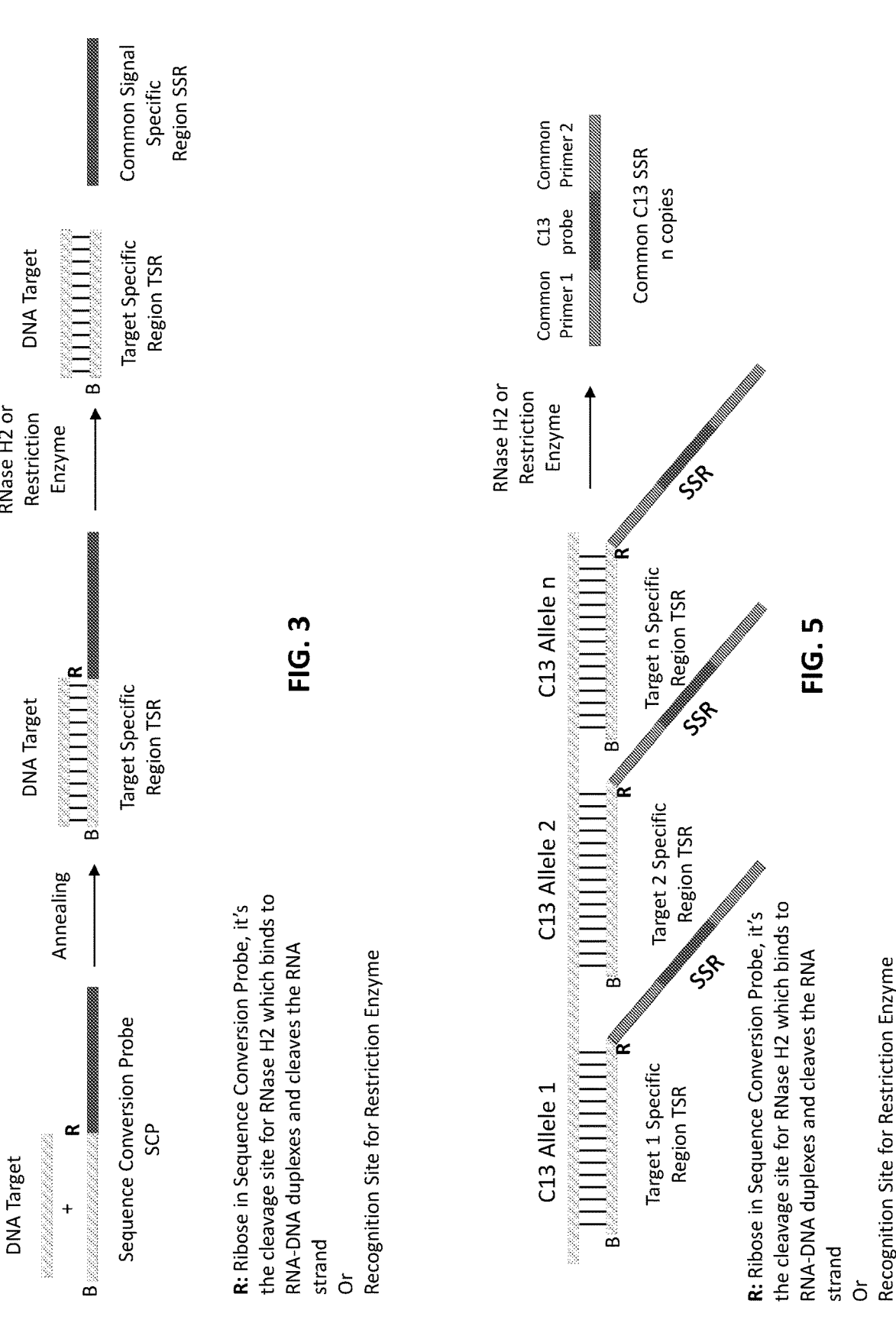
FIG. 3 schematically illustrates another example of a sequence conversion method in which the sequence conversion probe includes a ribose to form one or more cutting sites between the target-specific region (TSR) and the signal specific region (SSR). This variation may use, e.g., RNase H2.
FIG. 5 is another example of a sequence conversion method that may be used for increased sensitivity when detecting a polynucleotide target (e.g., chromosome, gene, etc.) by including multiple sequence conversion probes (SCPs) having a same (e.g., common) signal specific region (SSR) and different target measurands sharing a common desired category (e.g., chromosome, gene, etc.), shown in this example as different alleles of a common chromosome. This may provide linear amplification.

FIG. 3 illustrates the principle of operation of an assay using a nuclease that specifically cuts DNA-RNA complexes. In FIG. 3, the assay uses RNase H2 nuclease to cleave the SSR from the SCP when the target-specific region (TSR) of the SCP is hybridized to the target measurand, shown here as a DNA target. As discussed above, the SCP includes a ribose forming a cleavage site for RNase H2 when bound to the target measurand. In general RNase H2 binds to RNA-DNA duplexes and cleaves the RNA strand. The cut SSR (cSSR) released may contain a small portion of the sequence part of the TSR, caused by the specific require-ments of RNase H2 for cleavage and in addition might be part of the assay design. In FIG. 3, the method is similar to the sequence conversion method described in FIG. 1A except that the nuclease recognition site is a ribose ("R") in the target-specific region of the sequence conversion probe which is otherwise DNA. Nuclease RNase H2 binds to RNA-DNA duplexes (in this case at the "R") and cleaves the sequence conversion probe at the RNA ("R"), breaking the double stranded region where the target measurand and target-specific region (TSR) of the sequence conversion probe are hybridized from the single stranded region, the cleaved signal specific region or cSSR. In this example, the cSSR contains a small part of the target-specific region (TSR). The cleaved signal specific region can be analyzed using amplification and detection or hybridization and detec-tion, such as shown in FIG. 1A, or can be pre-labeled with a signal label such as shown in FIG. 1B and analyzed.

These examples (e.g., FIG. 2 and FIG. 4) illustrate how the sequence conversion reactions described herein can be used to assay multiple different targets using the same signal specific region proxy DNA. FIG. 2 shows three different target-specific regions (TSRs), one for each target mea-surand (target 1, target 2, and target 3). The SSR is the same for all three sequence conversion probes in this example; the sequence is common to all three sequence conversion probes. This assay may follow the steps shown in FIGS. 1A-1C, and the reactions shown can be carried out in a single reaction vessel. Since all three reactions (or more) produce the same signal specific region (SSR), the detection steps, e.g., amplification and detection or hybridization and detection, can be optimized for the SSR (or a plurality of SSRs, which may be engineered to have similar detection properties including shared primers, common range of lengths, etc.). While shown here for three target measurands, this sequence conversion method can be extended to more than 3 target measurands (e.g., up to 4, up to 5, up to 10, up to 20, up to 50, up to 100, up to 500, up to 750, up to 1000, up to 1200, up to 1500, up to 2000, etc., at least 3, at least 4, at least 5, at least 10, at least 20, at least 50, at least 100, at least 500, at least 750, at least 1000, at least 1200, at least 1500, at least 2000, etc., including any number between these numbers). To carry out the assay, each sequence conversion probe may include an engineered polynucleotide marker which may include (or may be part of another, possibly adjacent, region of the SSR) one or more primer regions. As mentioned, the SSRs may be the same for a subset of (or for all in some variations) of the SCPs. The subset of SCPs may therefore have different TSRs and can correspond to subsets of TSRs that share properties placing them into a class (a detection class).

Examples of detection classes for target measurands include chromosomes (e.g., different genes on the same chromosome or groups of chromosomes), genes (e.g., dif-ferent alleles of a same gene), genetic pathways (e.g., different genes in a genetic pathway), exons (e.g., different exons of a same gene), pathogens (e.g., different genes/ alleles, etc. of a common pathogen, including virus), differ-ent mutations known to drive cancer (e.g. lung cancer), or the like. Any grouping of target measurands may be included with a common engineered SSR.

For example, for an assay for non-invasive prenatal testing, the plurality of subsets of SCPs could correspond to different chromosomes so that for each chromosome (within each subset) a plurality of different TSRs could be directed to different parts of a single chromosome and share a same SSR.

FIG. 5 illustrates another example of a sequence conver-sion method in which multiple sequences (multiple target measurands) are alleles of the same target (e.g., a pathogen) and all of SCPs have different TSRs but share the same signal specific region (SSR). Detection sensitivity may be increased by targeting several alleles (subsequences) of the target, such as a pathogen. RNA and/or DNA targets may be used. In this example, the SSR is shown for detection and quantitation of human chromosome 13, e.g., for detecting trisomy 13 although this principle can be extended to any category (e.g., chromosome, gene, pathway, pathogen, can-cer mutations, etc.) or other region of DNA of interest and can be used to detect chromosomal additions (e.g., trisomy), deletions, and normal. In this example, the SSR includes an engineered polynucleotide marker ("C13 probe") and a forward primer region (common primer 1) and reverse primer region (common primer 2) to which primers may be hybridized. In practice, multiple different SCPs with differ-ent sequence conversion probes (SCP) for different target measurands on chromosome 13 (C13 allele 1, C13 allele 2, and C13 allele n) may be used. C13 allele n represents that any number (n) of additional sequence conversion probes can be included. The SSR is the same for the different C13 probes. A different SSR could be used for another mea-surand, such as for another chromosome or another part of chromosome 13. This method is similar to the method shown in FIG. 2, except that each sequence conversion probe includes a ribose (R) for cleavage by RNase H2 as described above, alternatively it could contain a recognition site for a restriction enzyme. Other nucleases (with or without a ribose) may be used. Since the C13 allele 1, C13 allele 2 and C13 allele n reactions produce the same SSR, the detection steps (e.g., amplification and detection or hybrid-ization and detection) can be optimized for a single SSR or a category of SSRs when additional groups (e.g., chromo-somes) are tested. In some variations, this sequence conver-sion method can be extended to more than 3 targets (e.g., up to 4, up to 5, up to 10, up to 20, up to 50, up to 100, up to 500 or at least 3, at least 4, at least 5, at least 10, at least 20, at least 50, at least 100, at least 500, etc. to any number between these numbers), and/or any additional number of sub-sets having different SSRs.

Figures 6A, 6B:
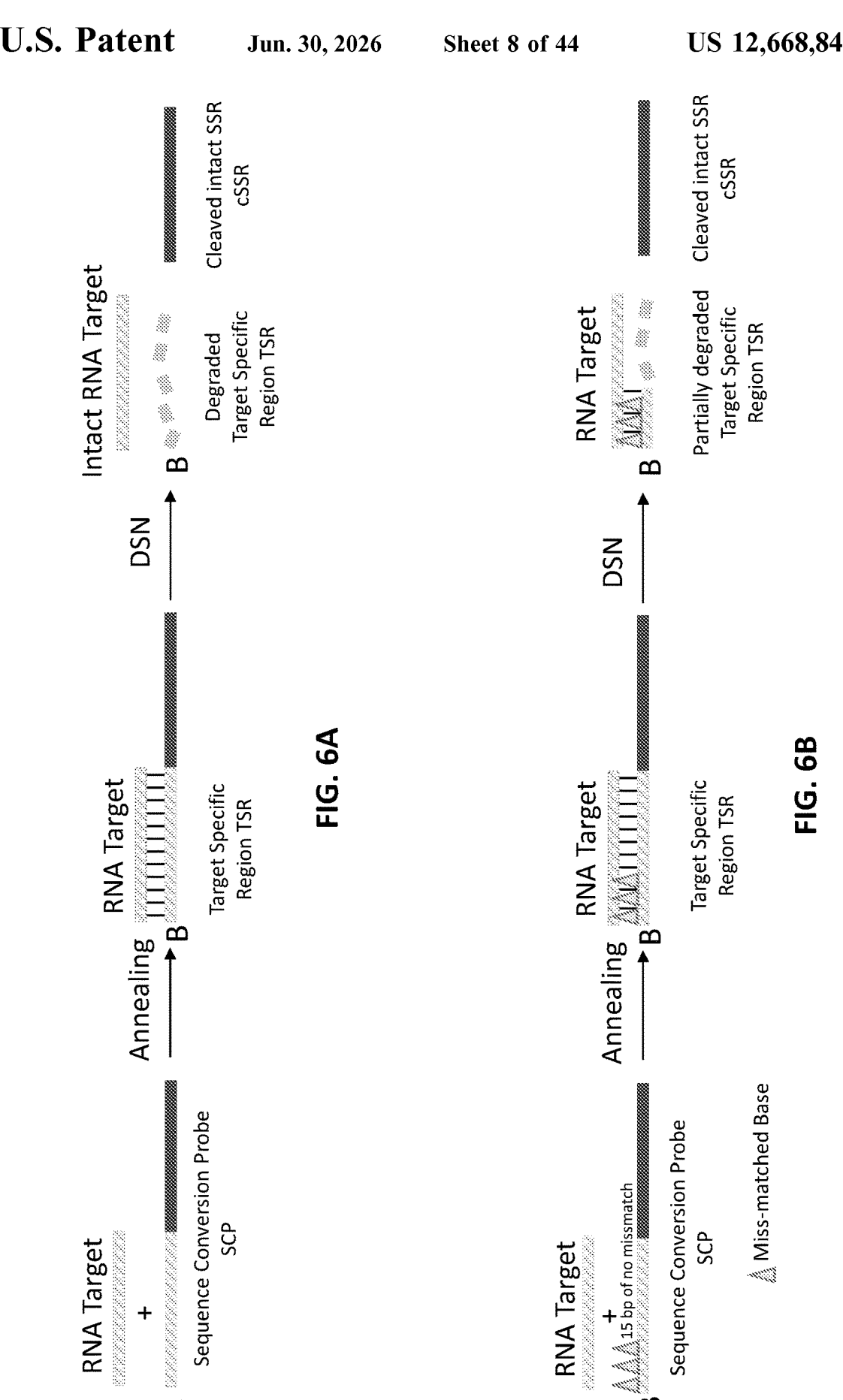
FIG. 6A illustrates an example of a sequence conversion method in which the target measurand is an RNA, and the RNA sequence may be converted to a DNA sequence. This reaction can be driven by a nuclease, e.g. Duplex Specific Nuclease (DSN). In the variation shown in FIG. 6A the sequence conversion method may allow amplification of the RNA by DSN destroying the target-specific region (TSR) of the sequence conversion probe (SCP) when releasing the SSR (e.g. forming cut SSR or cSSR).
FIG. 6B illustrates an example of a sequence conversion method similar to that shown in FIG. 6A, in which the target measurand (e.g., RNA target measurand) is not recycled, by including mismatches in the target-specific region (TSR) of the sequence conversion probe when using a duplex specific nuclease (DSN) as the nuclease for the sequence conversion method.

FIG. 6A illustrates another example of a sequence con-version method, configured to detect an RNA target using a duplex specific nuclease (DSN). This example also illus-trates conversion of the RNA target measurand into a DNA signal specific region (SSR). In FIG. 6A, the RNA target measurand is hybridized to the SCP having a target-specific region (TSR) and this hybridization allows the DSN to cleave the SSR from the SCP, releasing the SSR (into a cut SSR or cSSR) and further degrading the TSR of the SCP. This also releases the RNA target measurand back into the solution (e.g., the mixture) where it may again bind to another copy of the SCP and release cSSR. This may linearly amplify the RNA target measurand (into a DNA cSSR); the amplification may be limited by the concentration of SCP and/or the hybridization/annealing conditions, including the temperature. A similar method may be used for DNA/DNA duplexes (e.g., using a DNA test) with RNase H2 in which the TSR includes multiple ribonucleases as described (e.g., in FIG. 9).

In some variations it may be desirable to remove the target material (e.g., RNA target measurand) from the reaction. FIG. 6B illustrates one example of a method of doing this, in which the RNA target measurand is prevented from being released after the nuclease (DSN) cuts releases the cSSR by including one or more (e.g., a plurality) of mismatches between the bases of the RNA target measurand and the TSR of the sequence conversion probe. DSN discriminates between perfectly matched short DNA-DNA duplexes (10-12 bp) and duplexes of the same length with at least one mismatch. For example, DSN requires at least 10 bp DNA or 15 bp DNA-RNA perfect duplex for cleavage. Thus, in FIG. 6B, the use of engineered mismatching to the RNA target measurand may allow only partially degradation of the TSR, so that the target measurand may remain hybridized to the TSR and can be separated from the cSSR as described above.

The sequence conversion probes described in FIGS. 1A-6B typically include both a target-specific region (TSR) and a signal specific region (SSR), as shown in FIG. 7A. The TSR and SSR may be combined and the TSR portion may be coupled to an affinity tag, as described above. The affinity tag and TSR may be at the 5' or the 3' end, with the SSR at the opposite end, as shown in FIG. 7A. In general, the SSR is a synthetic sequence that is configured so that it does not bind to genetic material in the sample. The SSR may include an engineered polynucleotide marker. This marker may be any length, e.g., between 30 and 500 bp (e.g., between 40-400 bp, between 40-300 bp, between 40-200 bp, between about 50-90 bp, between about 50-80 bp, etc.), and may be adjacent and/or may include one or more primer regions (to which one or more primers may hybridize) for amplification and/or detection. For example, in some variations the engineered polynucleotide marker may be flanked by a forward primer region.

FIG. 7B illustrates examples of sequence conversion probes (SCPs) that are configured for use with DNA and include one or more Ribonucleotides. For example, an SCP for a DNA target measurand in some variations may be cleaved (when hybridized to its target measurand) by a nuclease such as RNase H2. In FIG. 7B the ribonucleotide is shown by the "R" in the sequence, the R can also stand for the recognition site of a restriction enzyme. Any of these SCPs may also include one or more chemical linkers. As shown in FIG. 7B, the position of the ribonucleotide can be selected on the TSR within the RNase H2 activity constraints.

FIG. 7C schematically illustrates examples of SCPs for use with either DNA or RNA target measurands. As described above in FIGS. 6A and 6B, when the TSR hybridizes to a target measurand and a nuclease such as DSN is used, the TSR may be degraded when releasing the cleaved SSR (cSSR). In some variations, in which the TSR includes partial mismatches, the partially degraded region may not be degraded after the SCP has been cleaved by the DSN.

As mentioned above, when only the TSR is degraded (e.g., by DSN or RNase H2) the intact target measurand may be released and allowed to hybridize to another copy of the SCP. This is illustrated in FIG. 8, showing the use of duplex specific nuclease (DSN) with amplification of the reaction. FIG. 9 shows a parallel variation, using RNase H2, in which the DNA target measurand may be recycled to amplify the signal (cSSR). In FIG. 9, amplification can be achieved by either one or more ribonucleotides in the TSR to allow more complete degradation when RNase H2 or a similar nuclease (that degrades the RNA of an RNA/DNA duplex). If only a single ribonucleotide is used, the Tm of the probe and/or reaction temperature may be adjusted to dissociate the target measurand after probe cleavage and allow amplification by rebinding of the target measurand to another Sequence Conversion Probe (SCP).

Figure 10:
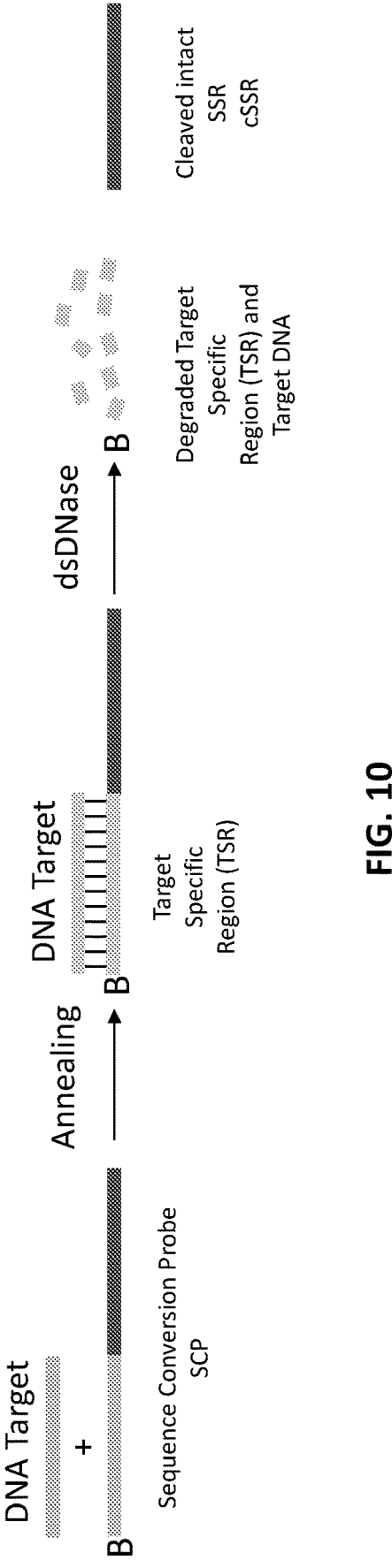
FIG. 10 illustrates another example of a sequence conversion method in which the DNA target measurand and the TSR are degraded (the nuclease used is a double stranded DNase (dsDNase)), releasing the cleaved or cut signal specific region (SSR). In some variations of the sequence conversion method it may be desirable to translate a target measurand into an SSR without amplification (e.g., in a 1:1 ratio).

Alternatively, FIG. 10 shows an example in which the DNA target measurand is degraded with the TSR by the use of a double-stranded DNase (dsDNase), leaving intact the cut SSR (cSSR). In some variations it may be desirable to provide a 1:1 conversion between the target measurand and the SSR. For example, the SSR, rather than the original target measurand, may then be amplified, and the SSR may be engineered to prevent amplification bias. Restriction enzymes typically cleave both strands of a DNA duplex, thereby destroying the target measurand and ensuring release of exactly 1 SSR for 1 target measurand.

For example, any of the methods and compositions (e.g., kits) described herein may be used to provide input into a procedure including digital PCR to provide quantitative data.

Figure 13:
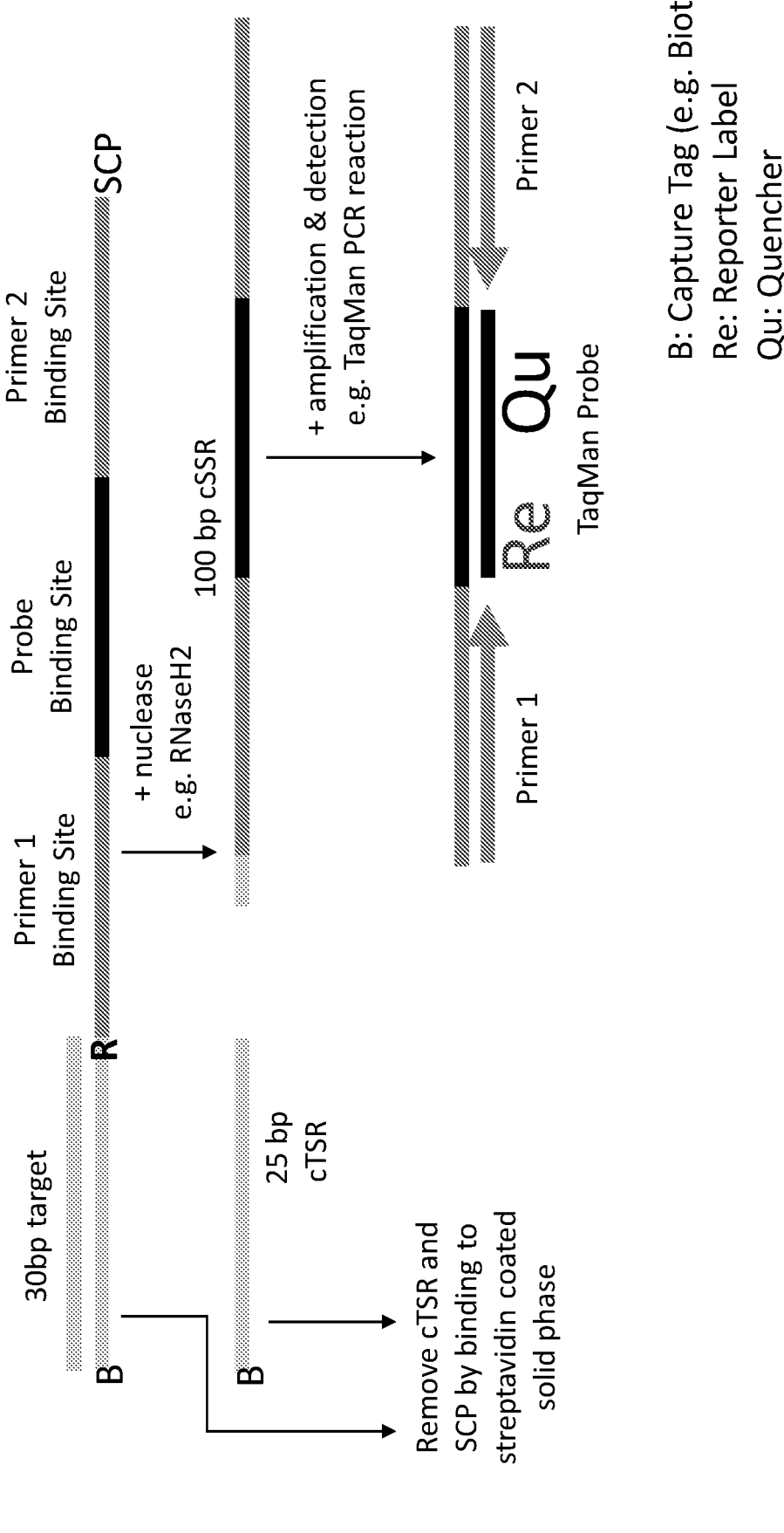
FIG. 13 illustrates the use of a sequence conversion method as described herein for detection of short target measurands, such as microRNAs (e.g., polynucleotides having a length of less than about 40 base pairs, e.g., 38 bp, 35 bp, 32 bp, 30 bp, etc., which are otherwise difficult or impossible to use with other detection techniques such as TaqMan assays). The sequence conversion method may convert the short target measurand into a signal specific region (SSR) that may be directly detected or may be amplified and detected.

The methods and compositions described herein may also be used to detect very short target measurand sequences. For example, FIG. 13 illustrates one method for identifying a short (e.g., 30 bp or smaller) target measurand. Short target measurand sequences (e.g. 30 bases or smaller) may be difficult to detect with existing assays, such as the TaqMan assay, which requires two primers and a probe and a target measurand length of more than 60 bases is desirable to accommodate the space needed for two primers and a probe. Thus, this very simple assay may not be readily used for smaller polynucleotides, such as microRNAs. In FIG. 13, the SCP is configured so that the SCP includes a target-specific region (TSR) that is configured to hybridize to a small (e.g., 30 bp) target measurand; exposure to a nuclease may then release the signal specific region (SSR) that is substantially longer (e.g., 100 bp) and may include primer binding regions (primer binding region 1 and primer binding region 2) that flank the engineered polynucleotide marker. As shown, a TaqMan probe and primers may hybridize with the engineered polynucleotide marker and flanking primer regions to allow detection (e.g., by release of the reporter label, Re, from the proximity of the quencher, Qu, during amplification. The un-hybridized SCP may be removed by the affinity tag as described above.

Figure 14:
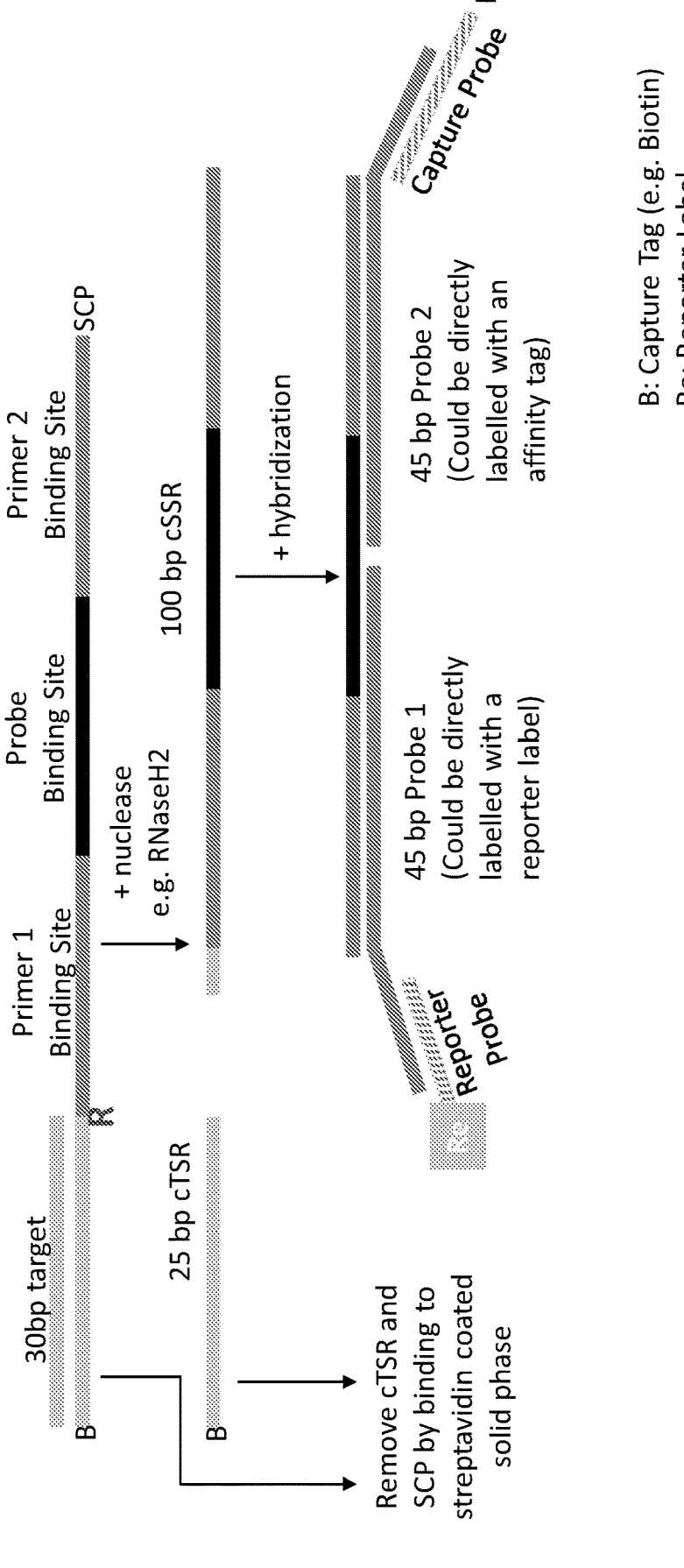
FIG. 14 illustrates another example of a sequence conversion method that may be used for detection of short target measurands, similar to that shown in FIG. 13. Hybridization reactions can require a minimum length for oligonucleotide to be detectable. Analytes too short for certain hybridization assays can be converted into longer ones to become useful substrates for these assays.
Figure 15:
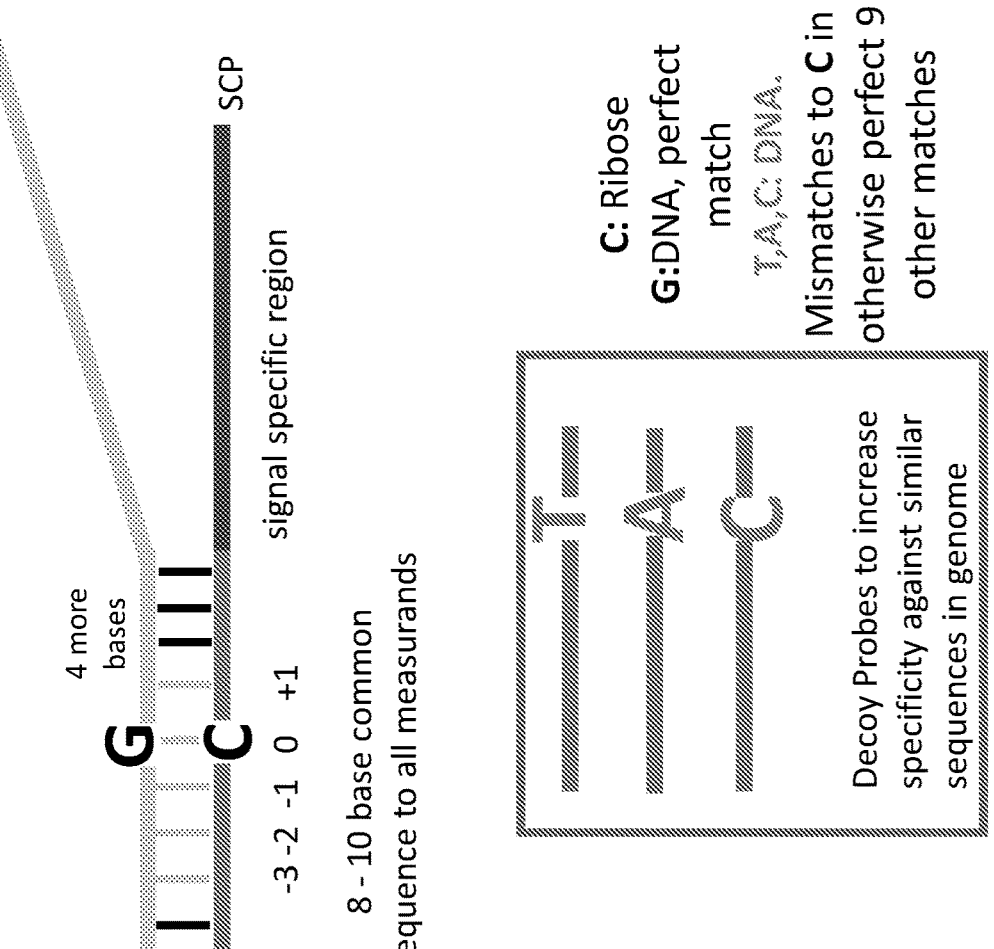
FIG. 15 illustrates one example of a sequence conversion method in which the nuclease is a Ribonuclease H, such as RNase H2 (or RNase HII). The sequence conversion probe (SCP) may include a ribose in the target-specific region or the region between the target-specific region and the signal specific region.

A similar technique may be used for direct detection of small target measurands, as shown in FIG. 14. In this example the short target measurands are detectable by hybridization to a reporter probe. Short target measurand sequences (e.g., e.g. 30 bases) may also be difficult to detect by highly sensitive and specific hybridization technologies, such as the "nCounter System," which requires a target measurand of ~100 bases in length. In general, in the figures (unless specified otherwise) the sizes of the probes and components are for illustration purposes only and can be adapted to the needs of the assay.

In FIG. 14, the SCP includes a target-specific region (TSR) that hybridizes to the small (30 bp or less) target-specific regions and when exposed to the nuclease, releases the (longer) signal specific region (SSR). The release SSR may be separated from the un-hybridized SCP and probed, e.g., using a reporter probe (e.g., labeled with a reporter label) and in some variations a capture probe, as shown.

Figure 16:
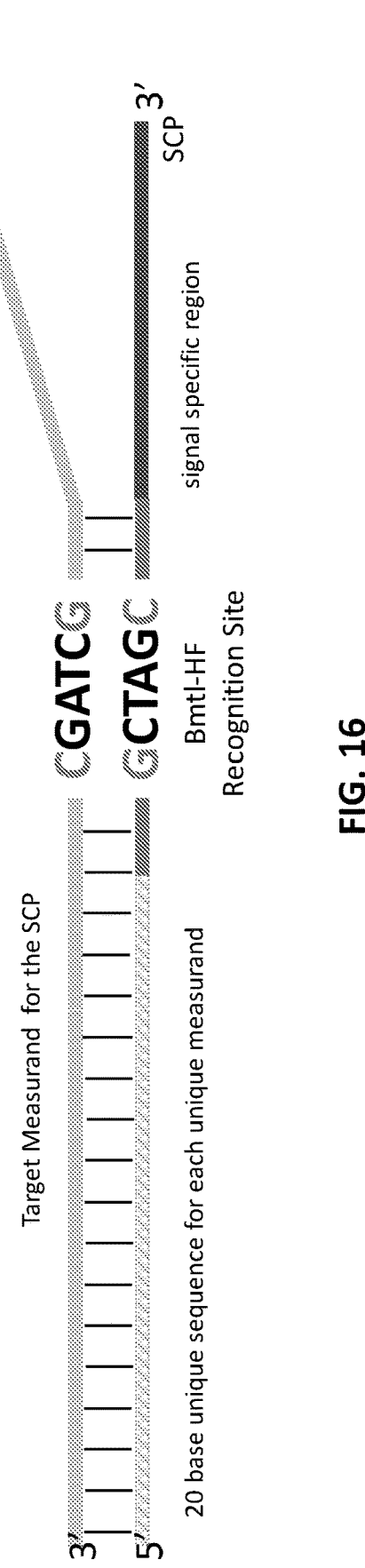
FIG. 16 illustrates one example of a sequence conversion method in which the sequence conversion probe is configured to be cut by a restriction enzyme to release the signal specific region. The restriction endonuclease may be matched to a recognition site in the target-specific region.

As mentioned above, in some variations the methods described herein for performing the sequence conversion method may include a restriction endonuclease as the nuclease. This is illustrated, for example, in FIG. 16. In this example, the recognition site for the nuclease may be part of the target-specific region (TSR) of the sequence conversion probe (SCP). In FIG. 16, the restriction site is located near the 5' end of the region of the target measurand sequence. Thus, the target measurand may be chosen to include one of a specific subset of restriction enzyme recognition sites (in FIG. 16 the site is a BmtI-HF recognition site) that can be used to readily cleave the signal specific region (SSR) of the SCP once it has bound to the target measurand. Over 280 restriction enzymes are commercially available (e.g., from New England Biolabs) allowing selection of different recognition sites and other enzyme properties. In some variations, the enzyme (restriction endonuclease) may work at a temperature range (37° C.-70° C.), BsaI being one example. The methods described herein may provide sufficient flexibility when choosing the target sequence so that one can bioinformatically select a sequence recognition site fitting an enzyme. Different length recognition sites may be used, and unspecific cutting may be avoided.

In general, the target-specific region may be designed so that binding to the target measurand is optimal. For example, the TSR may be configured to bind to at least a 5 mer and can be directed to the coding (gene) portions of the genome. The sequences may be restricted to contain at least half GC (so 3 to 6 for 6 mers). When identifying good target measurand regions, regions that are repeated (e.g., multiple copy regions) may be preferred, because they may increase the overall signal or may be avoided if e.g. accurate chromosome counting is desired.

FIGS. 17-18 shows another example of a sequence conversion method in which the nuclease is a 5'-3' nuclease. The 5'-3' nuclease may be part of a DNA polymerase enzyme (e.g. Taq polymerase). In this example, the signal specific region is released when the target measurand is bound to the target-specific region in the presence of the 5'-3' nuclease, as shown in FIG. 17-18. The affinity tag in this example is on the 3' end of the SCP, so that un-hybridized SCP can be separated from the released SSR, as described above. As an alternative to the 5'-3' nuclease, a Flap-endonuclease (e.g., FEN-1) may be used.

Figures 19A, 19B, 19C:
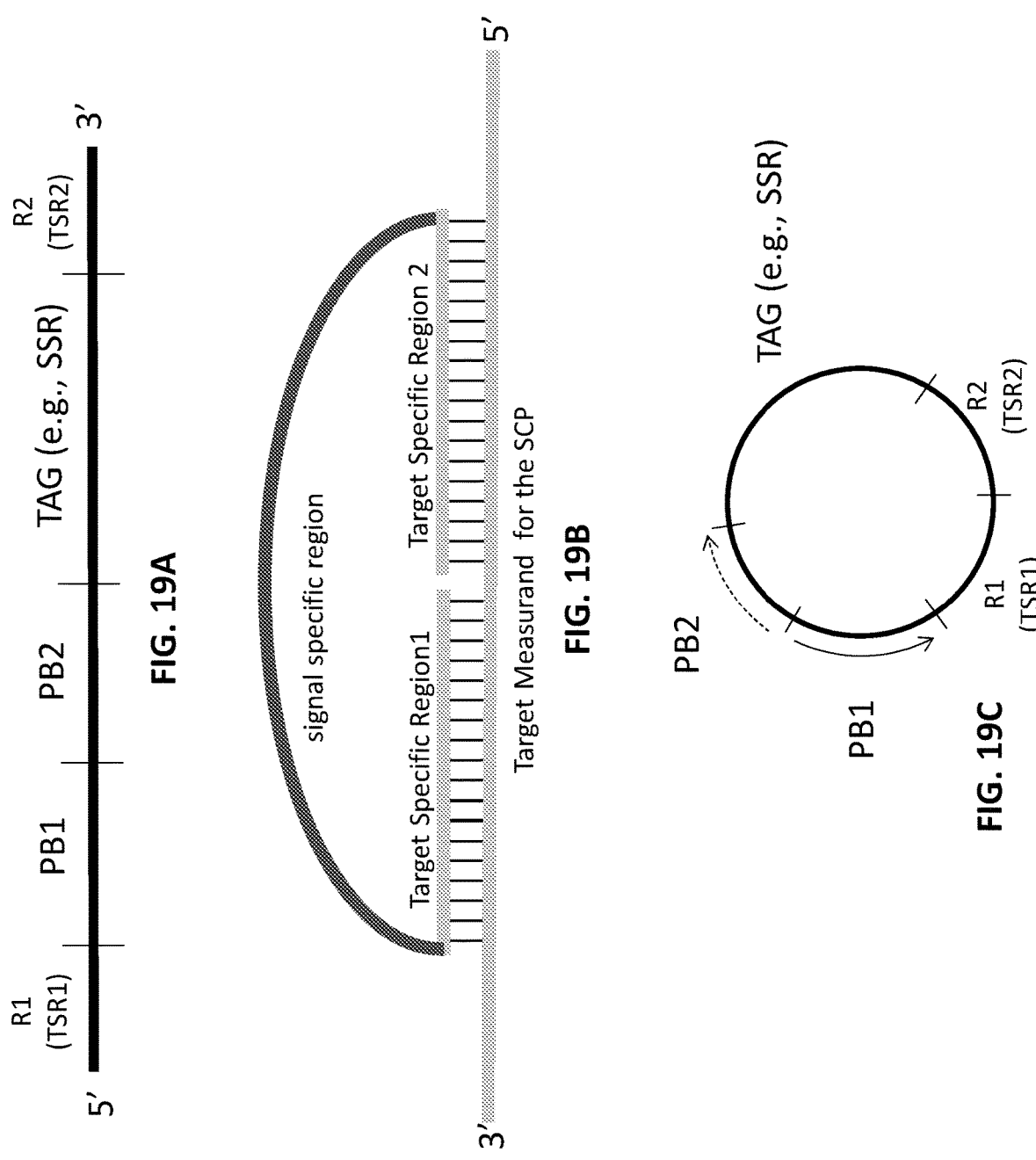
FIGS. 19A-19C illustrates one example of a sequence conversion method variation in which the sequence conversion probe is configured as an inversion probe (in some variations, a padlock probe). In this example the sequence conversion probe includes a first target-specific region (TSR1) at a first end and a second target-specific region (TSR2) at a second end; TSR1 and TSR2 hybridize to adjunct regions of a target measurand. Each probe includes a target specific region that may be common to multiple target measurand regions.

FIGS. 19A-19C and 20 illustrate another example of a sequence conversion assay. In this variation the sequence conversion probe is configured to be an inversion probe (e.g., a padlock probe) that may be used in an analogous manner to the other embodiments of the SCA described above. This variation of a sequence conversion probe may be referred to as a circularizing sequence conversion probe (cSCP). For example, the cSCP may include a pair of target-specific regions (in this embodiment a pair of terminally located target-specific regions) and a signal specific region (SSR). The signal specific region may also include one or more primer regions for hybridizing to a primer. For example, in FIG. 19A, the SCP is shown schematically, and includes an R1 (first target-specific region, TSR 1) and R2 (second target-specific region, TSR 2) that are specific for the target subsequences of the target measurand. TSR1 may be sense and TSR2 may be antisense, so that when hybridizing to the target measurand (as shown in FIG. 19B) the SSR forms a circularization complex with the target measurand. The circle is closed by ligation and the remaining linear probe can be cleaned up with exonuclease. The cSCP also includes a first primer region (PB1, to hybridize to Primer 1) and a second primer region (PB2, to hybridize to Primer 2), and the engineered polynucleotide marker (TAG) portion of the SSR, which may be configured as, e.g., a TaqMan probe binding site for some variations.

For example, in some variations the cSCP may be configured for use with NIPT and may include first and second target-specific regions (e.g., R1 & R2) that are the selected target sequences on the chromosome. PB1 and PB2 may be a universal primer (e.g., one pair), and the TAG region may be a specific TaqMan probe for each chromosome (e.g., 3 in total, one for each of chromosomes 13, 18 and 21).

In use, the cSCP may be hybridized to the target measurand as shown in FIG. 19B, forming a circularization complex. This complex may be circularized by the use of a circularization agent, such as a ligase, as shown in FIG. 19C.

Figure 20:
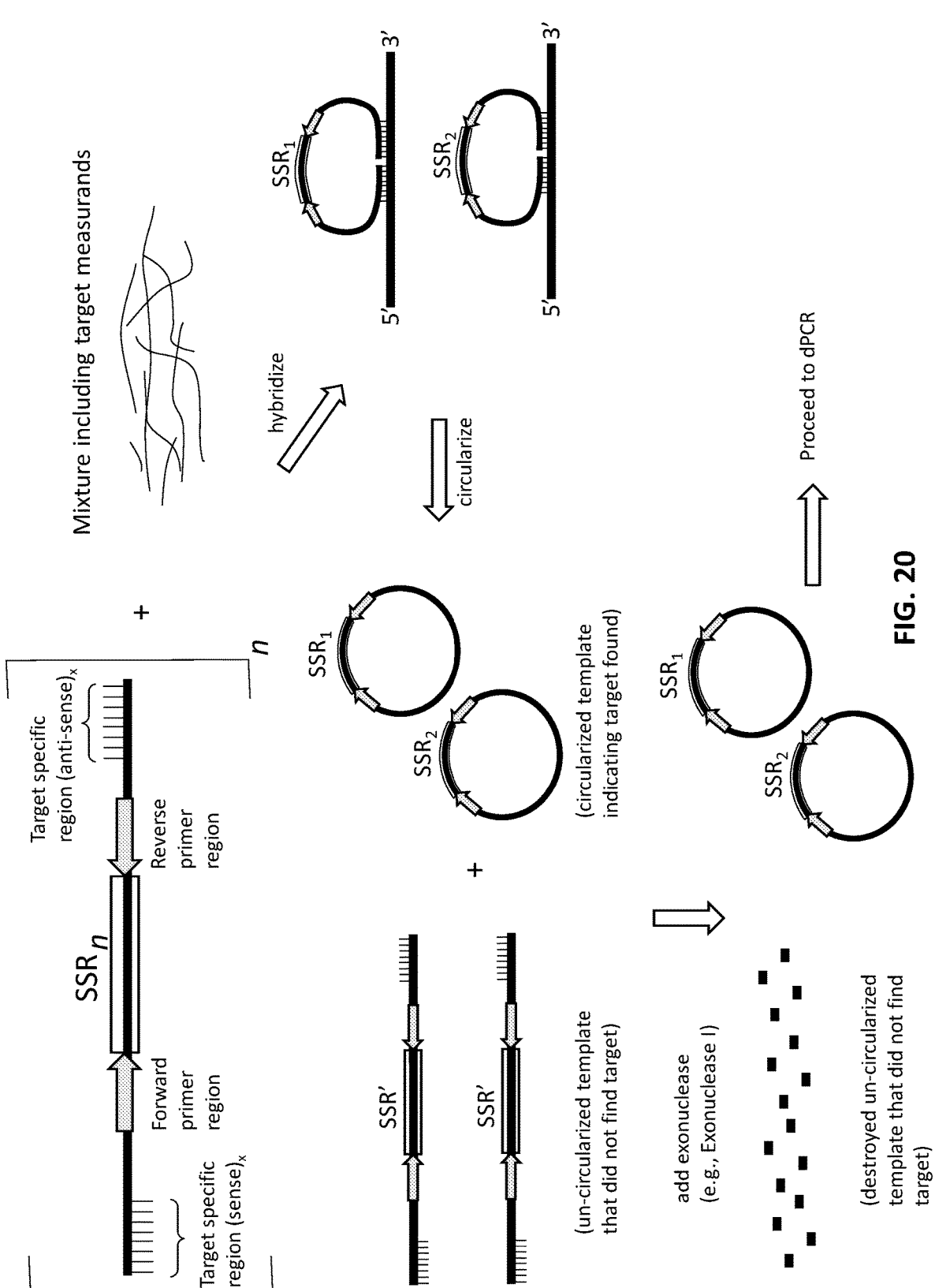
FIG. 20 illustrates one example of a sequence conversion method using a circularizing sequence conversion probe.

FIG. 20 illustrates one example of an assay (e.g., an NIPT assay) using a plurality of different cSCPs directed to different chromosomes. In FIG. 20, multiple sets (n sets) of cSCPs are added to a mixture of genetic material including multiple target measurands. Each set of cSCPs may have a common shared SSR (SSR$_n$), and multiple pairs of target-specific regions (e.g., x sets of target-specific regions, both sense and anti-sense regions). These multiple sets may be combined with the genetic material and hybridized to form circularization complexes on the target measurands. A circularizing agent (e.g., ligase) may then be added to circularize those cSCPs that have hybridized to target measurands and formed circularization complexes. The un-circularized cSCPs may then be degraded by a nuclease such an exonuclease that degrades the single-stranded cSCPs. The remaining circularized cSCPs may then be assayed to determine which markers were present, and in which proportions or amounts. For example, a digital PCR method may be used as described above, using the various SSR regions (the n SSR regions). The cSCP described in FIG. 20 ensures a fully synthetic SSR. Unlike a padlock probe the amplicon derived from this cSCP does not contain any target sequences.

The use of a sequence conversion assay in which the sequence conversion probe is configured to be an inversion probe (e.g., a padlock probe) may be particular advantageous. As described above in reference to FIG. 1D, in some variations very strict tolerances may be necessary, particularly in variations adapted for use with NIPT, as described herein. Sequence conversion assays that include a circularizing SSR may address this need, particularly where all non-circularized DNA (including hybridized polynucleotides and un-hybridized polynucleotides) may be digested and removed (e.g., by the use of a nuclease, such as a DNase, exonuclease, etc.). This approach may not necessarily rely on the affinity marker (e.g., SA-biotin) SCP cleanup, and in some variations may not include an affinity marker on the SCP. Optionally, the affinity marker may be included.

Figure 21A:
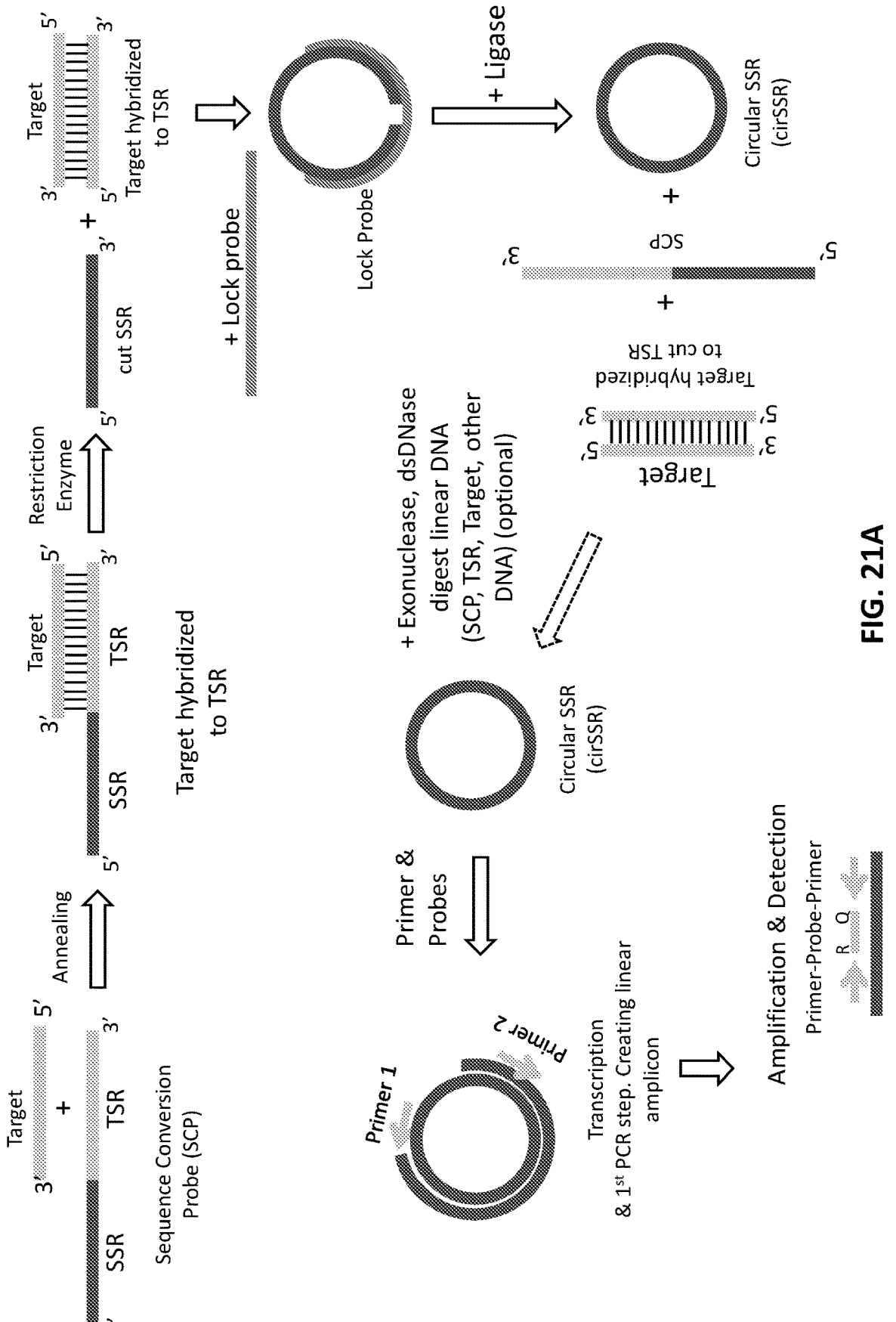
FIG. 21A illustrates an example of a sequence conversion method using a sequence conversion probe (SCP) including a signal specific region (SSR) that may be circularized by a lock probe and a ligase (forming a circularized SSR or cirSSR).
Figure 21B:
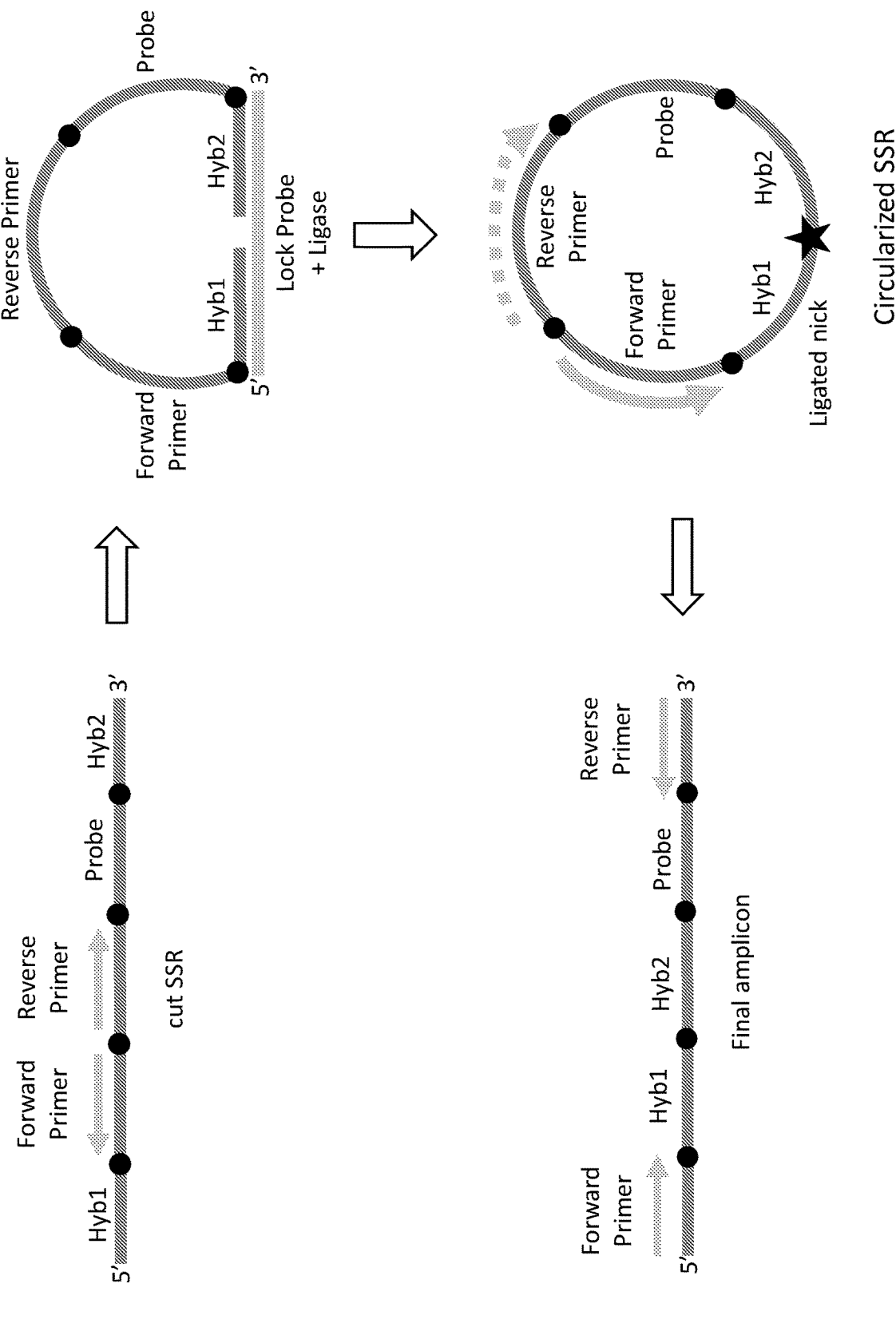
FIG. 21B illustrates in more detail the circularization and amplification steps shown in FIG. 21A.

As descried above, in some variations, the SSR may be engineered so that the SSR only becomes PCR-detectable after being separated from the SCP and circularized, e.g., by including primers oriented away from each other rather than towards each other (FIG. 21B). This may further ensure that the final signal is only generated by the released SSR (e.g., cut SSR) that has been circularized. In general, as described above, the SSR may include an engineered polynucleotide marker; different SCPs may include the same SSR, providing a reductionist assay in which multiple target-specific regions (e.g., all shaping a higher-order relationship, such as a same chromosome, same gene, same allele, etc.) may be coupled to the same SSR output. In case where the SSR only becomes PCR-detectable after being separated from the SCP and circularized the exonuclease cleanup step becomes optional because the linear (uncircularized) SSR cannot be amplified and generate a signal.

FIG. 21A illustrates one example of a method of implementing such an embodiment. In FIG. 21A, the cut SSR forms a protected single stranded DNA circle (closed circle inversion probe) from the released SSR. This circularized SSR (cirSSR) is resistant to exonuclease treatment, allowing subsequent degradation of the intact linear SCP through exonucleases, as shown in FIG. 21A. This reaction is highly specific because the SCP cannot be circularized; the SSR may be circularized when it is released from the SCP.

For example, in FIG. 21A, the SCP includes an SSR and TSR region (which may be oriented with either the TSR at the 3' end or at the 5' end, as described above. Optionally the TSR may be coupled to (or may include) an affinity marker; in some variations, no affinity marker is included. If included, the affinity marker may be used to bind to a solid phase (e.g., Streptavidin-coated magnetic beads) as described above in reference to FIG. 1B. The SCP may also include a sequence specific region (SSR) that is configured to be circularized after being released by cutting with a nuclease, as shown in FIG. 21A. In this example, when the cut SSR is hybridized to a lock probe and combined with ligase, the cut SSR circularizes to form a circularized SSR (cirSSR). To circularize the linear cSSR it may be hybridized to a specific lock probe, allowing ligase-mediated circularization after the cSSR was released by restriction enzyme activity from the SCP upon hybridization to its DNA target. The lock probe includes regions that recognized the 5' end and the 3' end of the cut SSR (with one end complementary to the end of the cut SSR in an inverted orientation and the opposite end complementary to the other end of the cut SSR in an un-inverted orientation, so that the cut SSR is hybridized in a circular manner). After ligation, one or more nuclease (e.g., exonuclease) may optionally be added to digest linear DNA, including intact SCP. The circularized SSR will not be cut by one or more enzymes that digest linear DNA and may be used to remove the uncut SCP as well as the target DNA (measurand DNA) and TSR. The circular cSSR is then amplified in the downstream PCR or dPCR without unspecific signal contribution by the undigested SCP. Only the circular SSR may be detected, e.g., using primers regions in the SSR that are oriented so that they may only be amplified when the SSR is circularized, resulting in a detectable probe, as shown in FIG. 21A. As mentioned above, an optional affinity tag (i.e. biotin) may be used for one or more additional cleanup steps in addition to the circularization and exonuclease digestion. It may be beneficial to engineer into the SSR between the primer sites a restriction site allowing linearization of the cirSSR with a restriction enzyme before start of PCR.

In general, the use of a nuclease (e.g., an endonuclease, such as a DNase) in the method shown in FIG. 21A is optional (indicated by the dashed arrow). Because the direction of the priming regions on the SSR are only correctly oriented once the SSR has been cut and circularized, the amplification and/or detection may be sufficiently specific even in the presence of the un-circularized SSR (including full or truncated SCP).

Figure 21C:
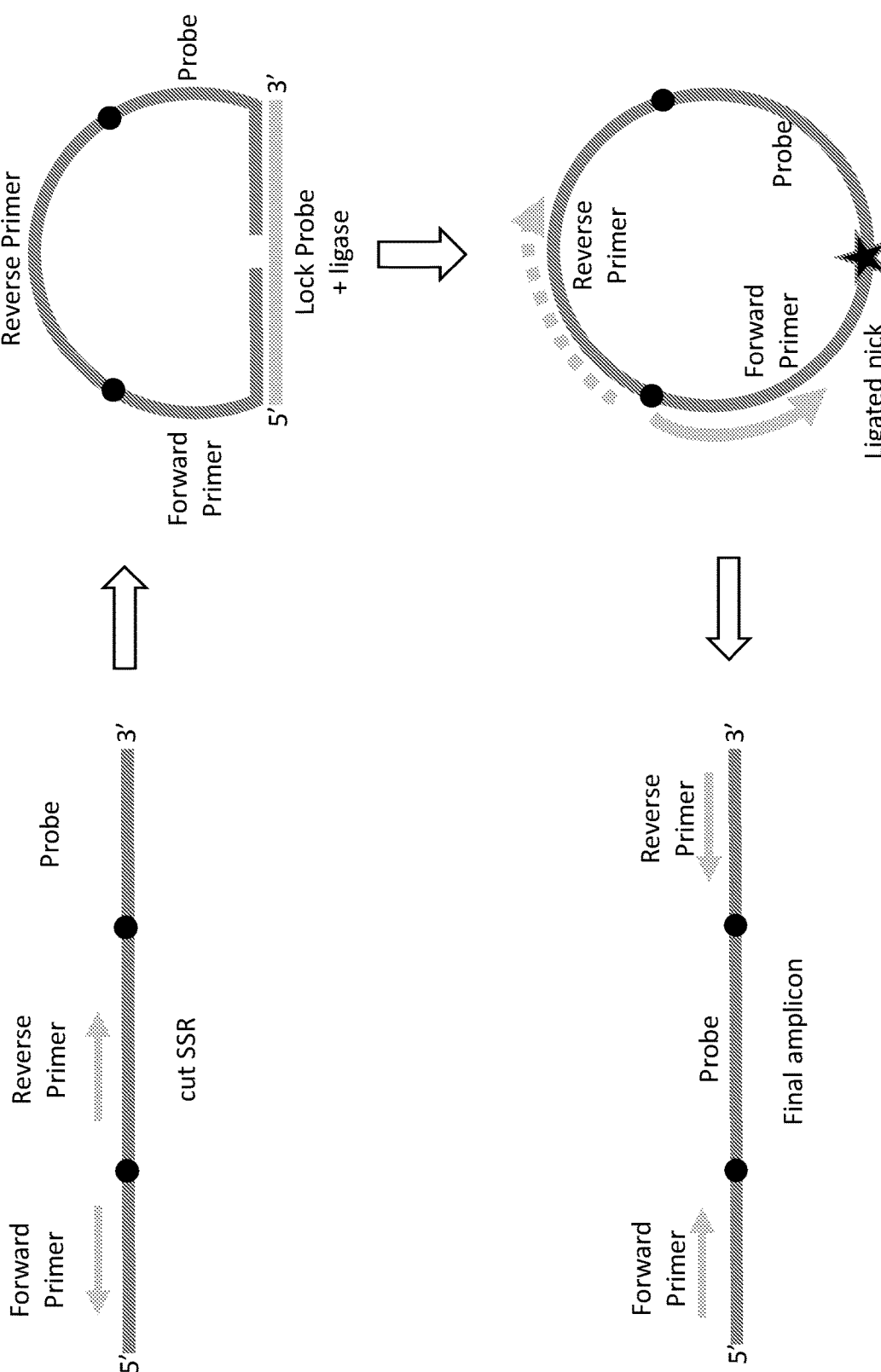
FIG. 21C shows another example, similar to FIG. 21B, in which the cut SSR is configured as a circularizable SSR that may be circularized by a lock probe in the presence of ligase.

FIG. 21B shows a more detailed example of the circularization of a cut SSR from a sequence conversion probe including an inversion probe as described herein. In FIG. 21B, the cut SSR is engineered to include a 5' hybridization end region (first hybridization region, Hyb1) and a 3' hybridization end region (second hybridization region, Hyb2) as well as a forward primer region and a second primer region and a probe region. Optionally, the first hybridization region (Hyb1) may comprise part of the forward primer binding region and the second hybridization region (Hyb2) may comprise part of the probe binding region, as shown in FIG. 21C. This optional design to use part of the forward primer and/or probe binding region in the hybridization regions results in an SSR of reduced length compared to an SSR with separate hybridization and primer binding regions. This optional design is possible due to the fully synthetic and engineered nature of the SSR. The engineered probe region may be a synthetic (e.g., engineered, non-naturally occurring region) that may be used for detection of the cut SSR, as described herein. In FIG. 21B, the cut SSR may include the forward primer region (for hybridizing to a first, forward, primer) and a reverse primer region (for hybridizing to a second, reverse, primer). In the cut SSR, the forward and reverse primers may be arranged in tandem. These regions may be oriented so that once circularized, following hybridization to a lock probe, as shown in FIG. 21B, and ligated to circularize the cut SSR, the forward and reverse primers may be oriented towards each other, allowing replication (e.g., amplification) of the region of the cut SSR including the probe. In FIG. 21B, this is shown by the final amplicon, which includes the forward primer region at the 5' end and the reverse primer region at the 3' end, with the probe between the forward and reverse primer. In some variations the probe may include or incorporate one or both of Hyb1 and Hyb2. Thus, in this example, the padlock structure of the SSR only becomes PCR detectable after being separated from the SCP and circularized. In the ligated, circularized inversion probe shown in FIG. 21B (which in some variations may be padlock probe), the star shown in the circularized SSR represents a ligated nick, which may allow a PCR primer to amplify across the ligated junction. In some variations, the probe may be configured to include a TaqMan probe binding region. As described, to further improve specificity, primer regions (for hybridizing to primers) and probe regions may be arranged on the SSR in such a manner that they only become PCR amplifiable after circularization, forming a padlock probe. The padlock arrangement may depend on cut SSR circularization and may create a specific cSSR signal even in the presence of SCP. This system may be highly specific, because the primers that hybridize to the forward and reverse primer regions in the SSR may point in the wrong direction (e.g., away from each other) when the cut SSR is in the linear form, but may point in the right direction (e.g., towards each other) in the circularized cut SSR configuration. In FIGS. 21A-21C, the inversion and/or padlock probes are configured to hybridize to sequences that are not found in the genomic target. Instead, the hybridization sequences are derived from a synthetic target.

Figure 21D:
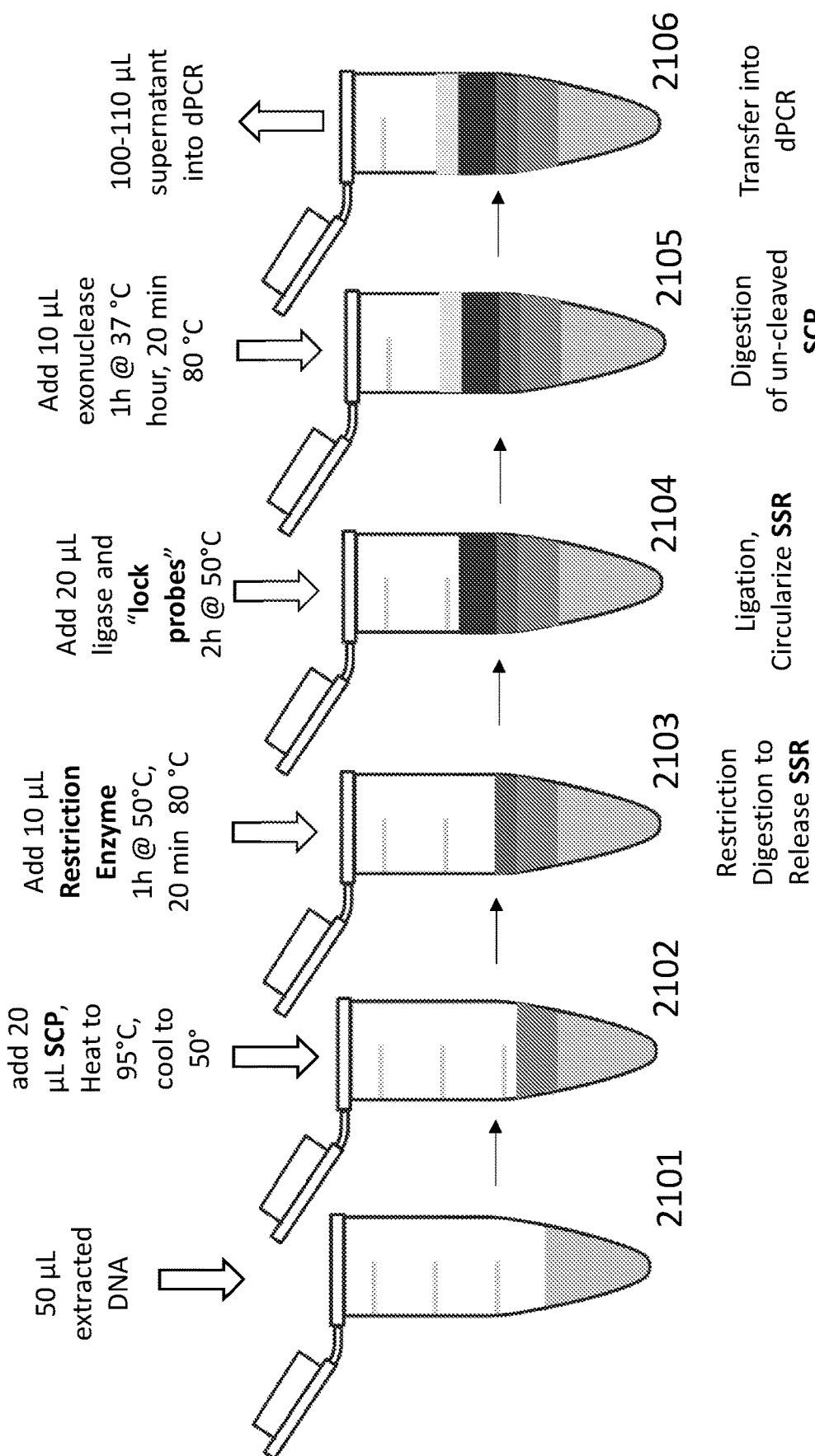
FIG. 21D illustrates one example of a workflow that may be used for the procedures described herein, including but not limited to the procedure of FIG. 21A (e.g., as part of a method for detecting chromosomal ploidy).

FIG. 21D illustrates one example of a method (e.g., workflow) as described herein. This method may be used with a circular cSSR as described. In this example, the method incorporates the general method described in FIG. 21A, in which the sequence conversion probe is configured to be an inversion probe; in particular, in this variation the SCP includes SSR that is configured to be circularized by a lock probe. The lock probe may be generic to all of the cut SSRs (e.g., the 3' and 5' end regions of the SSRs having different engineered identification (probe) regions may be the same); alternatively, different cut SSRs may have different lock probes that may be used (e.g., as part of a pool of lock probes).

In FIG. 21D, the workflow may begin by adding a mixture including the target measurand to the chamber (e.g., well or tube) 2101; the mixture may contain, for example, a mixture of material and fetal genomic material (e.g., as from a maternal blood sample). This material may be an extract of the fetal and maternal DNA (e.g., a 50 μL portion of the extracted DNA in FIG. 21D). The SCP material may be added to the mixture including the measurand 2102. The SCP material may be, for example, a portion of a mixture of SCPs that include a plurality of different target-specific regions (TSRs), where the different TSRs are divided into two or more subsets sharing a same SSR, as described above. For example, in FIG. 21D, 20 μL of the SCP mixture may be added to the mixture and heated to melt the DNA (e.g., heated to approximately 95° C.), then cooled (e.g., to approximately 50° C.) to allow hybridization of the TSRs to the measurand in the mixture 2102. Following hybridization, a nuclease (e.g., a restriction enzyme) may be added to the mixture 2103, to cut any SCP that has hybridized to a measurand. For example, 10 μL of restriction enzyme may be added and incubated at 1 hour (e.g., at 50° C.) followed by heat-inactivation of the restriction enzyme (20 minutes at 80° C.); this may release the SSR by cutting the SCP. The lock probe(s) and ligase may then be added (together or sequentially) to circularize the SSR 2104. For example, in FIG. 21D, 20 μL of the ligase and lock probe(s) may be added and incubated for 2 hours at 50° C. Following circularization, in some variations the linear DNA in the mixture may be digested 2105, e.g., by (optionally) adding a nuclease (e.g., 10 μL, of exonuclease) and incubating (e.g., 1 hour at 37° C., followed by heat inactivation at, e.g., 80° C. for 20 minutes). A sample of the resulting mixture may then be taken 2106 for detection and/or amplification (e.g., a 5-10 μL, sample of the 100 to 110 μL, supernatant may be used in one or more dPCR procedure as described herein). Note that as the material is added to the well or tube as shown in FIG. 21D, the mixture may optionally be mixed (agitated, vortexed, etc.).

This workflow, which in this example does not depend on a biotin streptavidin clean-up, may be highly specific for cut SSR amplification and may prevent all or most of the background that may otherwise arise from un-cut SCP, when using an exonuclease digestion destroying the un-cut SCP.

Another example of a workflow for use with a sequence conversion method as described herein, similar to that of FIG. 21D, is shown in FIG. 21. As in FIG. 21D, in FIG. 21E the amounts (shown in μL) are exemplary only; other volumes may be used. Similarly, the temperatures and times are examples only and may be modified. In FIG. 21E the sequence conversion probe is configured to be cut to release a cut SSR (e.g., a cSSR and/or a short cSSR). The resulting cSSR may be kept linear, or it may be circularized. In some examples an additional primer, such as an SSR extension probe may be ligated to an end (e.g., the 3' end) using a lock probe.

Figure 21E:
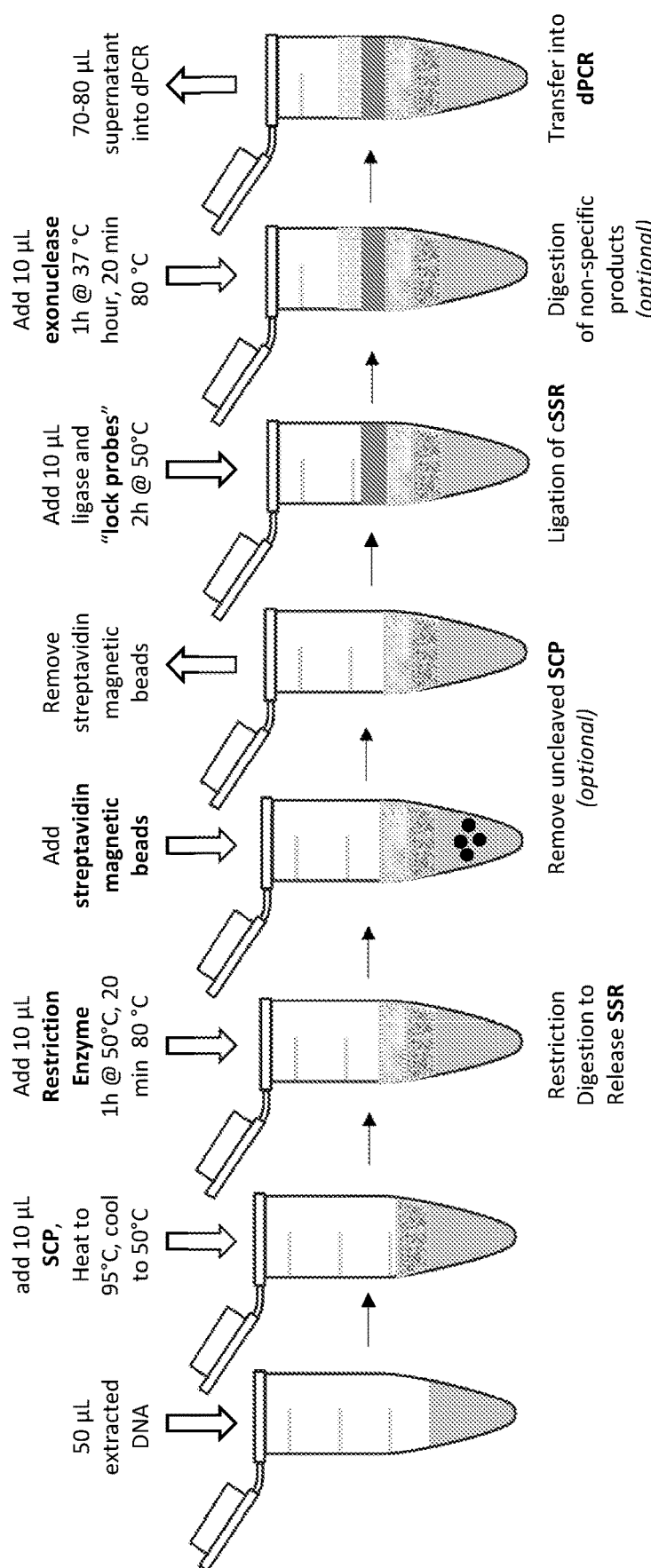
FIG. 21E illustrates an example of a workflow that may be used for some of the methods described herein.

In FIG. 21E, the workflow may begin by adding a mixture to be tested to identify the presence and/or amount of a target measurand to a chamber (e.g., well or tube); the mixture may contain, for example, a mixture of material and fetal genomic material (e.g., as from a maternal blood sample). This material may be an extract of the fetal and maternal DNA (e.g., a 50 μL, portion of the extracted DNA in FIG. 21E). The SCP material may be added to the mixture potentially including the measurand. The SCP material may be, for example, a portion of a mixture of SCPs that include a plurality of different target-specific regions (TSRs), where the different TSRs are divided into two or more subsets sharing a same SSR, as described above. For example, in FIG. 21E, 10 μL, of an SCP mixture may be added to the sample mixture and heated to melt the DNA (e.g., heated to approximately 95° C.), then cooled (e.g., to approximately 50° C.) to allow hybridization of the TSRs to any measurand in the mixture. Following hybridization, a nuclease (e.g., a restriction enzyme such as a type IIs restriction enzyme) may be added to the mixture, to cut SCP that has hybridized to a measurand, releasing a cut SSR (cSSR). For example, 10 μL, of restriction enzyme may be added and incubated at 1 hour (e.g., at 50° C.) followed by heat-inactivation of the restriction enzyme (20 minutes at 80° C.). Optionally, the mixture with cSSRs (e.g., short cSSRs) may be cleaned by adding streptavidin magnetic beads, removing uncleaved SCP and cut TSR by separating the streptavidin magnetic beads from the mixture including the cSSRs.

In some examples, as described in greater detail below, lock probe(s), SSR extension probe, and ligase may then be added (together or sequentially) to ligate the SSR extension probe to an end of the short cSSR. In some examples this may result in circular cSSR (cirSSR); alternatively the cSSR ("long cSSR" comprising the short cSSR and SSR extension probe) may be left linear. For example, in FIG. 21E, 10 μL of ligase and lock probe(s) may be added and incubated for 2 hours at 50° C. In some examples (e.g., when circularized) linear DNA in the mixture may be digested, e.g., by (optionally) adding a nuclease (e.g., 10 μL of exonuclease) and incubating (e.g., 1 hour at 37° C., followed by heat inactivation at, e.g., 80° C. for 20 minutes). A sample of the resulting mixture may then be taken for detection and/or amplification (e.g., a 70-80 μL supernatant sample may be used in one or more dPCR procedure as described herein). Note that as the material is added to the well or tube as shown in FIG. 21E, the mixture may optionally be mixed (agitated, vortexed, etc.). This workflow may be highly specific for cut SSR amplification and may prevent all or most of the background that may otherwise arise from un-cut SCP.

Figure 22A:
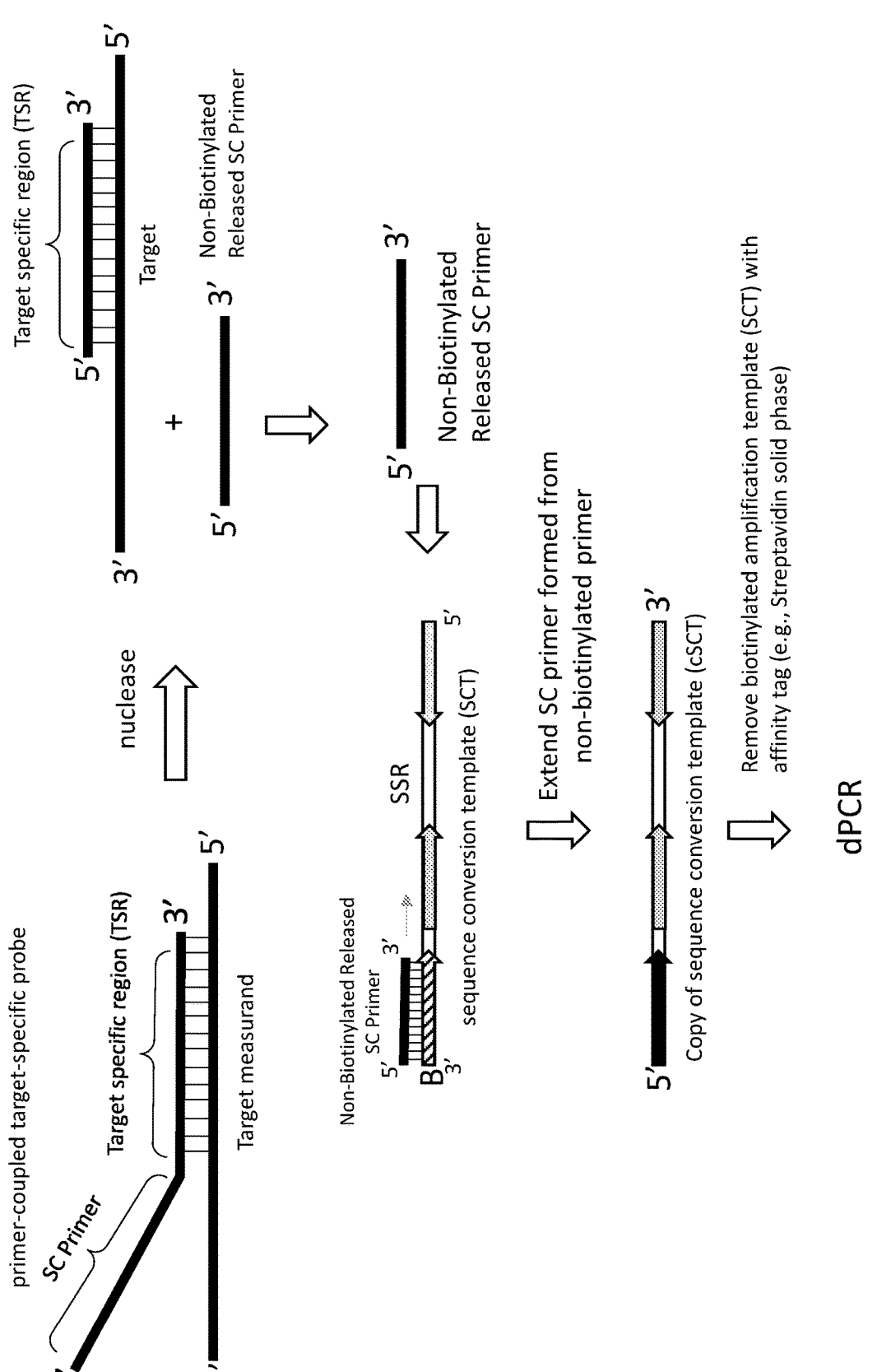
FIGS. 22A-22B illustrate examples of a variation of a sequence conversion method configured as a primer-driven assay. In this example, a first primer-coupled target-specific probe is configured to hybridize to a target measurand and be cut, e.g., by a nuclease, to release a sequence conversion primer (SC primer) that is then used to selectively extend a sequence conversion template (SCT). Extended SCT (the "copy of the SCT" or cSCT) may then be separated from un-extended SCT, and the extended SCT, or a signal specific region (SSR) on the copy, may be detected.
Figure 22B:
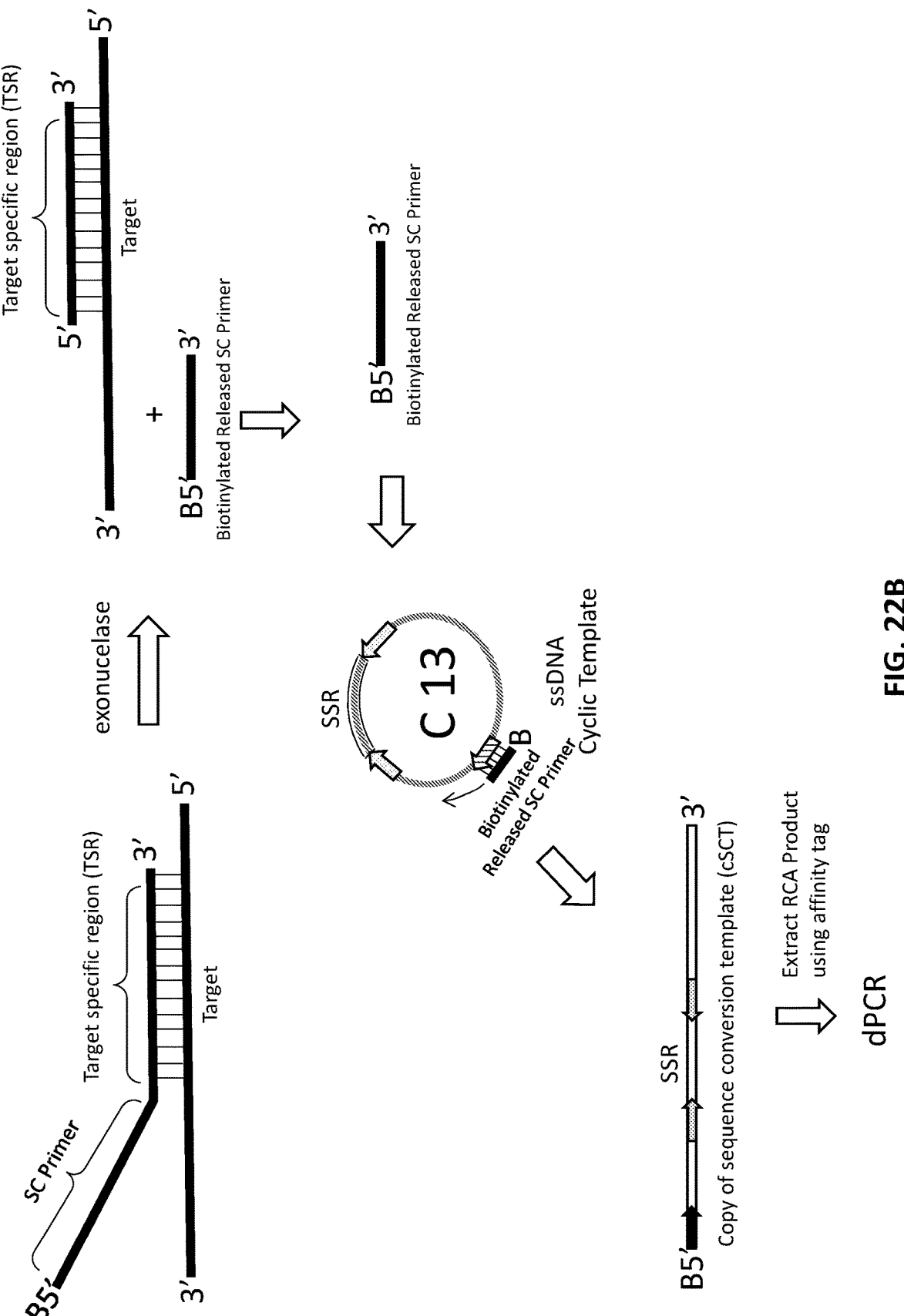

Another variation of a sequence conversion method is shown in FIGS. 22A and 22B and includes a primer driven sequence conversion method. In the primer-driven variation of the sequence conversion method described herein the primer-coupled target-specific probe (PCTSP) may be used to initially hybridize with the target and release a primer (a sequence conversion primer or SC Primer) when a target measurand is present. The PCTSP once hybridized to a target measurand is cleaved by a nuclease (e.g., exonuclease) to release the SC Primer. The SC primer may then prime extension of a sequence conversion template (SCT) that includes a signal specific region (SSR), forming a copy of the sequence conversion template (cSCT). The SCT includes an affinity tag (shown as biotin in FIG. 22A), or in some variations may be bound to a solid phase substrate either though an affinity tag or otherwise. The SCT may be isolated from copied SCT and the copied SCT may then be detected, either by an amplification detection or by direct detection. For example in some variations the copies of the sequence conversion template (cSCTs) may be analyzed via digital PCR (e.g., directed to the SSR region as described above).

FIG. 22B is another variation of the method described in FIG. 22A, in which the same primer-coupled target-specific probes may be used to generate an SC Primer as described above, however the primer may hybridize to a complementary SC region of a circular (rather than linear, as shown in FIG. 22A) sequence conversion template (SCT). As shown in FIG. 22B, the SC primer may hybridize to the circular, single-stranded SCT to create a copy of the sequence conversion template (cSCT), which (depending on the assay conditions) may have multiple copies of the SSR as the single primer drives replication. This may provide some amplification of the detection.

In the variation shown in FIG. 22B the SC primer region of the primer-coupled target-specific probe (PCTSP) includes an affinity tag. Thus, the copies of the cyclic template (the copies of the circular sequence conversion template) each incorporate the affinity marker at the end incorporating the SC Primer (in FIG. 22B, the 5' end). The affinity-tagged cSCT may then be separated from the circular sequence conversion templates and assayed, e.g., in a digital PCR assay.

In general, the methods and compositions described herein may allow for the conversion of one oligonucleotide sequence into another one, including converting several oligonucleotide sequences into one sequence. Examples of this may include converting RNA into DNA, converting long sequences into short sequences, short sequences into long sequences, converting a first sequence into another sequence, increasing the apparent copy number of an analyte, and the like.

In general the engineered SSR sequence may be designated such that it has desirable properties that the target measurand sequence does not have. Thus, these methods and compositions may simplify (e.g., convert, translate) many sequences into few, e.g., consolidating them into a single sequence. As described herein, this may change the length of a target sequence to a length making it detectable or easier to detect. For example, PCR amplicons typically need to have a certain length to accommodate forward and backward primer and, in the case of TaqMan PCR, an additional probe binding region is needed. Existing technologies for detecting polynucleotides are often limited by the size of the polynucleotide, typically requiring a target region length of about 100 bases or longer, preventing shorter DNA or RNA targets (e.g., of e.g. 25 bases or smaller) from being easily detected. The methods and compositions described herein may enable detection of such targets.

An SCP may be synthesized in any appropriate manner. SCP probes can be made for example by coupling several different multi-mers that have been pre-manufactured. For example, it might be advantageous to add the SSR as a single building block, or several building blocks, since it would be constant, and the chemical linkage does not have to be a nucleotide or DNA. It might include any other chemical linker. From a structural perspective the SCP does not need to be 100% oligonucleotide.

Figure 29A:
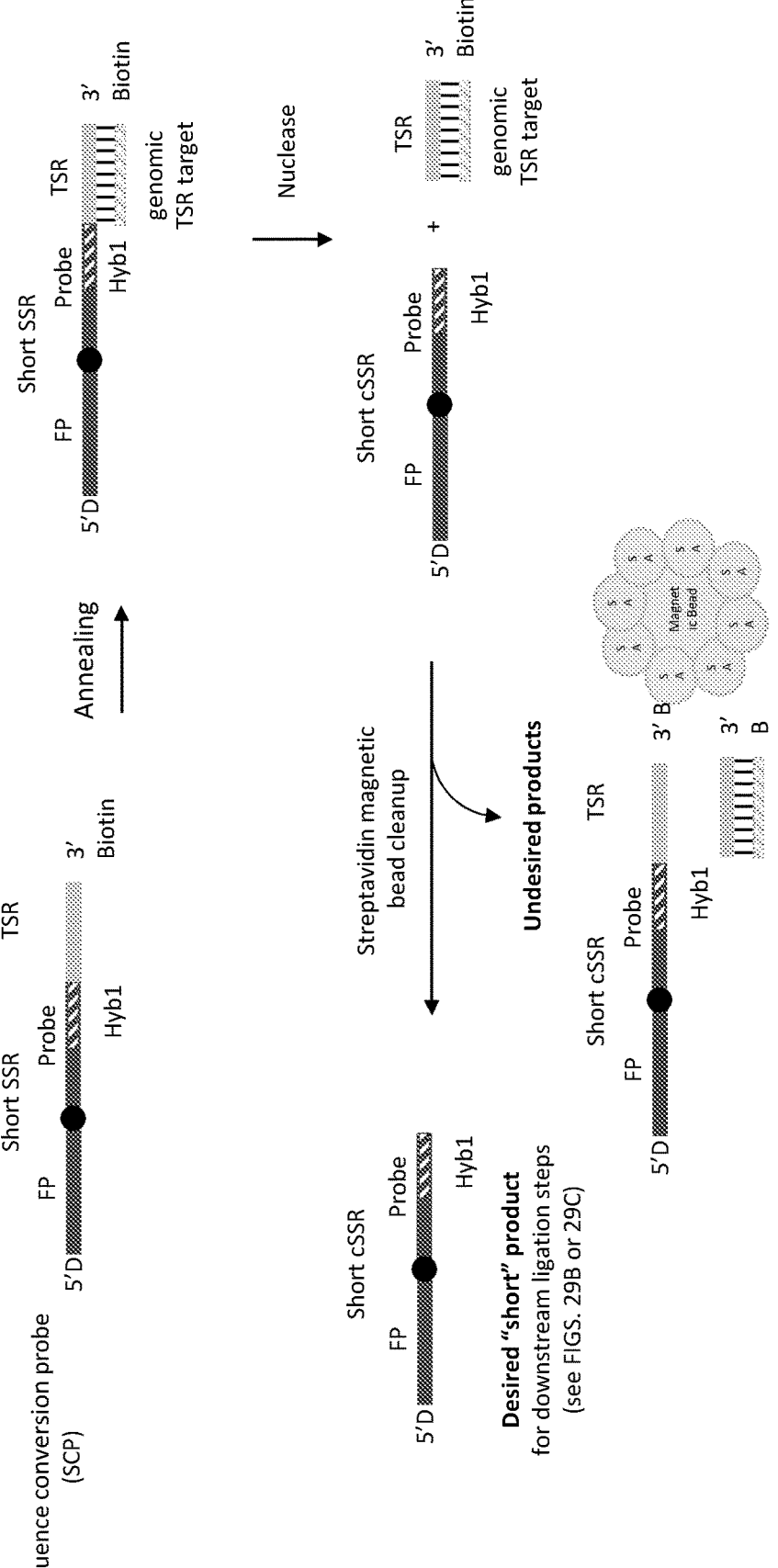
FIG. 29A illustrates an example of a first portion of a sequence conversion method as described herein.

Another variation of a sequence conversion method is shown FIGS. 29A-29D. In this example, the method includes a sequence conversion probe (SCP) that is a polynucleotide including a target-specific region (TSR) and a signal specific region (SSR). The SSR may be a circularizable SSR. The SSR includes a first engineered polynucleotide marker including one or more primer regions (shown in this example as a forward primer, FB, but it may be a reverse primer, RP). The 5' end of the SSR may include a ligation blocker, such as 5' H, 5' biotin, 5' inverted bases, 5' digoxin. 5' D-bases. 3' PO4, 3' biotin, 3' inverted bases, 3' D-bases. In FIG. 29A the ligation blocker on the 5' end of the SCP is shown as 5'D. The 3' end of the SCP includes one (or more) biotin.

In any of the methods described herein a plurality of SCPs may be used together. The plurality of SCPs may include a plurality of different TSRs configured to hybridize to different target measurands, while each of the SCP in this (first) plurality may include the same SSR, as described above. In FIG. 29A, the SSR is referred to as a "short SSR" because it may later be annealed to an SSR extension probe, as described below. The SSR may include an abasic or other region to prevent transcription (shown by black circled functional region). One or both ends of the SSR (short SSR) may be configured to hybridize to a linker or lock probe, as shown in FIGS. 29B and 29C, respectively.

In FIG. 29A, the SCP is added to a sample mixture to be tested for the presence of one (or in some examples, more) target measurand. As described herein, the target measurand may be a genomic (e.g., chromosomal) target, and the mixture may include a sample to be tested. If a target measurand corresponding to the TSR is present in the sample, the SCP may be hybridized (via annealing) so that the TSR region hybridizes to the target measurand, shown in this example and a genomic target measurand; any appropriate measurand may be used, as described above. A nuclease (such as, but not limited to, a type IIs restriction enzyme) may be used to cut the SCP, releasing the cut SSR (cSSR). Optionally, the sample may be cleaned using streptavidin (e.g., magnetic streptavidin beads) to remove the uncut SCP and the cut TSR, as shown. The resulting cSSR (or "short cSSR") may then be processed as shown in FIG. 29B (linear product) or FIG. 29C (circular product).

Optionally, in some examples an SSR extension probe may be added to the end (e.g., the 3' end) of the short cSSR. In FIG. 29B the SSR extension probe is added, along with a lock probe (which may also be referred to as a linker probe) to ligate the SSR extension probe to the 3' end of the short cSSR, in order to form the final amplicon, that may be detected. The SSR extension probe may include a second primer region (e.g., including a reverser primer, RP, or a forward primer, FP), shown including a reverse primer in FIG. 29B. The 3' end of the SSR extension probe in FIG. 29B includes a ligation blocker (shown here as 3'P*) to prevent improper/undesirable ligation. In this example, the lock probe hybridizes to both the short cSSR and the SSR extension probe. The resulting final amplicon may then be amplified using primers directed to the first and second primer regions, as shown. FIG. 29B shows a linear final amplicon. Alternatively in some examples the final amplicon may be circular, as shown in FIG. 29C.

Figure 29C:
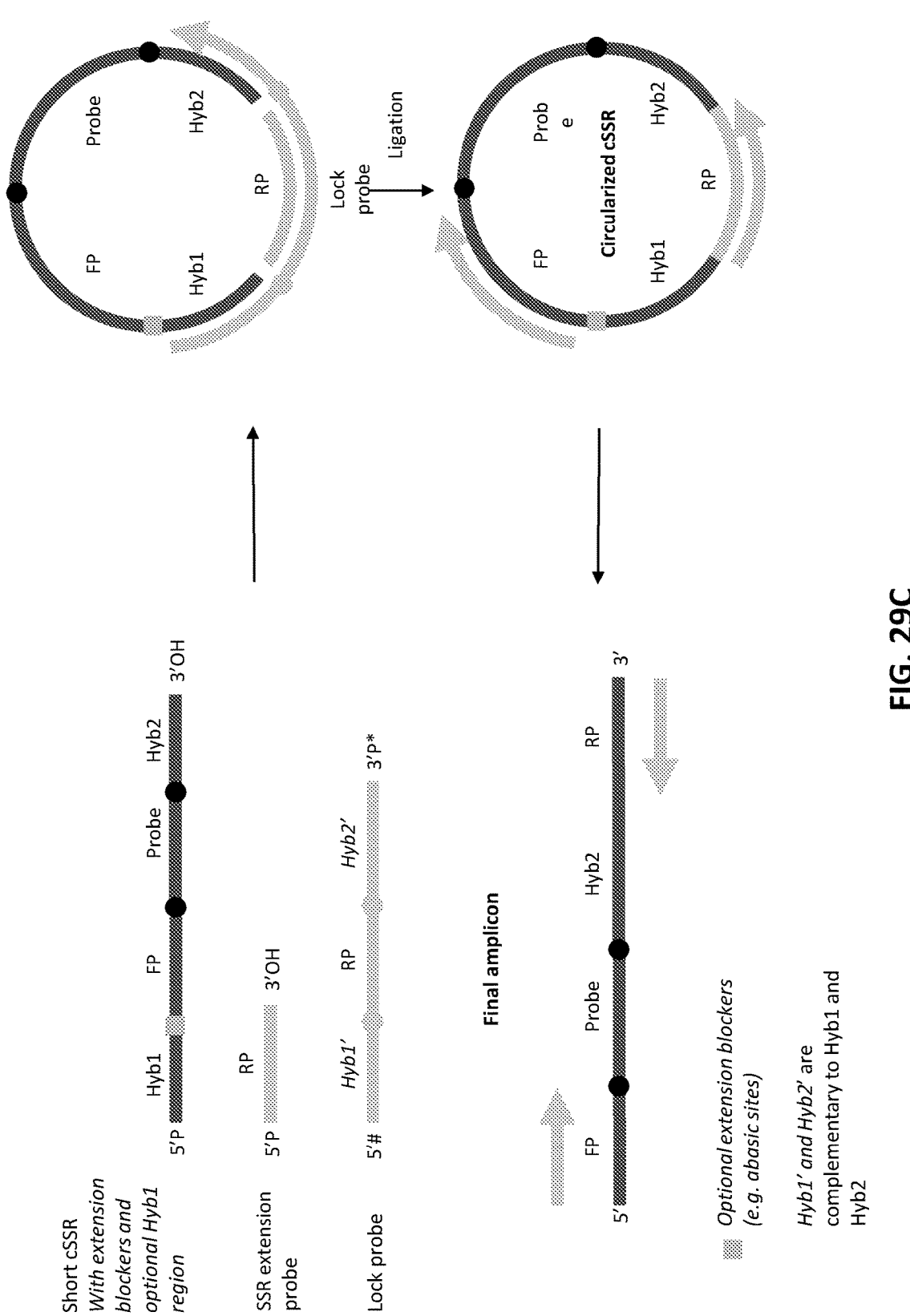
FIG. 29C schematically illustrates another example of conversion of the cSSR from FIG. 29A into a sequence (which does not include any genomic, e.g., target measurand, sequence) that may be detected using nucleic acid amplification and/or by hybridization.

In FIG. 29C, as in FIG. 29B, an SSR extension probe may be added to the end of the cut ("short") SSR (short cSSR). In this example, the cSSR includes a first primer region (including a FP or a RP), and a probe region. A transcription interruption region (shown as a rectangle) may be present between the first primer region and the 5' end of the SSR, such as an abasic region. The 5' end of this example SSR also includes a ligation blocker. As in FIG. 29B an SSR extension probe is also included. The lock probe in any of these examples may also a ligation blocker on one or both ends (as shown in FIGS. 29B and 29C). The short cSSR may be circularized with the lock probe so that the SSR extension probe is ligated into the resulting circularized cSSR (cirSSR). The cirSSR may then be detected as described above, forming a final amplicon between the first (e.g. forward) and second (e.g., reverse) primer regions, as shown.

The use of an SSR extension probe is optional, and may be used to dramatically reduce background, which may be particularly helpful in some examples. In general, the SSR extension probe may include an appropriate number of nucleotides (e.g., between 6 and 40 or more), and the sequence may be specific to the second primer region.

The workflow shown in FIG. 21E may be used with the technique illustrated in FIGS. 29A-29C illustrated above. The method shown in FIG. 21E may incorporate the general method described in FIGS. 29A-29C, in which the sequence conversion probe is configured to be cut to release a short cut SSR (short cSSR) that may be annealed to an SSR extension probe using a lock probe. The resulting SSR may be kept linear, or it may be circularized by the lock probe. The lock probe may be generic to all of the cut SSRs (e.g., the 3' and 5' end regions of the SSRs having different engineered identification (probe) regions may be the same); alternatively, different cut SSRs may have different lock probes that may be used (e.g., as part of a pool of lock probes).

EXAMPLES

The sequence conversion methods described herein (e.g., using the SCP probes described) may be used for and/or as part of a variety of different techniques. For example, these methods may be used with dPCR for applications including (but not limited to): detection of aneuploidy by digital chromosome counting using cffDNA, somatic mutation panels for oncology, syndromic pathogen panels, etc.

For example, the somatic mutation panels for oncology may be beneficial to detect a number of known cancer driver somatic mutations in oncogenes, such as EGFR, KRAS, BRAF to help guide therapy selection or screen for cancer. Such mutations are known in the literature and can be found in various databases (e.g. COSMIC). One would hybridize SCPs to mutation sites of interest from gene A (e.g. EGFR) with multiple SCP probes each with unique TSRs but all with a common SSR (e.g. with a probe binding site for a FAM-labeled probe). The TSRs would be perfectly matched to the mutations of interest (e.g. EGFR L858R, T790M, etc.) but would be mismatched to the wild type gene. As a result, only the SCPs bound to the perfectly matched mutant sites would be cleaved by the nuclease. The multiple SCPs for a second gene (gene B, e.g. KRAS) would similarly have unique TSRs for the mutations of interest in gene B but would have a common SSR (e.g. with a probe binding site for a HEX-labeled probe). One would amplify and detect the resulting SSRs in dPCR with as few as one primer pair and a probe specifically labeled for each gene.

Any of the methods and kits described herein may be used for minimal residual disease monitoring. Minimal residual disease (MRD) refers to the small number of cancer cells or cell-free circulating DNA derived from such cancer cells that remain in the body after treatment. The number of remaining cells may be so small that they do not cause any physical signs or symptoms and often cannot even be detected through traditional methods, such as viewing cells under a microscope and/or by tracking abnormal serum proteins in the blood. A MRD positive test result means that residual (remaining) disease was detected. A negative result means that residual disease was not detected. The methods and kit described herein may therefore be used to detect markers of cancer cells or cell-free circulating DNA from minimal residual disease. After treating cancer, any remaining cancer cells in the body can become active and start to multiply, causing a relapse of the disease. Detecting MRD may indicate that the treatment was not completely effective or that the treatment was incomplete. Minimal residual disease may be present after treatment because not all of the cancer cells responded to the therapy, or because the cancer cells became resistant to the medications used.

Any of the methods and system (e.g., kits) described herein may be used for detecting transplant rejection. For example, the methods described herein may detect donor-derived cell-free DNA and may therefore tracks DNA markers from the organ donor that appear in the blood (or other tissues or fluids) of the transplant recipient. For example, injured or dying cells from the donor organ release donor DNA fragments into the bloodstream, and higher amounts of donor DNA indicate a higher risk for transplant rejection in the recipient. The methods and systems (e.g., kits) described herein can be used to detect relative amounts of donor and patient DNA, similar to the methods for detecting fetal and maternal DNA descried herein. Current tests used to detect heart transplant rejection rely on frequent and painful biopsies of heart tissue. Those biopsies run the risk of damaging the heart and are limited by their invasiveness (ability to obtain tissue samples) and reliability for detecting acute rejection. Acute, or rapid, rejection tends to happen in the first three to six months after transplantation as opposed to chronic rejection, which occurs after many years. For example, blood samples may be monitored the patients for signs of acute rejection using the assays described herein.

These methods and compositions may be configured as syndromic pathogen panels. Such panels may be beneficial to detect groups of pathogenic bacteria, yeast and/or fungi with SCP probes in conjunction with detection (e.g., by dPCR). For example, multiple enteric pathogens causing gastrointestinal distress could be detected with SCPs including one or more target sequences (e.g. 16S RNA) in one or more bacteria (e.g. *Campylobacter, C. difficile*, etc.) that could lead to the same symptoms (e.g. acute diarrhea) and that are treated in the same manner (e.g. same classes of antibiotics). The SCPs would have multiple unique TSRs but share a common SSR for common treatment modality (Fam for the antibiotic class A; Hex for antibiotic class B).

Example 1

In one example, the methods described herein may be used to identify the ploidy of a genetic sample.

Figure 11:
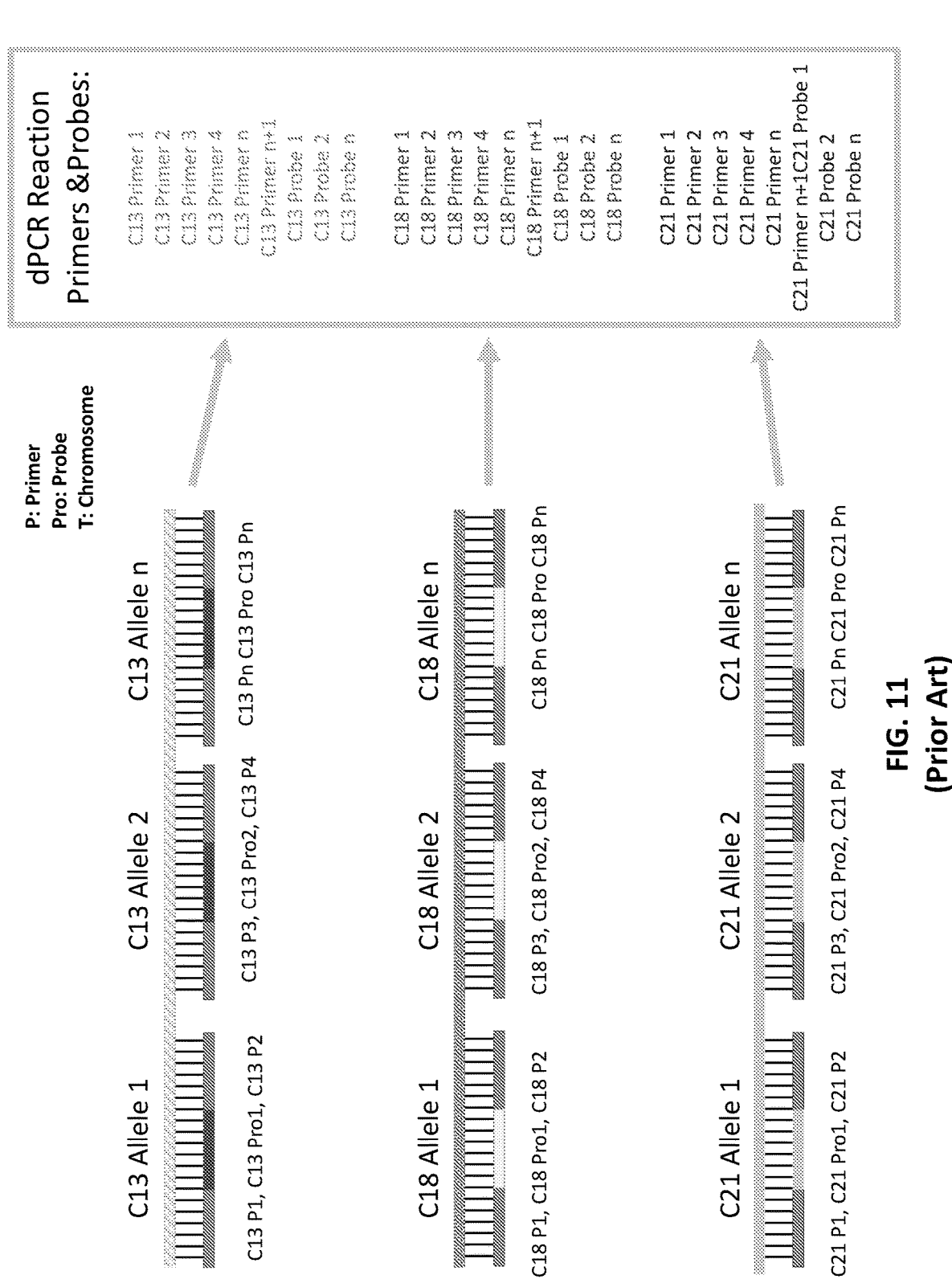
FIG. 11 schematically illustrates the use of conventional digital PCR (dPCR) to quantify chromosomes, which requires a large number of primer pairs and probes.
Figure 12:
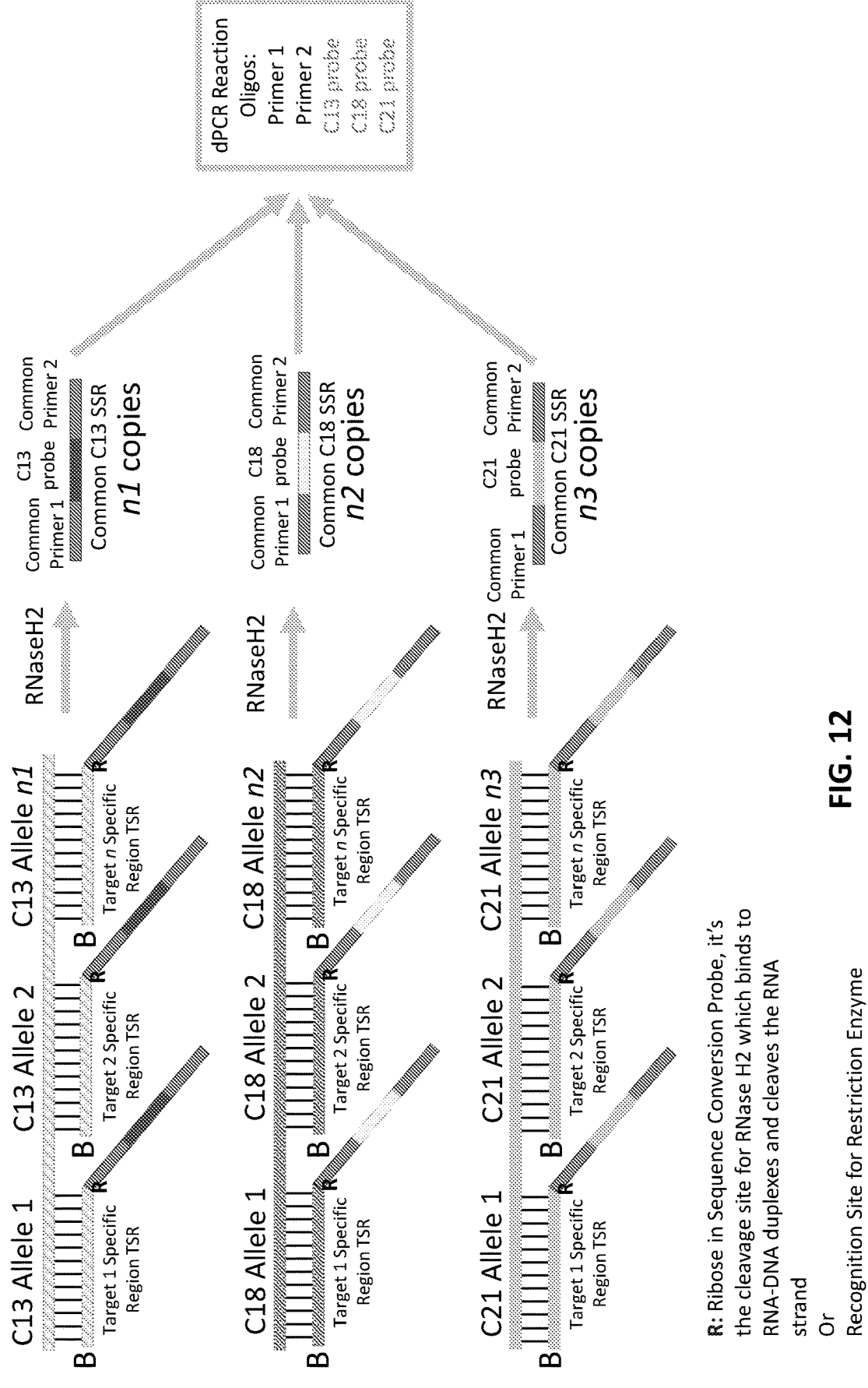
FIG. 12 illustrates one example of a sequence conversion method configured for use with digital PCR to detect chromosomes. In contrast to the method illustrated schematically in FIG. 11, the sequence conversion method requires only a small number of primers (e.g., one pair) and three probes specific to each of the three SSRs indicating each of the three chromosomes (e.g., C13, C18, and C21).

Traditional methods for using dPCR to detect aneuploidy require a large number of primers and probes to achieve statistical significance. For example, FIG. 11 schematically illustrates the principle of operation of a conventional dPCR NIPT assay. Note that typically maternal/fetal chromosomal cfDNA is fractured, though for convenience in FIGS. 11 and 12 it is indicated as a solid line to show original connectivity on the chromosome. In this simplified example, if n alleles are examined on each of three chromosomes (e.g., C13, C18 and C21), 2n primers are needed for each chromosome (two per allele) and at least n probes are needed per allele on the chromosome. Thus, for example, if 200 target measurands are used on each chromosome, 1800 oligonucleotides are required. As described above, in contrast, the methods described herein may instead use a much lower number of oligonucleotides. In some variations if 200 target measurands are used on each chromosome, only five oligonucleotides (one probe each per chromosome and a single pair of primers), even if the number of target measurands increases the number of oligonucleotides in the dPCR assay described inhere does not change. This is illustrated in FIG. 12. The use of the sequence conversion methods described herein to provide cut SSR (cSSRs) dramatically reduces the need for individual primers and probes. Furthermore because the engineered SSRs can be designed to have comparable binding and amplification properties (e.g., using the same or similar primers, etc.), the resulting signal may be much better signal to noise ratio than traditional dPCR methods.

For example, these methods may be used to identify target measurands (e.g., 100 to 200 target measurands) on each of chromosomes 21, 18 and 13 each. This information (e.g., the number of identified target measurands from each chromosome) may be used to determine the ploidy of each of these chromosomes. In some variations the method may include determining the length of each TSR with a ribose to hybridize at 70° C. plus minus 10° C. that will not dissociate after cleavage. Ribose may be placed as close to the 3' end as is possible to minimize cycling/amplification. The method may also optionally include determining for the SSR amplification part as an ideal amplicon. The primers for the C21/C18/C13 may all be identical, and probes to each of C21, C18 and C13 may be standard TaqMan probes specific for C21, C18 and C13. Each Signal Conversion probe (SCP) may have an affinity tag at one end, such as, but not limited to biotin at the 5' end. Assuming 200 target measurands each for C21/13/18 and a 100,000 well or droplet array, the method may include getting 200 different SCPs for C21, 200 different SCPs for C18, and getting 200 different SCPs for C13. Probes may be mixed at 1:1:1 ratio. There should be now roughly 600 SCPs in equimolar ratio. The total amount may be determined experimentally but can be expected to be at least 10-fold higher than the target DNA concentration. A typical concentration of an individual probe could be in the range of 5 pM-500 pM. Incubation time, temperature, and buffer condition may impact the optimal conditions. The nuclease (e.g., RNase H2) can be added before, together or after addition of SCP, however for some nucleases (e.g. restriction enzymes) it is often preferred to be added last. For example, restriction enzymes need to be added after SCP hybridization otherwise they could destroy the target DNA allele before the SCP can bind. Once the reaction has been completed, uncleaved SCP and cTSR will be removed with streptavidin bound to a solid phase (e.g. beads, column, magnetic beads, etc.). The supernatant or an aliquot may be mixed with the PCR master mix for the digital PCR reaction and run following standard protocols known in the art.

The number of positive T 21, T 18 and T 13 counts may then be compared and based on mathematical transformations (e.g. difference, ratio or other) to determine if the result is normal or abnormal.

Example 2: Sequence Conversion Method for NIPT (Detection of Trisomy 13, 18 and 21) Using Restriction Enzyme As mentioned above, in some variations a restriction endonuclease ("restriction enzyme") may be used. For example, in some variations the ploidy of a sample of genetic material including chromosomal material may be determined using the methods described herein.

In any of the methods described herein in which the nuclease used to separate the SSR from the SCP, the restriction enzyme to be used may be determined and the restriction site may be engineered into the SCP. For example, selection criterion for determining a restriction enzyme may be based on the specific needs of the methodology used, and may include the recognition site being approximately ~6 bases long (other length restriction sites work as well); the enzyme begin stable and effective at above 45° C. The enzyme chosen may be selected because it can be heat inactivated. In some variations, the recognition site may be found in the potential targets' sequences with sufficient frequency (ideally >500) on each of chromosome 13, 18 and 21, to support assay statistical requirements (e.g., the number of probes per chromosome).

In designing the SCPs, the identified restriction sites may be extended to the target-specific region (TSR) sequences. For example, the method may include identifying 200 or more sequence targets on chromosome 21, 18 and 13 each based on the chosen restriction enzyme. Possible candidate restriction enzymes may include BsmI (NEB cat #R0134L), BsmBI-v2 (NEB cat #R0739S), BspQI (NEB cat #R0712S), BsaI (NEB cat #R0535S), BsaI-HF-v2 (NEB cat #R3733S) or BssHII (NEB cat #R0199L). Alleles with the selected restriction enzyme recognition site sequence may be identified for use on chromosomes 13, 18 and 21. To determine the 5'-end for the target-specific region the Tm of the probe may be defined. Since many of these restriction enzyme work well above 45° C. (the reaction temperature), the TSR should ideally be fully bound at the reaction temperature. Therefore, a Tm of the probe above 55° C. may be used as a target. Based on this Tm in 50 mM NaCl, a TSR probe length of 10-40 bases may be ideal, depending on GC content. The TSR binding sequence may be extended (using bioinformatic techniques) for more than 6 bases downstream (direction 3'). The sequence upstream (direction 5') may be extended as needed to achieve the desired Tm. Unique sequences may be identified: sequences that are found on chromosomes other than the intended chromosome with an identity (or homology) of more than 80% may be discarded, especially those carrying the enzyme's recognition site. Sequences binding to common SNPs (e.g. >~1% frequency in the human population) in the restriction site may be filtered out. The method may also include ensuring the remaining sequences do not overlap with each other.

As used herein, when comparing polynucleotide sequences, two sequences are said to be "identical" if the sequence of nucleotides in each of the two sequences is the same when the sequences are aligned for maximum correspondence. The percentage identity between two nucleotide sequences as described herein may be determined according to art-accepted practices and criteria, for instance, the BLAST and BLAST 2.0 algorithms described in Altschul et al., *Nucl. Acids Res.* 25:3389-3402 (1977) and Altschul et al., *J. Mol. Biol.* 215:403-410 (1990).

The sequences for the Signal Specific Region (SSR) may also be determined. For example, by identifying (using bioinformatics) 3 oligo sequences not found in the human genome or human pathogens long enough to harbor a PCR amplicon. The 3 sequences may be synthetic (have very little homology or identity with the human genome), may contain two universal primer binding sites (one at the 5'-end, one at the 3'-end of the SSR) same for all three oligonucleotides, the oligo may contain a TaqMan probe binding site specific for Chromosome 13, 18 or 21 between the primer sites.

The final Sequence Conversion Probe (SCP) design may be determined by concatenating each of 200 identified Target-specific Regions (TSRs) for Chromosome 13, 18 and 21 with their respective universal Signal Specific Region (C13 SSR, C18 SSR and C21 SSR). The TSR may be at the 5' end and will be synthesized with a 5' biotin tag; the SSR is at the 3' end. This results in 200 each chromosome specific Sequence Conversion Probes. The approximately 600 HPLC purified probes may be generated, providing, for example, approximately 200 identified SCPs each for Chromosomes 13, 18 and 21.

Primers and probes may be optimized for dPCR cycling conditions with an extension temperature of 58° C. For example, the primer Tm may be 58-60° C., the probe Tm may be 68-70° C. The first probe (e.g., probe 1, C21) may include a reporter 1 (e.g., FAM) and a Quencher (e.g., Iowa Black). The second probe (probe 2, C18) may include a Reporter 2 (e.g., HEX) and a Quencher (e.g., Iowa Black). The third probe (probe 3, C13) may include a reporter 3 (e.g., Cy5), and a Quencher (e.g., Iowa Black). The primers and probe for dPCR may be optimized to be compatible with the Bio Rad ddPCR Supermix for Probes (Catalog number: 186-3010 for 500 reactions).

The method may include: (1) maternal and fetal cfDNA Extraction, (2) sequence Conversion Reaction, (3) cleanup of sequence conversion reaction, (4) partitioning (e.g. droplet generation) of cSSRs, (5) dPCR and (6) data analysis.

Sample collection and DNA extraction may include isolating plasma (e.g., within five days from blood draw). An average of 9.5 mL whole blood may be collected in cell-free DNA BCT® blood collection tubes (Streck) via a double centrifugation protocol consisting of a first centrifugation step at 1342× g for 30 minutes, transfer of the plasma fraction to a secondary tube and a second centrifugation step at 2267× g for 20 minutes. Plasma is stored at –80 C until further processing.

Extract cfDNA from 1 mL of plasma of a pregnant female as described by the manufacturer. Reagents: Maxwell® RSC ccfDNA Plasma Kit (Catalog number: AS1480); Instrument: ProMega Maxwell® RSC 48 Instrument (AS8500). Elute cfDNA in 50 μL, elution buffer. Minimize salt carry over.
Sequence Conversion Reaction 50 μl cfDNA eluate is transferred to a microtiter plate and 10 μL of SCP solution is added which contains 5-500 pM (final) locus-specific SCP probe (3-300 nM total SCP probe concentration for 600 SCP probes. Probes are at equimolar concentration). Denature at 95° C. for 60 sec, then lower temperature to 50-65° C. Add and mix 10 μL of Restriction Enzyme Buffer (containing 1-10 U BsaI-HF-v2 (New England Biolabs), 7 μL of 10× CutSmart Buffer Cat number B7204S). Incubation time and probe concentration at 50-65° C. is optimized following guidelines by Zhang et al (Nat Chem. 2018 January; 10(1): 91-98.) for 5-500 pM probe (individual SCP) at 0.5-24 hours. Temperature, concentrations and time interact with each other and allow a number of solutions to accommodate user requirements.

Cleanup of sequence conversion reaction may include, once the reaction has been completed, removal of any uncleaved SCP and cTSR by binding with streptavidin bound to a solid phase (e.g. beads, column, magnetic beads). The cSSR may be partitioned for dPCR. For example, the supernatant from the cleanup of the sequence conversion reaction may be mixed with the dPCR master mix and any additional reagents as required for the specific dPCR system (e.g. oil for droplet generation for the BioRad QX ONE Droplet Digital PCR System). The number of partitions is selected such that the required statistical significance for the intended use of the assay can be achieved. The dPCR workflow, including droplet generation, is described in "QX ONE Droplet Digital PCR System and QX ONE Software User Guide".

Digital PCR (dPCR) may be performed on the resulting SSRs. For example, a Bio-Rad QX ONE Droplet Digital PCR System (M/N 12006536) may be used with PX1 PCR Plate Sealer (1814000), and Supermix for Probes (Biorad Catalog number: 186-3010 for 500 reactions).

Table 2, below illustrates the volumes required of 10 μM stock solutions for forward primer, reverse primer, and probe to achieve final concentrations of 900 nM primer concentration and 250 nM probe concentration for one reaction:

| | |
|---|---|
| Bio-Rad ddPCR SuperMix for Probes | 11 μl |
| Forward Primer (10 μM) | 2.0 μl |
| Reverse Primer (10 μM) | 2.0 μl |

-continued

| | |
|---|---|
| Probe (10 μM) | 0.55 μl |
| Molecular Grade Water | 4.45 μl |
| Sample | 2 μl |

Note that if higher sample input is needed, reduce volume of Molecular Grade Water. The total volume accommodates for dead volume for pipetting.

Table 3 Shows an example of a thermal cycling protocol for dPCR that may be used:

| | Cycle | Time | Temperature | Ramp Rate |
|---|---|---|---|---|
| Step 1 | 1 | 10 minutes | 95° C. | 2 C./sec |
| Step 2 | 40 | 30 seconds | 94° C. | 2 C./sec |
| | | 60 seconds | 58° C. | 2 C./sec |
| Step 3 | 1 | 10 minutes | 98° C. | 2 C./sec |
| Step 4 | 1 | infinite | 12° C. | 2 C./sec |

The number of positive chromosome 21, 18 and 13 counts (e.g. empty vs occupied partitions, using Poisson distribution to determine absolute copy numbers) may be compared and based on mathematical transformations (e.g. difference, ratio or other) to ascertain if the risk for aneuploidy of chromosome 21, 18 or 13 of a particular sample is increased. Further risk factors like maternal age, being carriers of the genetic translocation, having had one child with an aneuploidy etc. can be used in combination with the assay result to generate a risk score.
Design and Selection of SCPs Described herein are methods for designing and selecting the sequence conversion probes (SCPs) that may be used with any of the Sequence Conversion Reactions described and illustrated herein (including but not limited to the assay illustrated in FIG. 21A). In general, the Sequence Conversion Reactions described herein use a Sequence Conversion Probe (SCP), which is includes a Target Specific Region (TSR), which hybridizes to a specific target sequence and a Signal Specific Region (SSR), which is a synthetic sequence not found in the pool of target sequences (e.g., is not in the genome being examined). The SCP typically includes a chemically labile site or recognition site for a nuclease between the TSR and SSR, that is configured so that the SSR may be cleaved from the TSR only when the TSR is bound to the specific target sequence. As mentioned above, an optional affinity tag such as biotin may be present at either the 5' or 3' end, preferably at the 3' end which may include more than one affinity tag molecule.

Figures 26A, 26B, 26C, 26D:
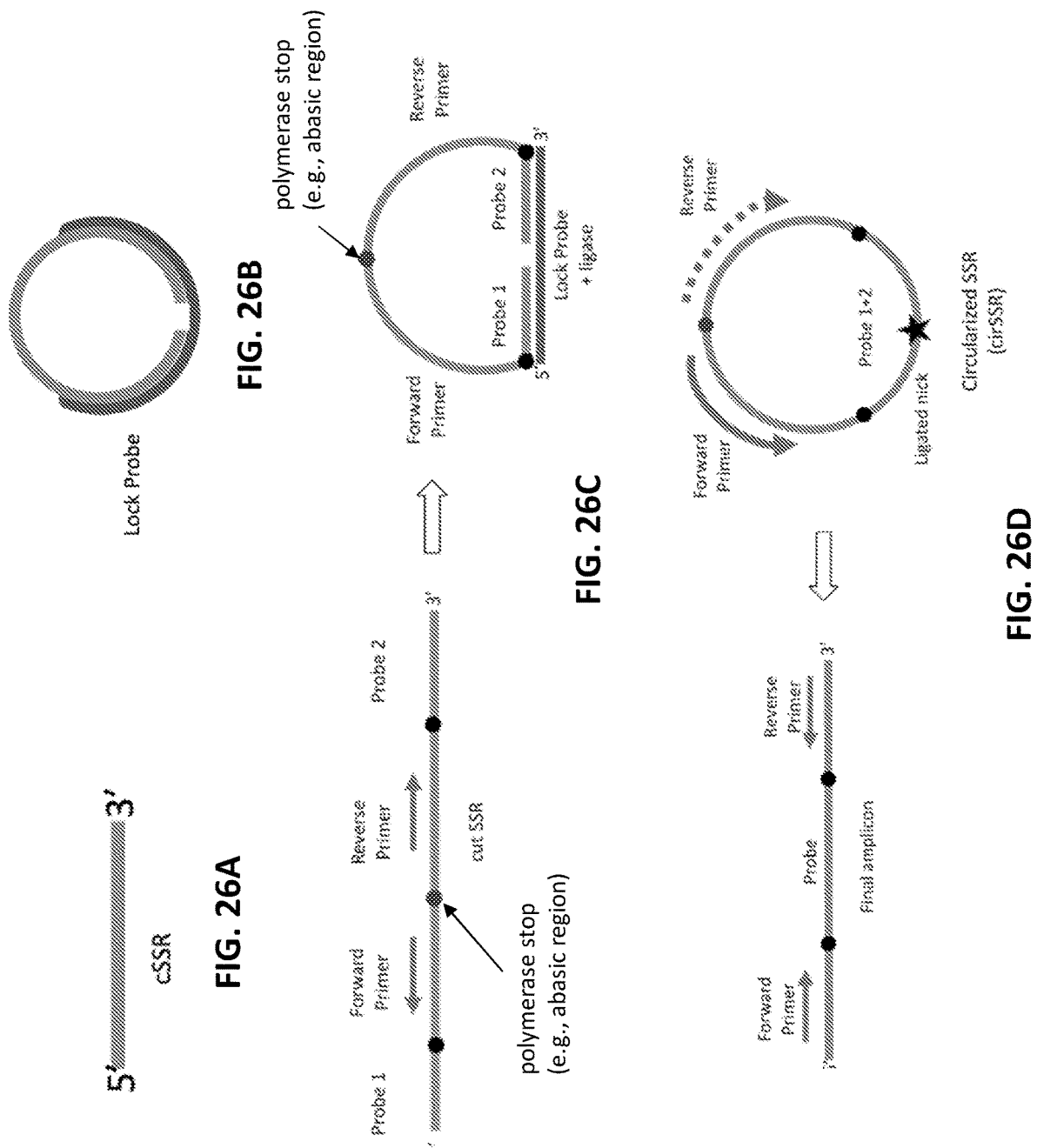
FIG. 26A-26D, which is similar to FIG. 21B, schematically illustrates one example of an SSR lock probe (FIG. 26A) that may be circularized using a lock probe (FIG. 26B, 26C) and used to quantify a genetic signal (FIG. 26D), as described herein.

For example, a sequence conversion assay may start with an extracted subject (or pooled subjects) sample, e.g., of cell free DNA (cfDNA). SCP probes are then added to extracted cfDNA, which may be heated to denature the double-stranded cfDNA and cooled to allow specific annealing of SCP probes to target alleles within the cfDNA. Nuclease (e.g., restriction enzyme) is then added, and incubated to cleave the hybridized SCP probes at the pre-determined position, releasing the SSR portion of the SCP probe (cut SSR, or cSSR) only from those SCP probes whose TSR regions have hybridized to target regions of the cfDNA. A lock probe and ligase may then be added to circularize the cSSR. Optionally non-circular ssDNA and dsDNA may be digested; this step is not be necessary, particularly where the "primer away" amplicon configuration (as shown in FIGS. 21C and 26C-26D) is utilized. The circularized SSR may optionally be amplified. The supernatant containing circular cSSR may be used in a dPCR detection reaction. For example, the inverse orientation of the forward and reverse primer and probe binding sites on the SSR may ensure that only circularized SSRs (cirSSRs) can be amplified.

Thus, described herein are methods of forming sequence conversion probes (SCPs) that may be used to form a functional SCP. These SCPs may work in any of the sequence conversion assay. Although specific examples of sequences for SCPs, and the SSRs and TSRs that form them are provided, for example in SEQ ID Nos. 1-5 and 8-75, it should be understood that the methods described herein teach and enable one of skill in the art to make SCPs that will work with the sequence conversion assays described herein and are not limited to a particular sequence. SCPs having virtually any sequence that conforms to the properties described herein for selecting and combining the TSR and SSR will work.

For example, an SCP may generally include a target-specific region (TSR) extending between 15 and 80 base pairs (bp), wherein a polynucleotide sequence of the TSR is at least 80% identity (e.g., at least 81%, at least 82%, at least 83%, at least 84%, at least 85%, etc.) to only a single region of one chromosome within a target (e.g., human) genome. In some cases the polynucleotide sequence of the TSR may be between 15 and 50 bp, between 15 and 45 bp, between 15 and 35 bp, between 15 and 30 bp, etc. Preferably the TSR is between 15 and 35 bp. As will be described in greater detail below, the TSR is homologous (e.g., having a signification identity) to only a single region of one chromosome within a target genome, so that the TSR will bind with reasonable affinity to only a single site within the genome. As described in greater detail, the TSR may be selected so that it occurs on a known chromosome (e.g., chromosome 21) in the genome. Although the examples described herein are specific to assays of human genomes, it should be understood that these assays may be directed to targets for other genomes (including other animal genomes, plant genomes, etc.).

The TSR is selected explicitly to include within the sequence of the TSR a cognate restriction site for a type IIs restriction enzyme. Example of type IIs restriction enzymes that may be used are provided herein. In some examples the cut site for the restriction enzyme may be at or near a first end of the TSR. The TSR may have a GC content of greater than 50%.

As mentioned, the TSR probe is specific to a given chromosome and occurs only once in that chromosome. Typically, multiple instances of SCPs are included that have the same SSR but different TSRs, as described above. All of the TSRs within a set of SCPs (including a variety of different TSR probes) may have the same restriction site. The restriction site (the cognate restriction site for a type IIs restriction enzyme) may be positioned in approximately the same position in all of the TSRs of the set of SPCs. For example, the cognate site may be positioned with the cut site within 8 bp (e.g., within 7 bp, within 6 bp, within 5 bp, within 4 pb, within 3 bp, within 2 bp, within 1 bp, etc.) of the 3' end of the TSR where the TSR is coupled to the SSR. For example, all of the TSRs may have the cognate restriction site within about 10 bp downstream and upstream of the 5' and 3' ends of the TSR, respectively. The cognate site may be adjacent to the end (e.g., the 5' end) of the TSR where the TSR is coupled to the SSR. In some examples all of the TSRs of the set of TSRs within the set of SCPs have approximately the same size (e.g., about 13 bp, about 14 bp, about 15 bp, about 16 bp, about 17 bp, about 18 bp, about 19 bp, about 20 bp, about 21 bp, about 22 bp, about 23 bp, about 24 bp, about 25 bp, about 26 bp, about 27 bp, about 28 bp, between about 13-50 bp, between about 15-40 bp, between about 15-35 bp, between about 15-30 bp, between about 15-25 bp, etc.).

The different TSRs of a set of SCPs are each unique and non-overlapping; the TSRs of a set of SCPs do not overlap with each other (e.g., all hybridize to different, non-overlapping regions of the genome.

In general, the GC content of each TSR is greater than 50%, and the Tm (melting temperature) for each TSR is typically within a set range (e.g., greater than 55 degrees C., greater than 56 degrees C., greater than 57 degrees C., greater than 58 degrees C., greater than 59 degrees C., between about 55-65 degrees C., between about 57-67 degrees C., between about 57-65 degrees C., etc.).

Finally, as will be described in greater detail below, each TRS probe may be selected to minimize their predicted secondary structure. The secondary structure may be calculated or approximated by calculating a minimum free energy (MFE) in kcal/mol and determining if the cognate restriction site for a type IIs restriction enzyme within the TSR prove is not part of a hairpin loop or otherwise blocked or disrupted by second structure. This determination may also or alternatively be made at the SCP stage, once the putative TSR has been combined with the SSR.

The sequence-specific region (SSR) may have a poly-nucleotide sequence extending greater than 40 bp (e.g., greater than 45 bp, greater than 50 bp, greater than 55 bp, between 40 and 100 bp, between 40-90 bp, between 40-80 bp, between 50-100 bp, between 50-90 bp, between 50-80 bp, etc.). The polynucleotide sequence of the SSR sequence does not occur in the target genome. For example, the SSR may have a sequence that is engineered and compared to the target genome (e.g., the human genome, including and non-chromosomal DNA, such as mitochondrial DNA) to confirm that it does not appear within the sequence of the target genome (so that it would not hybridize to the target genome). The SSR may have a CG content of greater than 50%.

In general, the end of the TSR nearest to the cut site of the type IIs restriction enzyme region (e.g., a 5' end) may be joined to the SSR. As already mentioned above, the cognate restriction site is not part of a hairpin structure in the assembled SCP.

In general the SSR of each SCP in a set of SCPs may be the same polynucleotide sequence and may share a set of forward and backward primers that hybridize with high selectively and efficiency. For example, the SSR may include a forward primer region and a reverse primer region.

The SSR may include one or more regions that prevent or block enzymatic extension (e.g., polymerase) based on a modification of the polynucleotide sequence. For example, any of the SSRs may include a forward primer region and a reverse primer region and an abasic region between the forward primer region and the reverse primer region.

An abasic region (also referred to as an abasic site or an AP site, or apurinic/apyrimidinic site) may occur naturally by hydrolysis of nucleoside residues in DNA to generate abasic sites. Most commonly, dA sites are hydrolyzed causing depurination and leading to abasic residues. These sites may be included in engineered polynucleotides, including the SSRs described herein. For example, a 1,2'-Dideoxyri-bose modification can be used to insert a single base space into a DNA oligonucleotide sequence, which replicates the loss of base pairing ability by a nucleotide, which can occur naturally through depurination or other mechanisms. A C3 Spacer phosphoramidite (iSpC3) can be used as a spacer arm in an oligonucleotide. The compounds may be added in multiple additions when a longer spacer is required. 3'-Spacer C3 CPG or phosphoramidite may also act as a blocker of exonuclease and polymerase and may be used to introduce a stable abasic site within an oligonucleotide. For example, dSpacer CE Phosphoramidite (5'-O-Dimethoxytri-tyl-1',T-Dideoxyribose-3'-[(2-cyanoethyl)-(N,N-diisopro-pyl)]-phosphoramidite) may be used. dSpacer is also referred to as an abasic site, tetrahydrofuran (THF), or apurinic/apyrimidinic (AP) site. It can be incorporated into an oligonucleotide sequence internally, or at the 5' or 3' end of a sequence. Any number of spacers may be used to form the abasic region/site (e.g., 1, 2, 3, 4, 5, etc.).

Figure 23A:
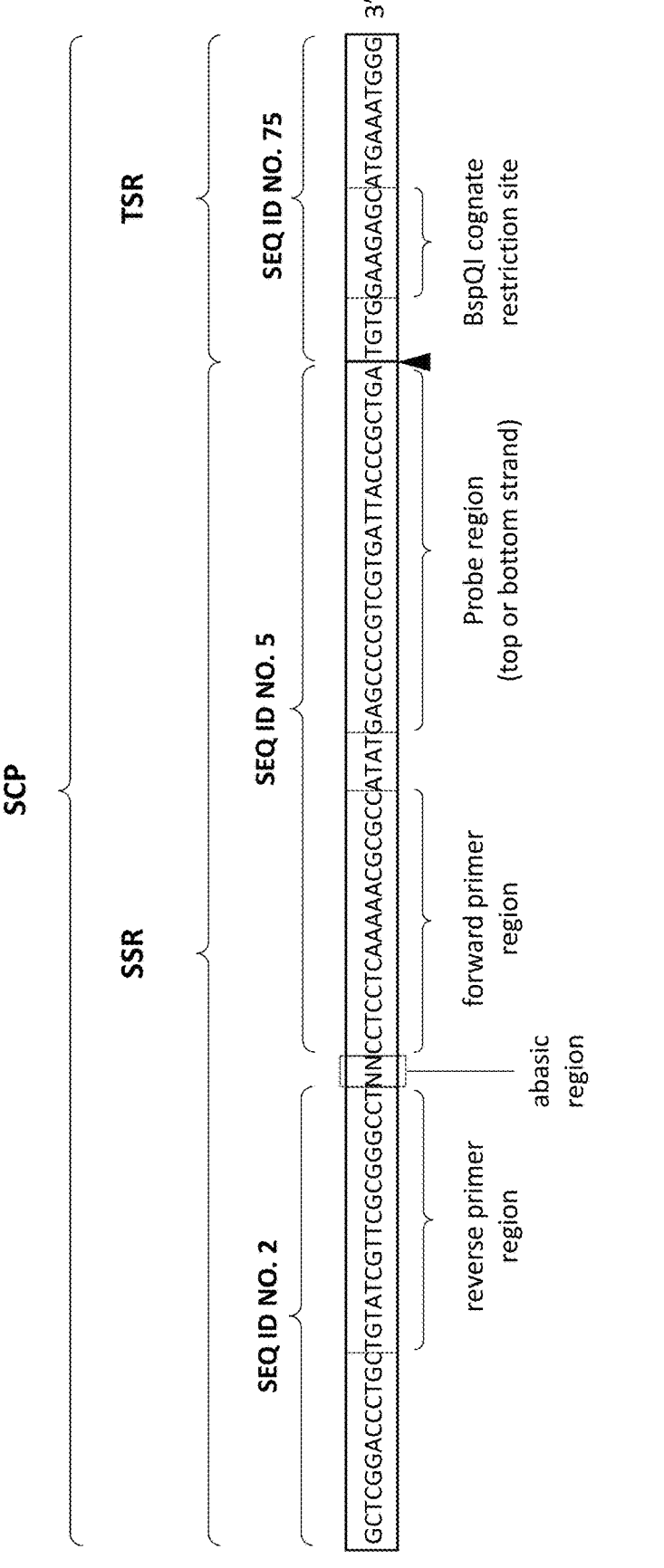
FIG. 23A illustrates an example of an SCP formed as described herein, including a SSR (having an abasic region between a revere primer region and a forward primer region), and a TSR including a BspQI cognate restriction site.

FIG. 23A schematically illustrates one example of an SCP as described herein. In this example, the SCP includes an SSR and a TSR. The SSR in this example is similar to that shown in SEQ ID No. 4, but includes an abasic region between a reverse primer region and a forward primer region. For example, the SSR may be constructed by con-necting the polynucleotide region before the abasic region (SEQ ID NO. 2) with the polynucleotide region after the abasic region (SEQ ID NO. 5), in which the abasic region links the two polynucleotide regions. This SSR is then coupled to a TSR (e.g., SEQ ID NO. 75), which was constructed as described herein from a unique BspQI site on human chromosome 21. The SSR also includes two probe regions that may hybridize to a linker polynucleotide to circularize the SSR after it has been cut, as described above.

Figure 23B:
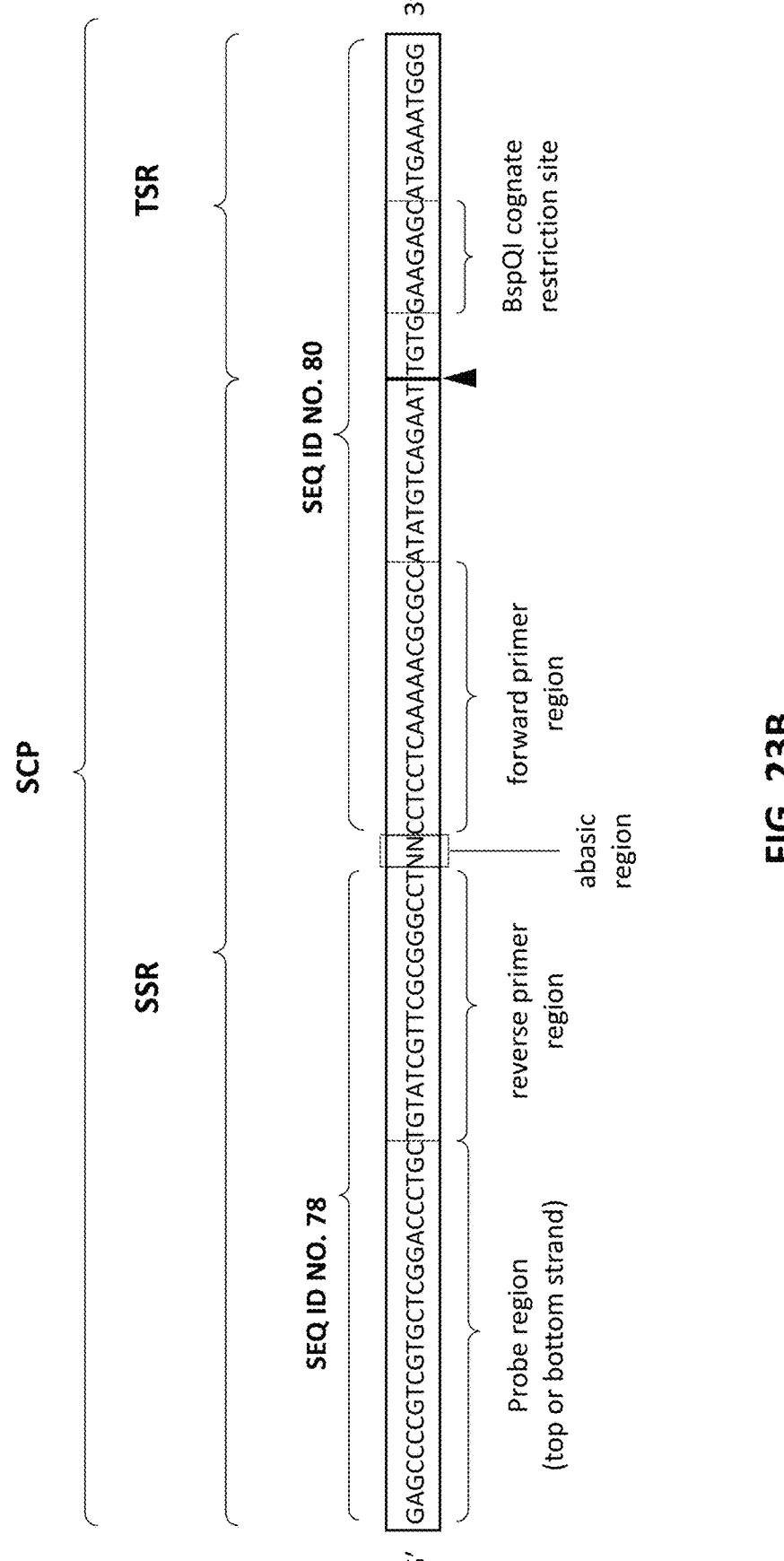
FIG. 23B illustrates an example of an SCP as described herein, similar to that shown in FIG. 23A, and including a 5' SSR probe orientation.

FIG. 23B schematically illustrates another example of an SPC as described herein, using an SSR region that is configured as in SEQ ID NO. 78 jointed to SEQ ID NO. 80 by an abasic site.

Figure 24:
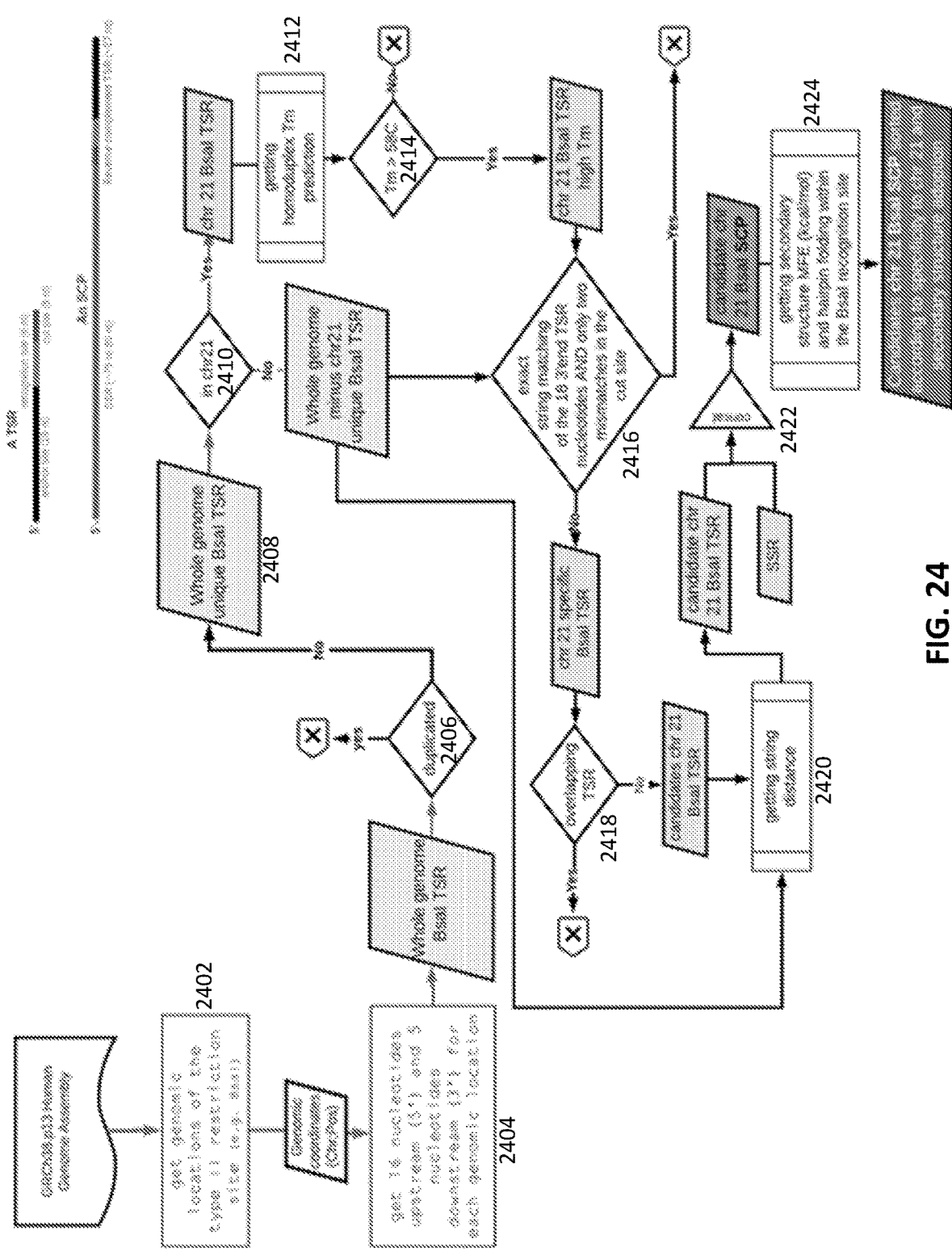
FIG. 24 schematically illustrates one example of a method for identifying one or more TSRs within a genome (e.g., a human genome) that occur only once, and on a known chromosome as described herein.

SEQ ID NOS. 8, 12, 15, 18, 21, 24, 27, 30, 33, 36, 39, 42, 45, 48, 51, 54, 57, 60, 63, 66, 69, 72, or 75 illustrate examples of an TSRs that were engineered using the meth-ods described herein. FIG. 24 illustrates one example of the method of designing a TSR (or a set of TSRs). The sche-matic shown in FIG. 24 uses a target genome. In this example, the target genome is GRC38.p13 human genome assembly (e.g., the full GCF_000001405.26_GRCh38_genomic.fna), but any genome sequence listing may be used.

This GCF_000001405.26_GRCh38_genomic.fna fea-tures all the other short contigs (~430 of them) that have not been assigned yet to a chromosome. In the example shown in FIG. 24, the target chromosome is human chromosome number 21, and the type IIs restriction enzyme that is used is BsaI. The method described herein is the same regardless of the type IIs restriction enzyme or chromosome used.

The target genome is scanned for all locations within the genome having the target type IIs restriction site 2402 (e.g., in this example, BsaI), to provide genomic coordinates for these sites. A fixed region upstream and downstream (e.g., 16 nucleotides upstream, 5', and 5 nucleotides downstream, 3') 2404 were chosen from the genomic location, and putative TSRs were then vetted to remove any that included a duplicate 2406, since each TSR must be entirely unique within the entire genome 2408. The putative TSRs were then filtered to identify just those that are present on the target chromosome 2410, in this example, chromosome 21. The resulting putative TSRs were then examined to identify their Tm (e.g., using a homoduplex Tm prediction model) 2412. Any putative TSRs having a predicted Tm of less than 58 degrees C. were eliminated. The resulting ("high Tm" puta-tive TSRs were then examined to confirm that they were unique within about 80% identity with the entire genome; for example a mismatch of more than two (or in some cases more than 3, more than 4, mover than 5, etc.) was allowed to remain a putative TSR, otherwise they were eliminated 2416. Calculations of how many hits a given candidate e.g. chr 21 BsaI TSR, has against the rest of a genome with a given number of mismatches may be used as a filter for potential cross-reactivity. Any overlapping putative TSRs were also eliminated 2418. The similarity between all puta-tive TSRs 2420 and the rest of the genome TSR was also estimated based on their string distance using an approxi-mate string matching method. The putative TSR(s) were then combined with the intended SSR (see below) 2422 to form putative SCPs, and the putative SCP sequences were examined to eliminate any having secondary structure 2424 that would inhibit enzymatic activity by the target type IIs restriction enzyme (e.g., BsaI).

Figure 28:
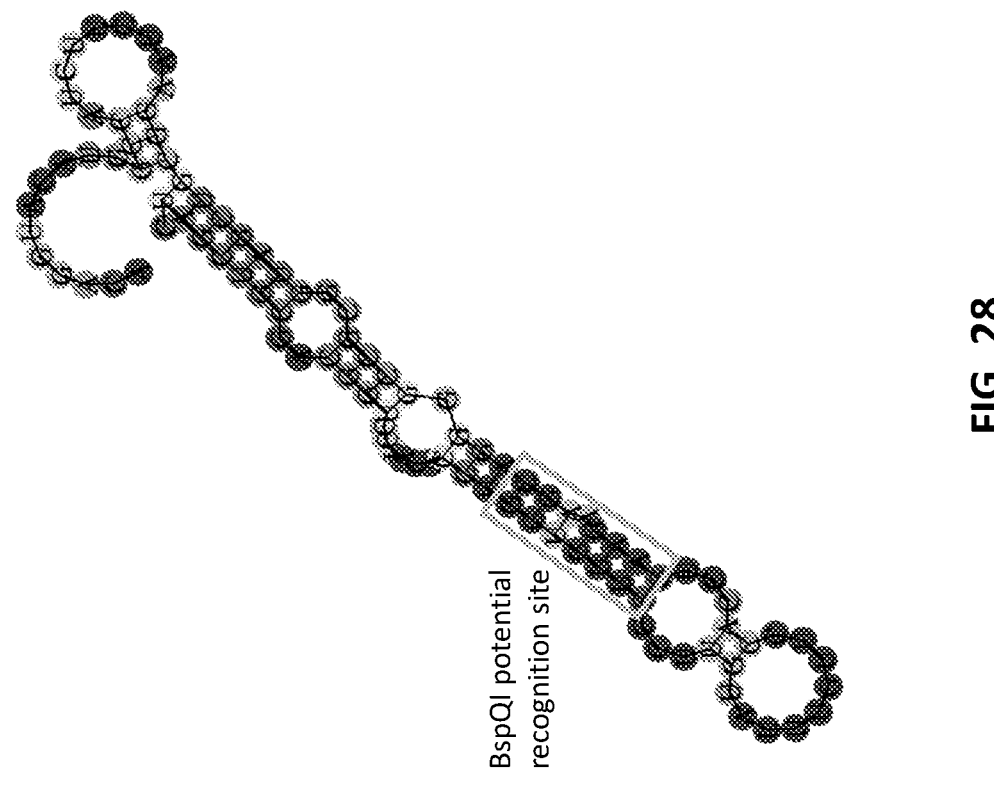
FIG. 28 illustrates one example of an SCP showing a predicted secondary structure in which a cognate restriction site for a type IIs restriction enzyme on the TSR is not within a hairpin loop region or otherwise blocked (or occluded), as by a secondary structure that prevents interaction with the type IIs restriction enzyme.

Secondary structure may be estimated and calculated using any appropriate method, a variety of which are known and available to those of skill in the art. For example, secondary structure and hairpin folding at or near the type IIs restriction enzyme cognate site may be determined using RNAFold ViennaRNA Package. For example, FIG. 28 illus-trates one example of a predicted secondary structure that may be used for an SCP. In FIG. 28, the predicted second structure was calculated using RNAFold ViennaRNA Pack-age; in this example the type IIs restriction enzyme cognate of the putative TSR is predicted to adopt a stable secondary structure and has a high GC content. The BspQI cognate restriction site is not within a hairpin region. Thus, the SCPs may be selected to identify only those that meet the criterion above, including that there is no significant secondary struc-ture (and in particular no hairpin loops) including the cognate restriction enzyme recognition site.

In the example shown in FIG. 24, when the target type IIs restriction enzyme was BasI and the target chromosome was chromosome 21, the method initially identified 1,740,533 BsaI putative TSRs in the GRCh38 genome. Of these, 979,551 are unique, and 11,393 of these putative TSRs are in chromosome 21, but only 11,290 had a Tm greater than 58 degrees C. From these, only 325 putative TSRs were non-overlapping and non-cross reactive to other chromo-somes. Of these 325 putative TSRs, secondary structure predictions identified a subset that were substantially free of secondary structure including or occluding the type IIs restriction enzyme recognition (and cut) site. SEQ ID NOS. 8, 12, 15, 18, 21, 24, 27, 30, 33, 36, 39 and 75 illustrate examples of TSRs identified using the criterion above, that may be used as part of the sequence conversion assay described herein. A similar process was used to identify other putative TSRs when a different type IIs restriction enzyme (e.g., BspQI) was used. SEQ ID NOS.: 42, 45, 48, 51, 54, 57, 60, 63, 66, 69, and 72 illustrate the TSRs identified in this manner.

As mentioned, any appropriate type II restriction enzyme may be used. These enzymes may be selected from the list of commercially available enzymes having a recognition site that is 6 or 7 bases long. The enzymes should be heat inactivated, and preferably recombinant. The recognition site for the enzyme should occur often enough (ideally, e.g., more than about 500 times) on each target chromosome (e.g., chromosome 13, 18 and/or 21), which may support assay statistical requirements. Preferably the enzyme may hybridize at an elevated temperature (e.g., 45 degrees C., 50 degrees C., etc.), such as enzymes which work well around 50° C. Restriction enzymes that have a low salt tolerance and/or that cannot be heat inactivated and/or that had a high "star activity" (e.g., a form of lack of unspecific cleavage activity) were eliminated as options for use in the TSR design.

Figure 25:
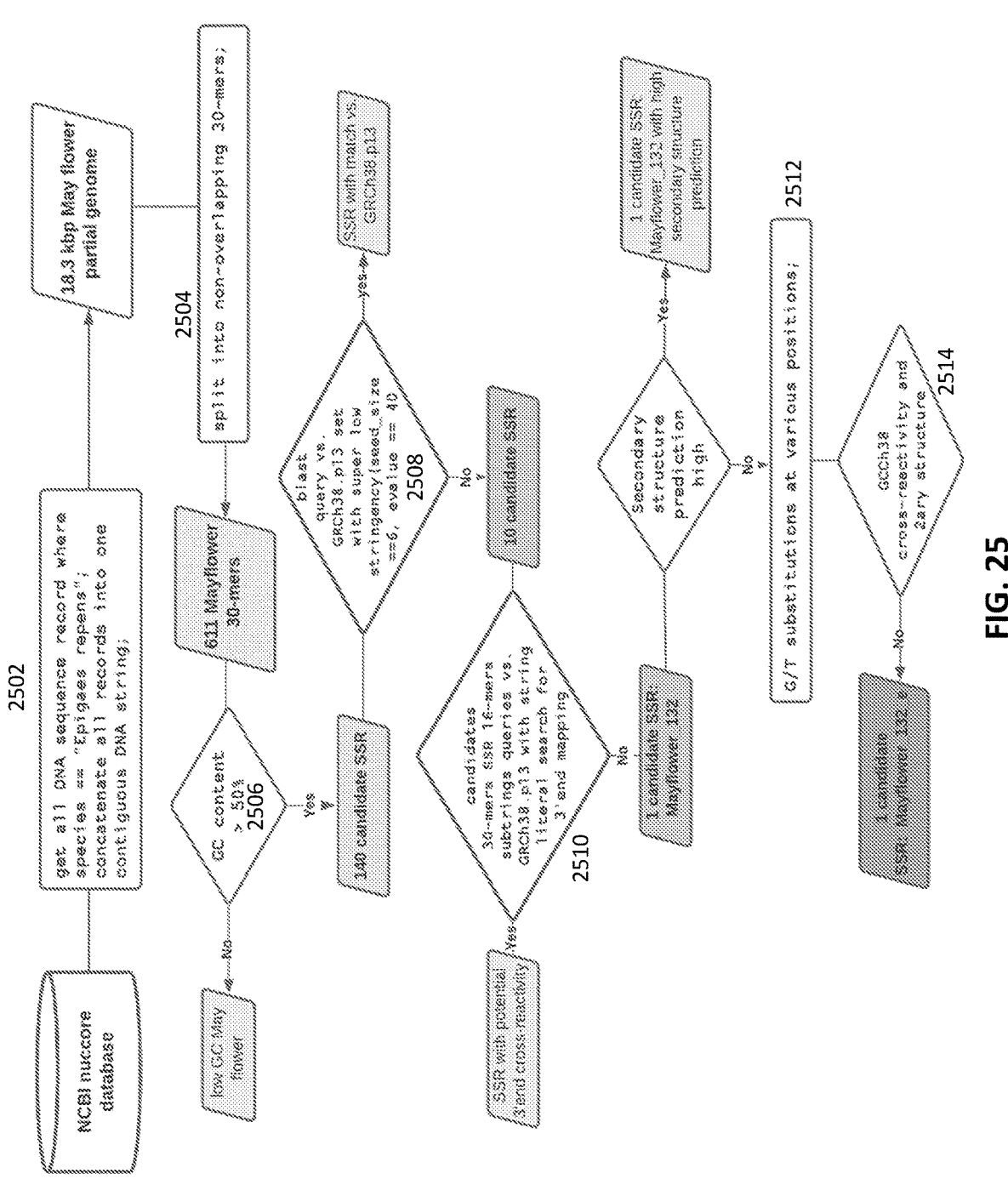
FIG. 25 schematically illustrates one example of a method for identifying an SSR as described herein.

A parallel process may also be used to select the SSR. Although a single SSR may be used, multiple putative SSRs may be formed. For example, In FIG. 25 the schematic illustrates one example of a method of designing an SSR that may be combined with any of the TSRs. The SSR typically has a GC content that is greater than about 50% and may be formed of short DNA sequences (e.g., 30-mer) that re unlikely to cross-react with the target genomic DNA (e.g., human genomic DNA) in the context of a nucleic acid amplification test. In this example, the method may begin by identifying a non-target genome, preferably from a different kingdom or phylum 2502. For example, in FIG. 25, a plant species (e.g., Epigaes repens, May flower) was used, and divided into non-overlapping 30-mer stretches 2504. These different putative 30-mer stretches were then examined to determine their melting temperature (Tm); those with Tm lower than about 50 degrees were eliminated and those with Tm higher than 50 degrees C. were kept 2506. In this example, about 140 candidate SSRs were identified. These putative SSRs were then examined to confirm that there were not present in the human genome 2508 (e.g., using a blast query against the target human genome used). Only those that were unique (some mismatching may be allowed, such as 2 or fewer mismatches, 3 or fewer mismatches, 4 or fewer mismatches, 5 or fewer mismatches, 6 or fewer mismatches, 7 or fewer mismatches, 8 of fewer mismatches, etc.) were then kept a putative SSRs. In some examples, larger (e.g., larger than 30 mer) candidate SSRs may be examined, such as 40-mer, 50-mer, etc. In some examples smaller candidate SSRs may be expanded by combining with portions of other novel sequences. The putative SSRs may then be examined against the human genome with lower stringency, e.g., to allow some mismatches (e.g., by running sub-regions of the putative SSR) 2510. The resulting candidate(s) may then be analyzed to determine the secondary structure prediction as described above. Candidates having a low secondary structure prediction may be used as SSR sequence. Alternatively, if a candidate at this stage does have a high secondary structure prediction, the sequence of the candidate SSR may be modified by performing G/T substitutions at one or more position (including random positions) and the resulting modified sequence may be compared against the target genome again 2514.

The SSR identified in SEQ ID NO. 1 shows one example of an SSR; alternative SSRs are shown in SEQ ID NOS. 2-5. For example, SEQ ID NO. 2 shows an SSR portion. This portion may be combined with the SSR portion of SEQ ID NO. 3 or SEQ ID NO. 5 (e.g., connected by an abasic region as shown in FIG. 23A). As mentioned, any of the identified SSRs may be modified to include a short region that disrupts replication over, particularly between opposite-facing (away facing) forward and reverse polynucleotides for later detection amplification. As illustrated in FIGS. 26-26D, an SSR may (once cut from the TSR) be circularized as described previously and assayed using the general primers (forward and reverse primers) that, once linearized, allow amplification, as described above.

For example, detection may be performed using digital PCR (dPCR). In some examples the system may include TaqMan probes. The TaqMan probe site may be engineered on the SSR so that the TaqMan probe does not interfere with the method described herein. For example, TaqMan probes may be positioned at the 3' end of the SSR, rather than at the SSR 5' end or straddling the cut site, both of which may interfere with the method. For example, if the TaqMan probe straddles the cut site, the TaqMan probe may also act to bridge the forward and reverse primers, resulting in undesired amplification (and therefore undesired PCR signal). Alternatively, it has been found that positioning the TaqMan probe site at the SSR 5' end may result in sequestering of the TaqMan probe.

Figure 27:
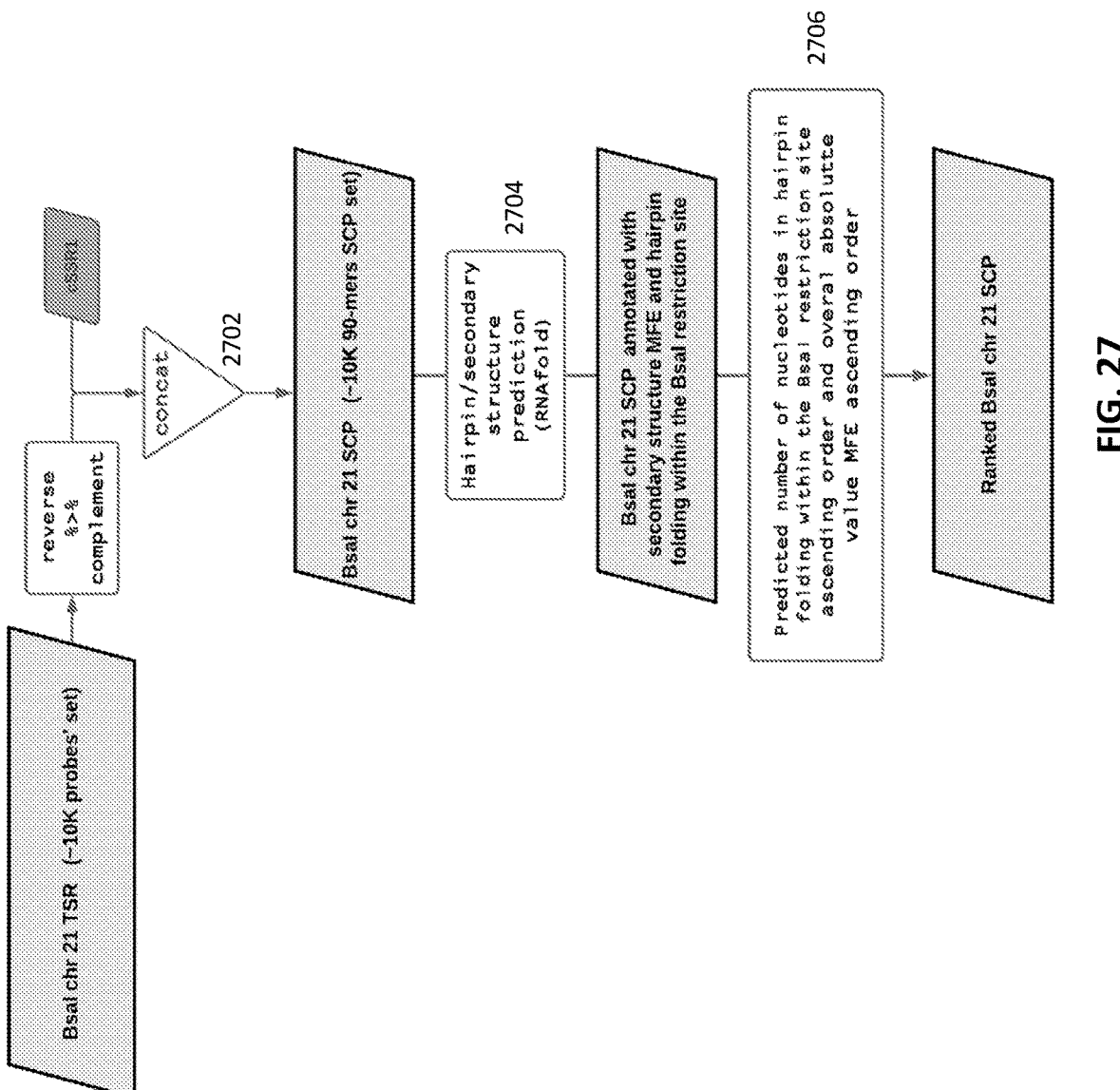
FIG. 27 schematically illustrates one example of a method of identifying an SCP for use with any of the methods described herein, which may be used with the methods of determining the component SSR and TSR regions, such as shown in FIGS. 24-25.

FIG. 27 illustrates the method of determining the final SCPs from the SSR(s) and TSRs described above. The SCPs may be engineered as described to be both unique (e.g., so that the TSR region hybridizes to a single site unique to a single chromosome) and so that the SSR does not hybridize to any of the target genome. Further, the SCP may be configured so that the secondary structure is stable and does not block or occlude the restriction site (e.g., the cognate restriction site or cognate restriction site and cut site). For example, in FIG. 27, the reverse complement of each putative TSR region is combined with the SSR identified as described above to form the SCP 2702. The secondary structure of the SCP is then calculated as described 2704. For example, hairpin/secondary structure predication may be performed on the SCP to determine if the restriction site is or is not (or how much it is) blocked or occluded by the predicted secondary structure. A numeric score may be applied, e.g., based on minimum free energy (MFE) and a threshold applied to determine if the SCP is valid. For example, the absolute minimum free energy (absolute value of the calculate minimum free energy) may be chosen to be less than a threshold value (e.g., less than 20, less than 25, less than 30, less than 35, less than 40, less than 45, less than 50, less than 55, less than 60, less than 65, less than 70, less than 75, less than 80, less than 85, less than 90, less than 95, less than 100, etc.) kcal/mol.

An SCP may be an approximately 90 nucleotide long single strand DNA with a high GC content per design, which is prone to adopt stable secondary structure. Examples of SCPs determined as described above for human chromosome 21 are provided in SEQ ID NOS. 8, 12, 15, 18, 21, 24, 27, 30, 33, 36, 39, 42, 45, 48, 51, 54, 57, 60, 63, 66, 69, 72, or 75. Partial SCPs, which may be linked, e.g., via an abasic region, to additional SSR regions (such as shown in SEQ ID NO. 10) are shown in SEQ ID NOS. 11, 14, 17, 20, 23, 26, 29, 32, 35, 38, 41, 44, 47, 50, 53, 56, 59, 62, 65, 68, 71, 74 and 77.

FURTHER EXAMPLES

The various methods and steps described herein were examined using sample primers and template as described herein. One example of a workflow (referred to herein as a "full primer away circularization workflow") was demonstrated using an SCP ("SCR0083") which includes a TSR at the 3' end with a BspQI recognition sequence and is specific for Chromosome 21 at site NC_000021.9_27305245.

In this example, SCP SCR0083 (0.5 nM; SEQ ID No. 83; IDT) was annealed to target SCR0113 (SEQ ID No. 84, 3.4e5 copy; IDT) in 10 mM Tris-HCl, 1 mM Na2-EDTA, 100 mM NaCl, 10 mM MgCl2, pH 8.0 (40 ul) by heating to 95° C. for 5 min, cooling at 0.015 C/sec to 50° C. and holding for 5 min. The SCP annealed to its TSR synthetic target was digested with BspQI (20 U; NEB cat #R0712) for 60 min at 50° C. in a final digestion buffer comprised of 50 mM Tris-HCl, 100 mM NaCl, 10 mM MgCl2, 100 mg/ml BSA. The digestion was followed by a 20-minute heat inactivation step at 80° C. The SSR of the digested SCP was then ligated by treatment with Hi-T4 ligase (60 U; NEB cat #M2622) for 70 minutes at 50° C. in 50 mM Tris-HCl, 20 mM MgCl2, 1.5 mM ATP, 0.5 nM Lock Probe SCR0080 (SEQ ID No. 85; IDT). The ligation was followed by a 10 min heat inactivation step at 65° C. The circularized SSR was then amplified and detected by real-time PCR using TaqMan Fast Advanced MasterMix (ThermoFisher cat #4444556), 200 nM forward and reverse primers (SSR1_FP, SEQ ID No. 86; SSR1_RP, SEQ ID No. 87; IDT) and 100 nM TaqMan probe SCR0078 (SEQ ID No. 88; IDT) by denaturation at 95° C. for 20″ followed by 40 cycles of 95° C. for 1″ and 60° C. for 20″ QuantStudio Real Time PCR System (ThermoFisher Scientific).

Figure 30:
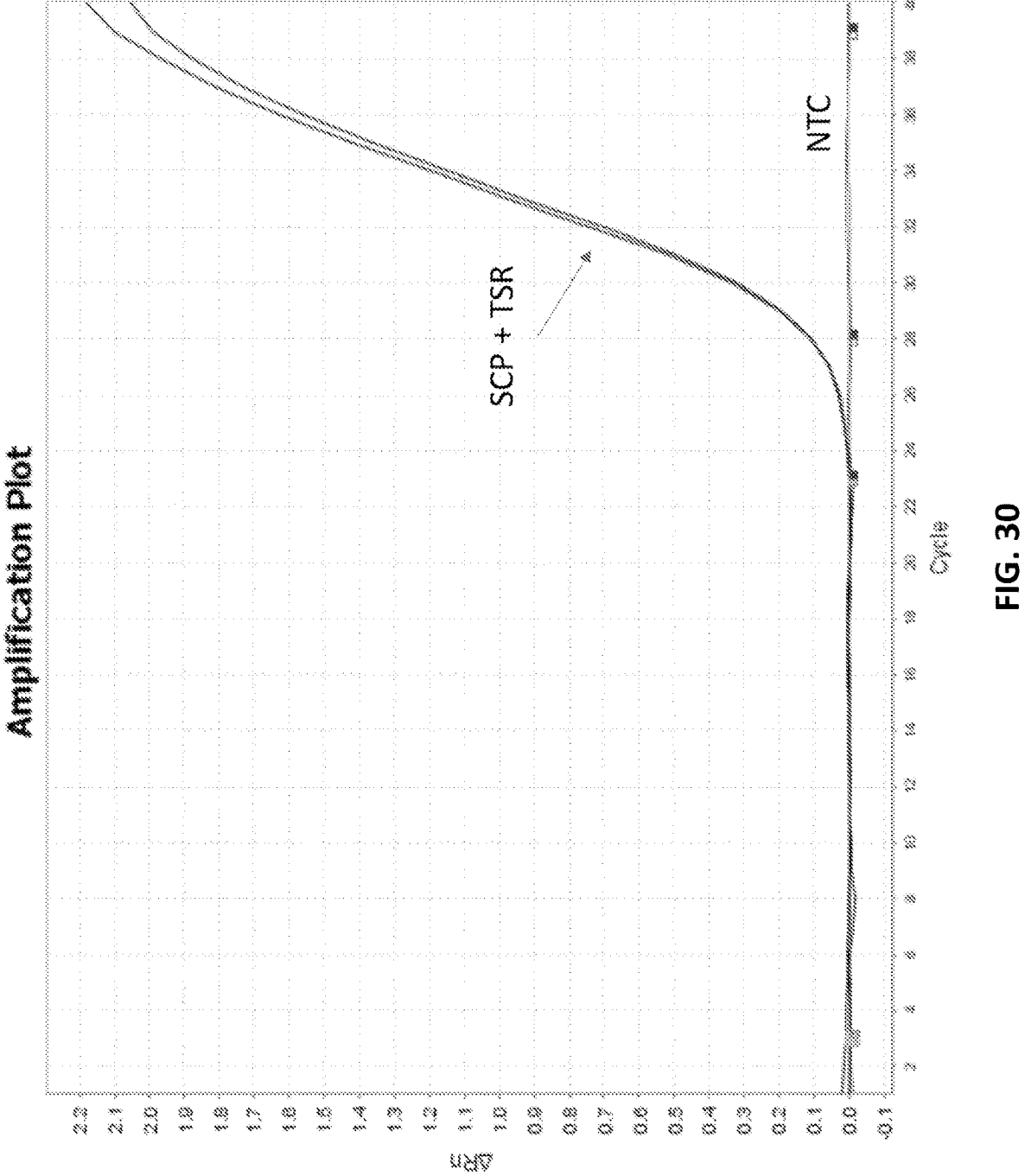
FIG. 30 is an amplification plot illustrating one example of a sequence conversion method as described herein.

Amplification plots for digested, circularized chromosome 21-specific Sequence Conversion Probe SCR0083 (SEQ ID No. 83) using the "primer away" qPCR assay for SCR0083 and a no template control (NTC) are shown in FIG. 30.

This workflow illustrates the multiple, sequential steps completed successfully, starting with the annealing of the SCP to target, then cleaving the SCP by the specific restriction endonuclease (BspQI in this example), thereby separating the TSR from the SSR, and ligating the resulting cleaved SSR (cSSR) into a covalently closed single-stranded circular DNA and, finally, detecting the circularized product by "primer away" qPCR.

In some examples the TSR may be cut so that there is no TSR (no target sequence) in the resulting cSSR.

Multiplex SCR with qPCR Readout was also examined. Highly efficient and specific amplification and detection of two SSRs with a universal primer pair and two different TaqMan probes, one labeled with FAM, the other labeled with HEX, was demonstrated. TaqMan PCR was used as the detection method in this example. The respective probes are highly specific for their intended SSR and do not cross-react with the unintended SSR or with human genomic DNA.

In this example, synthetic Signal Specific Region (SSR) oligonucleotides SCR0076 (SEQ ID No. 89; IDT) and SCR0136 (SEQ ID No. 90; IDT) were amplified in presence of common forward and reverse primers and detected with either the cognate or non-cognate TaqMan probe, i.e. SCR0078 (SEQ ID No. 88) for SCR0076 (SEQ ID No. 89) or SCR0134 (SEQ ID No. 91) for SCR0136 (SEQ ID No. 90). The SSR targets correspond to the SSRs in the Sequence Conversion Probe (SCP) found in SCR0083 (SEQ ID No. 83) (for chromosome 21) and SCR0133 (SEQ ID No. 99, for chromosome 18) after cleavage and circularization via ligation.

Additionally, specificity was examined by using either water (no template control; NTC) or in the presence of 100 ng of human genomic DNA derived from HeLa cell line (gDNA; NEB; cat #N4006). The real-time PCR was performed using TaqMan Fast Advanced MasterMix (ThermoFisher cat #4444556), 200 nM forward and reverse primers (SSR1_FP, SEQ ID No. 86; SSR1_RP, SEQ ID No. 87; IDT) and 100 nM TaqMan probe SCR0078 (SEQ ID No. 88; IDT) or SCR0134 (SEQ ID No. 91; IDT) by denaturation at 95° C. for 20″ followed by 40 cycles of 95° C. for 1″ and 60° C. for 20″ on the QuantStudio Real Time PCR System (ThermoFisher Scientific).

Figure 31A:
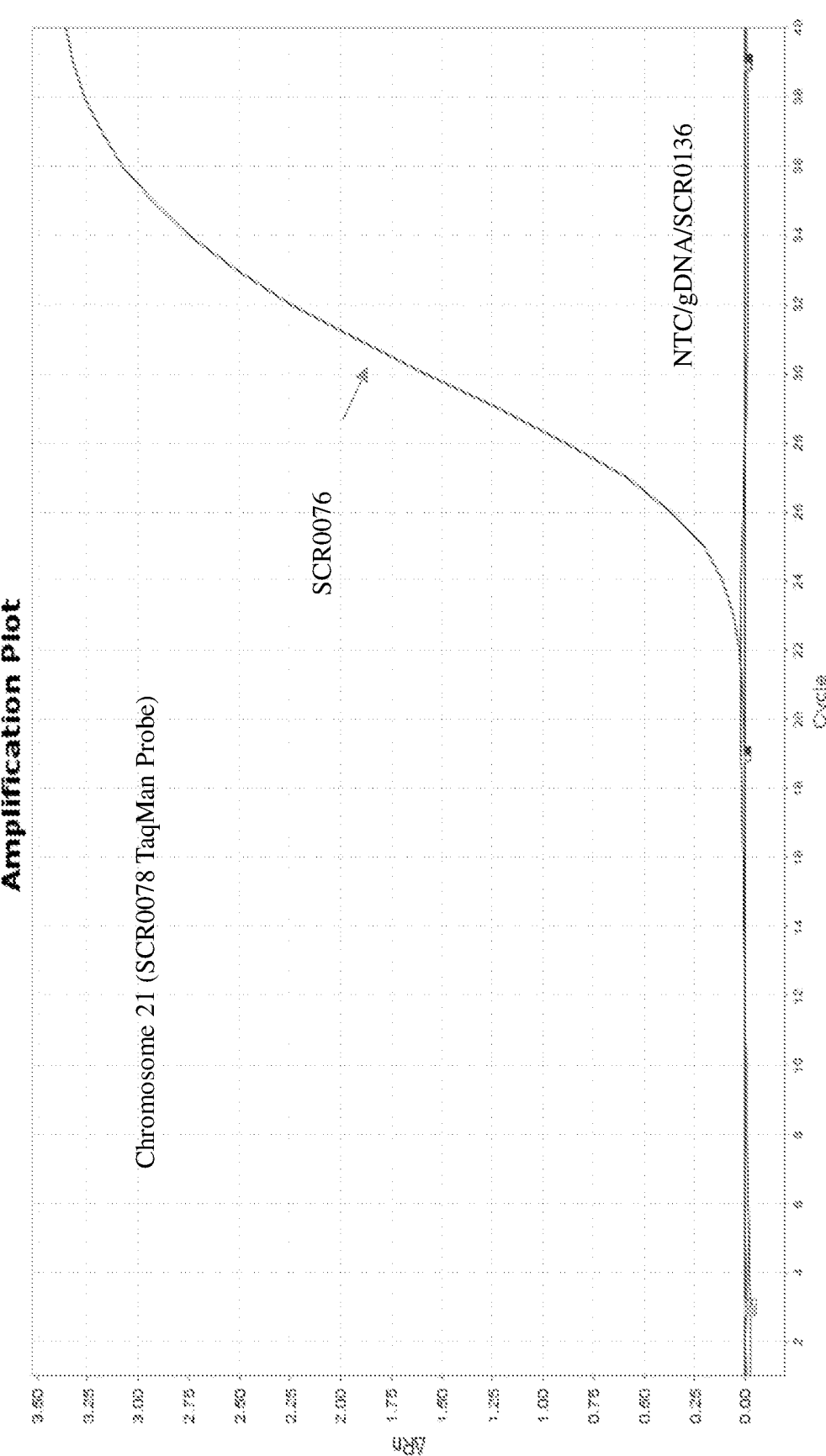
FIGS. 31A-31B show amplification plots for one example of a sequence conversion method as described herein.
Figure 31B:
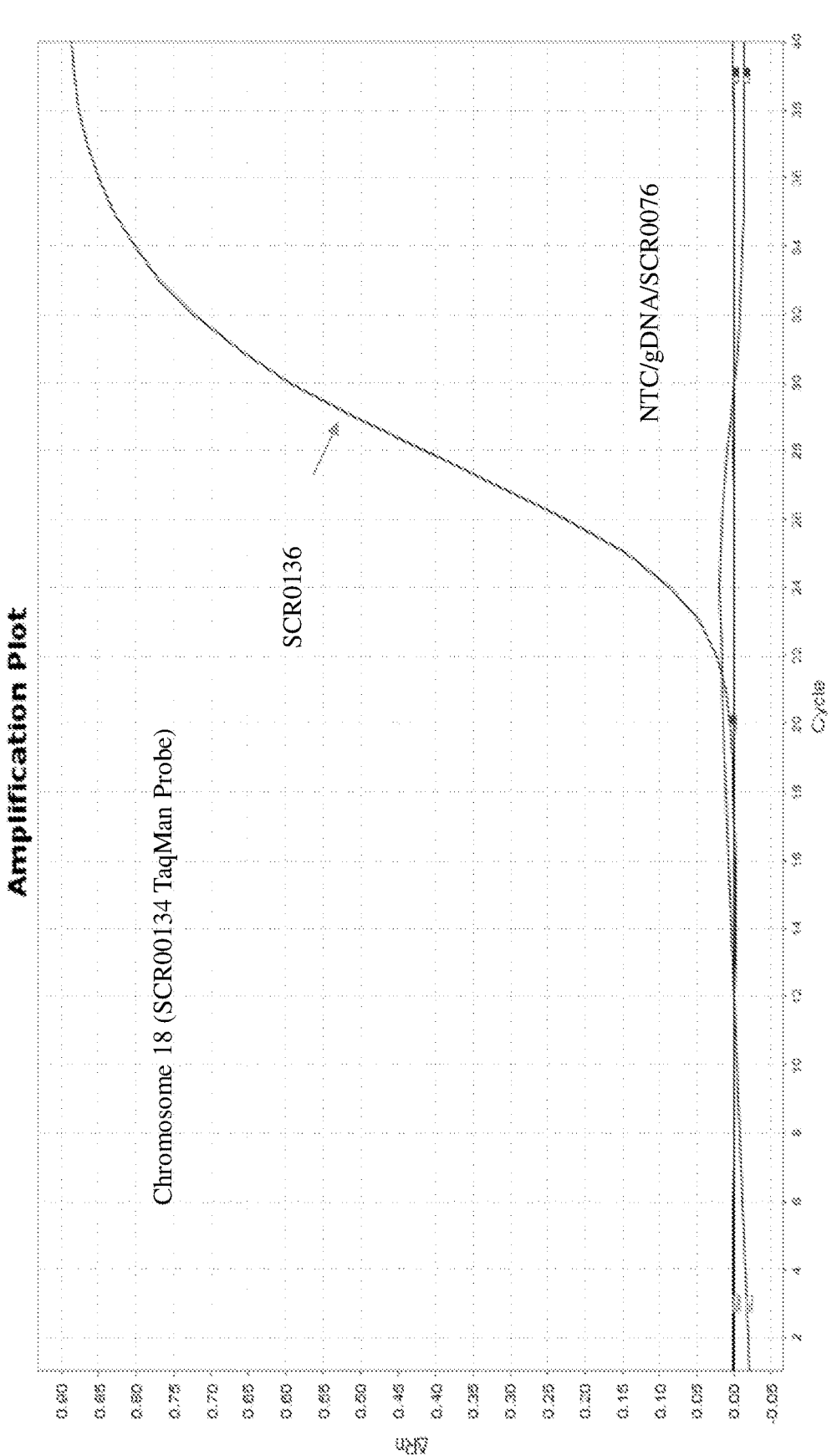

FIG. 31A includes amplification plots showing that the SCR0078 TaqMan Probe only amplifies the SSR Target, SCR0076. Genomic DNA, SCR0136, and non-template controls were not amplified. In FIG. 31B, the amplification plots show that SCR00134 TaqMan Probe only amplifies the SSR Target, SCR0136. Genomic DNA, SCR0076, and non-template controls were not amplified.

A full workflow with multiplex detection of targes on two different human chromosomes (with dPCR Readout) was also performed. Specific multiplex detection of targets on two human chromosomes by two SCPs, one specific for chromosome 21 (SCR0083; site NC_000021.9_27305245), the other specific for chromosome 18 (SCR0133; site NC_000018.10_647934), both mapped to GRCh38.p13 Primary Assembly_647934. Digital PCR was used as the detection method for absolute quantitation. Human genomic DNA was not detected when in the absence of the SCPs.

Sequence Conversion Probes (SCPs) SCR0083 (0.5 nM; SEQ ID No. 83; IDT) specific for chromosome 21 (NC_000021.9_27305245) and SCR0133 (0.5 nM; SEQ ID No. 99; IDT) specific for chromosome 18 (NC_000018.10_647934) were annealed with 100 ng of human genomic DNA derived from HeLa cell line (NEB; cat #N4006) in 10 mM Tris-HCl, 1 mM Na2-EDTA, 100 mM NaCl, 10 mM MgCl2, pH 8.0 (40 ml) by heating to 95° C. for 5 min, cooling at 0.015 C/sec to 50° C. and holding for 5 min. The SCPs annealed to genomic DNA were digested with BspQI (20 U; NEB cat #R0712) for 60 min at 60° C. in a final digestion buffer comprised of 50 mM Tris-HCl, 100 mM NaCl, 10 mM MgCl2, 100 mg/ml BSA. The digestion was followed by a 20-minute heat inactivation step at 80° C. The SSRs of the digested SCPs were then ligated by treatment with Hi-T4 ligase (60 U; NEB cat #M2622) for 70 minutes at 50° C. in 50 mM Tris-HCl, 20 mM MgCl2, 1.5 mM ATP, 0.5 nM of each Lock Probe SCR0080 (SeqID 3; IDT) and SCR0135 (SEQ ID No. 93; IDT). The ligation was followed by a 10 min heat inactivation step at 65° C. The circularized SSRs were then amplified and detected by digital PCR using QIAcuity Probe PCR Kit (Qiagen cat #250101), 800 nM forward and reverse primers (SSR1_FP, SEQ ID No. 85; SSR1_RP, SEQ ID No. 87; IDT) and 400 nM TaqMan probe SCR0078 (SEQ ID No. 88; IDT) and SCR0134 (SEQ ID No. 91; IDT) by denaturation at 95° C. for 2′ followed by 40 cycles of 95° C. for 15″ and 60° C. for 30″ on the QIAcuity digital PCR System (Qiagen, Netherlands) using a 26K 24-well nanoplate. The positive and negative partitions in the FAM and HEX channel were quantified using the QIAcuity Software Suite 1.2.18 (Qiagen) and converted into absolute concentration (copies/ml) as shown in Table 2. As a negative control genomic DNA was treated in the absence of SCPs to the full workflow.

The absolute quantification for chromosome 21- and chromosome 18-derived products are shown in the Table 2. The ratio is not 1:1 likely because HeLa cell lines are known to be hyperploid. The negative control with HeLa gDNA only (no SCPs) yielded 0 positive partitions and 0 copy/ul in both the Fam and Hex channels.

TABLE 2

| Sample | Target | Conc (copies/μL) | Partitions (valid) | Partitions (positive) | Partitions (negative) |
|---|---|---|---|---|---|
| SCR083 and SCR0133 on HeLa gDNA | Chr 18 | 300.4 | 25480 | 5671 | 19809 |
| | Chr 21 | 1821.2 | 25479 | 19941 | 5538 |

A two-part assay with an SCP, including Linear Ligation and qPCR was also performed, similar to FIGS. 29A and 29B, described above. This two-part SCP assay, a reverse primer binding site replaces the TSR following removal of the TSR by nuclease cleavage. The primer binding region, also termed the SSR extension probe, can be joined to the short cSSR by one ligation event to generate a linear single-stranded SSR (see, e.g., FIG. 29B), or by two ligation events to generate a covalently closed circular single-stranded SSR (see, e.g., FIG. 29C). The resulting SSR may be detected by qPCR. An example of a single ligation event to produce a linear SSR was performed as described herein.

For example, 2e4 copy/ml of Short SSR (SCR0146, SEQ ID No. 97) and 0.5 nM SSR extension probe with or without 3' Phosphate (SCR0142, SEQ ID No. 95, or SCR0142a, SEQ ID No. 96) were ligated in the presence of 0.5 nM Lock Probe (SCR0147, SEQ ID No. 98) by treatment with Hi-T4 ligase (60 U; NEB cat #M2622) for 70 minutes at 50° C. in 50 mM Tris-HCl, 20 mM MgCl2, 1.5 mM ATP. The ligation was followed by a 10 min heat inactivation step at 65° C. The ligation product was then amplified and detected by real-time PCR using TaqMan Fast Advanced MasterMix (ThermoFisher cat #4444556), 200 nM forward and reverse primers (SSR1_FP, SEQ ID No. 86; SSR1_RP, SEQ ID No. 87; IDT) and 100 nM TaqMan probe SCR0078 (SEQ ID No. 88; IDT) by denaturation at 95° C. for 20" followed by 40 cycles of 95° C. for 1" and 60° C. for 20" QuantStudio Real Time PCR System (ThermoFisher Scientific).

Figure 32A:
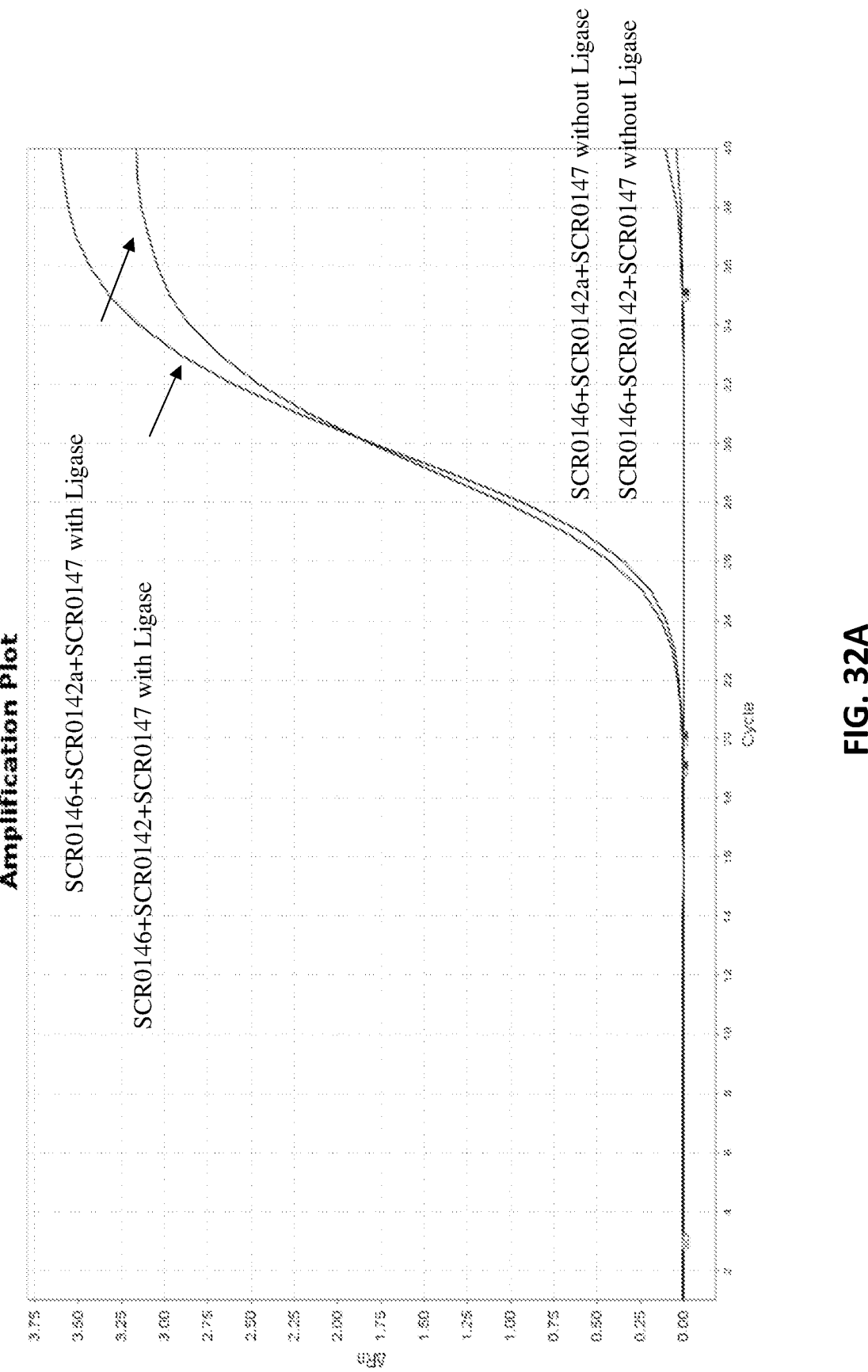
FIGS. 32A-32C show amplification plots for one example of a sequence conversion method as described herein, similar to that shown in FIGS. 29A-29D.
Figure 32B:
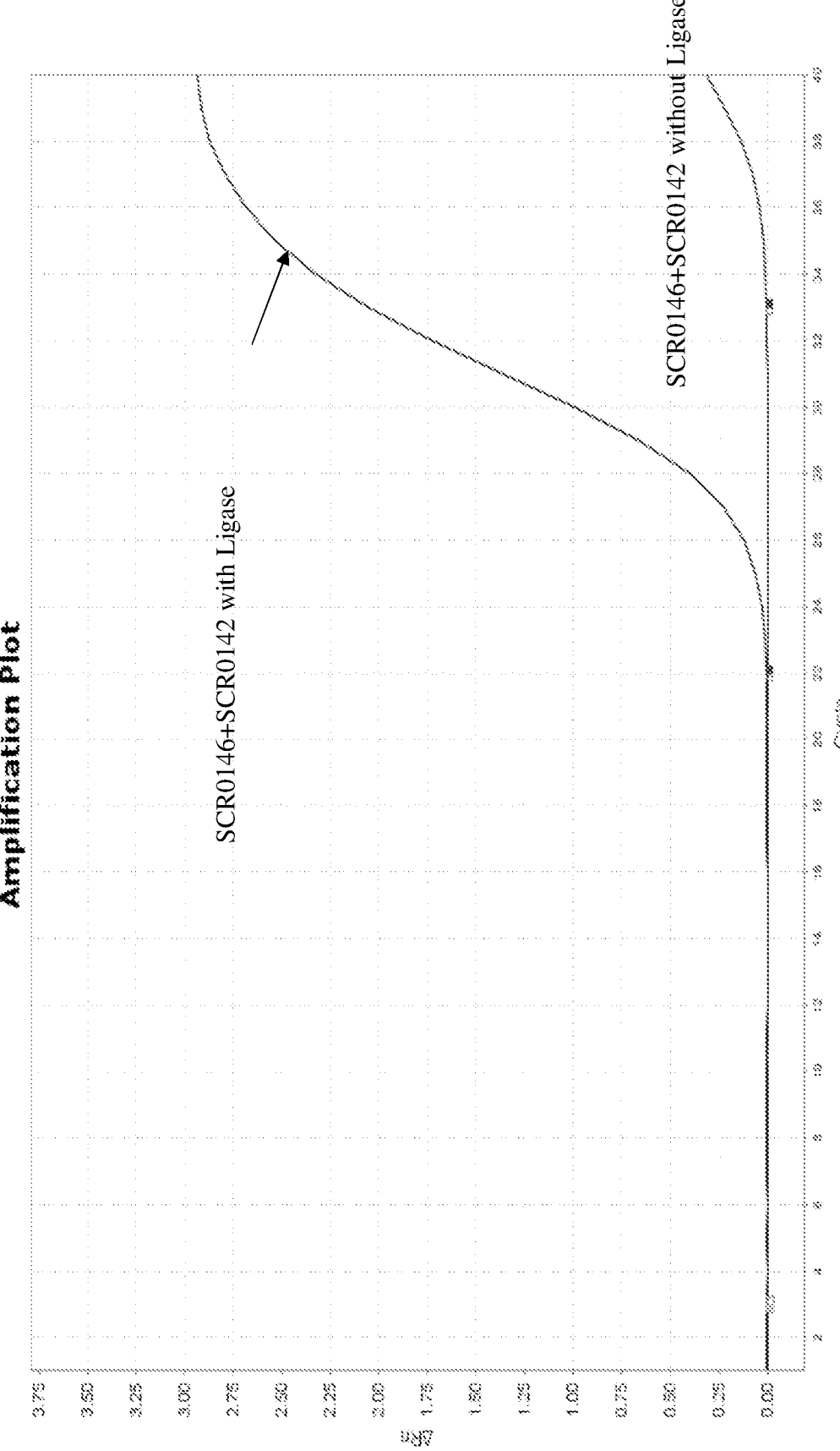
Figure 32C:
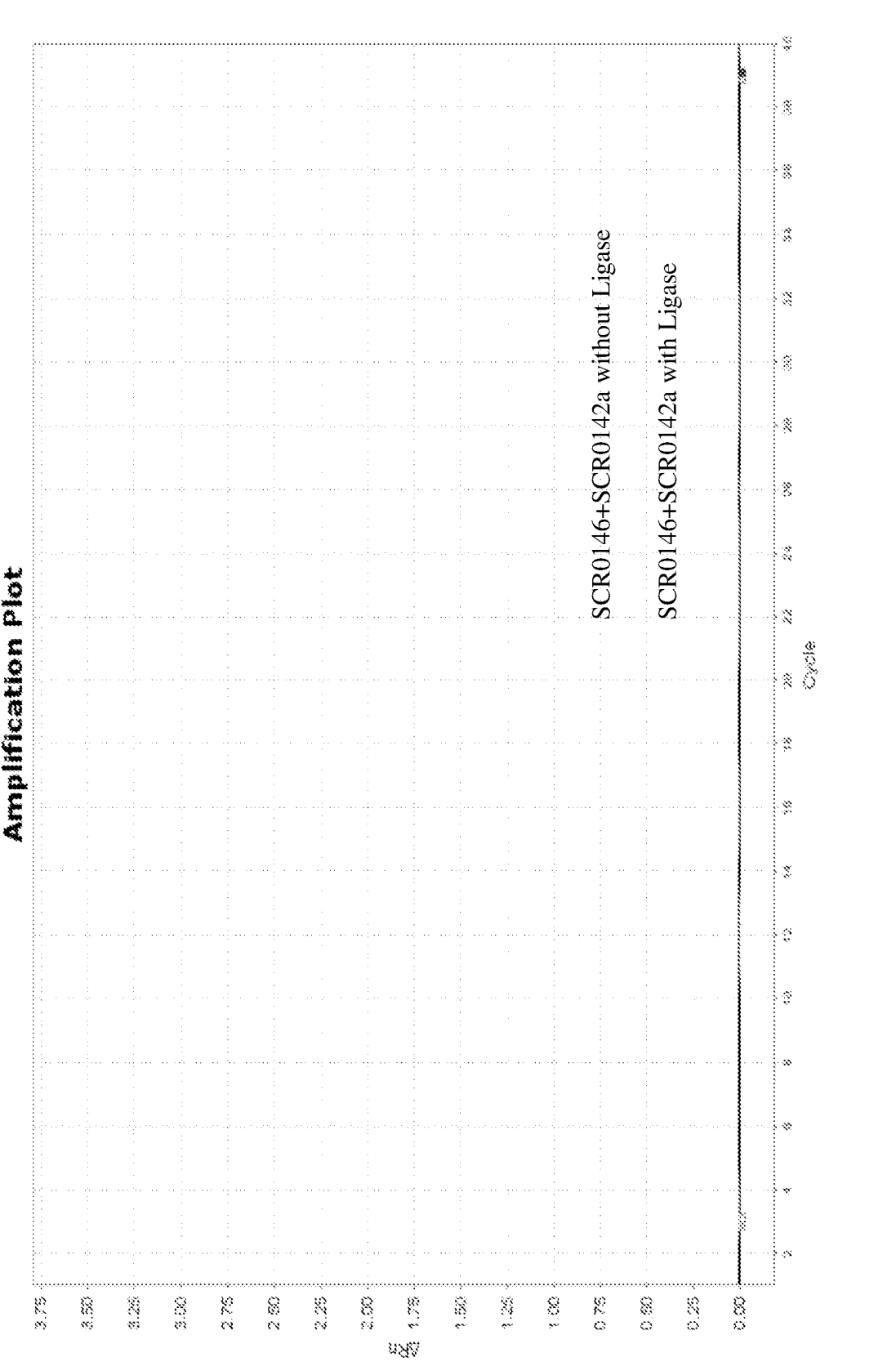

FIGS. 32A-32C show amplification plots. For example, FIG. 32A show the results of amplification with and without ligase. FIG. 32B shows results with and without ligase, and FIG. 32C also shows control results with and without ligase. Ligation may occur with SCR0146 (Short-SSR), SCR0147 (Lock Probe), and either SCR0142 or SCR0142a (Sub-SCP). Ligation also occurred with just SCR0146 and SCR0142, without Lock Probe (unspecific ligation). No ligation occurred with just SCR0146 and SCR0142a. 3' Phosphate on the sub-SCP blocks unspecific ligation.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A method, comprising:

combining a first plurality of sequence conversion probes (SCPs) with a sample mixture including one or more target measurand, wherein each SCP comprises a polynucleotide including a target-specific region (TSR) and a circularizable signal specific region (SSR), the circularizable SSR comprising a first engineered polynucleotide marker including one or more primer regions, further wherein the first plurality of SCPs comprise a plurality of different TSRs configured to hybridize to different target measurands, wherein each SCP of the first plurality of SCPs includes the same SSR;

hybridizing the TSRs to the one or more target measurand within the sample mixture;

cutting SCPs having TSRs that are hybridized to the one or more target measurands to release cut SSRs (cSSRs) without releasing SSRs of un-hybridized SCPs; and hybridizing each of the cSSRs to a lock probe to produce circularization complexes;

contacting the circularization complexes with a circularizing agent to circularize the cSSRs; and detecting the first engineered polynucleotide marker from the circularized cSSRs.

2. The method of claim 1, wherein hybridizing each of the cSSRs to the lock probe comprises hybridizing each of the cSSRs to the lock probe and an SSR extension probe, wherein the SSR extension probe comprises a primer for use in detecting the first engineered polynucleotide marker.

3. The method of claim 1, wherein the SSR is configured not to hybridize to a measurand in the sample mixture.

4. The method of claim 1, wherein detecting the first engineered polynucleotide marker comprises performing digital PCR using the circularized cSSRs (cirSSRs) and one or more primers configured to hybridize to the one or more primer regions to amplify the first engineered polynucleotide marker.

5. The method of claim 4, wherein performing digital PCR comprises distributing the pool of cirSSRs into a plurality of reaction samples at a dilution such that at least some of the reaction samples contain cirSSRs and some do not contain cirSSRs.

6. The method of claim 4, further comprising analyzing the first engineered polynucleotide marker of the cSSRs present or absent in individual reaction samples to provide a first number of binary results representing presence or absence of a presumably euploid chromosome in the reaction samples and a second number of binary results representing presence or absence of a presumably aneuploid chromosome in the reaction samples.

7. The method of claim 6, further comprising determining the presence or absence of an aneuploidy by comparing said first number with said second number, wherein a differential between the first number and the second number indicates the presence of aneuploidy.

8. The method of claim 1, wherein hybridizing each of the cSSRs to the lock probe comprises using a same polynucleotide sequence for the lock probe to hybridize to all of the cSSRs.

9. The method of claim 1, further comprising digesting non-circular DNA in the mixture with one or more exonuclease after contacting the circularization complexes with the circularizing agent.

10. The method of claim 1, wherein the one or more target measurand in the sample mixture comprises cell-free DNA (cfDNA).

11. The method of claim 1, wherein the sample mixture comprises a mixture of maternal and fetal genetic material from a maternal blood sample.

12. The method of claim 1, wherein the circularizing agent is a ligase.

13. The method of claim 1, wherein the circularizable SSR further comprises a first hybridization region and a second hybridization region, wherein the first hybridization region and the second hybridization region are configured to hybridize to the lock probe.

14. The method of claim 1, wherein the one or more primer regions comprises a forward primer region and a reverse primer region arranged on the circularizable SSR so that PCR amplification primers directed to the forward primer region and the reverse primer region cannot amplify the first engineered polynucleotide marker on the circularizable SSR unless the circularizable SSR is circularized.

15. The method of claim 14, wherein the lock probe is configured to hybridize to at least a portion of the forward primer region and to a probe region to produce circularization complexes.

16. The method of claim 1, wherein combining the first plurality of SCPs further comprises combining a second plurality of SCPs with the sample mixture, wherein the second plurality of SCPs comprise a plurality of different TSRs configured to hybridize to different target measurands, wherein each SCP of the second plurality of SCPs includes a same second SSR, wherein the same second SSR is different from the SSR of the first plurality of SCPs.

17. The method of claim 1, wherein detecting the first engineered polynucleotide marker from the circularized cSSRs comprises a method of detecting minimal residual disease.

18. The method of claim 1, wherein detecting the first engineered polynucleotide marker from the circularized cSSRs comprises a method of detecting transplant rejection.

\*  \*  \*  \*  \*